(12) United States Patent
Bonaldo et al.

(10) Patent No.: US 8,828,687 B2
(45) Date of Patent: Sep. 9, 2014

(54) METHOD FOR THE PRODUCTION OF RECOMBINANT VIRUS, DNA CONSTRUCTS, RECOMBINANT VIRUS AND VACCINE COMPOSITIONS

(76) Inventors: Myrna Cristina Bonaldo, Rio de Janeiro (BR); Ricardo Galler, Niterói (BR)

( * ) Notice: Subject to any disclaimer, the term of this patent is extended or adjusted under 35 U.S.C. 154(b) by 1536 days.

(21) Appl. No.: 12/084,387

(22) PCT Filed: Oct. 31, 2006

(86) PCT No.: PCT/BR2006/000237
§ 371 (c)(1),
(2), (4) Date: Jul. 15, 2008

(87) PCT Pub. No.: WO2007/051267
PCT Pub. Date: May 10, 2007

(65) Prior Publication Data
US 2010/0297167 A1    Nov. 25, 2010

(30) Foreign Application Priority Data

Oct. 31, 2005  (BR) ........................... 0504945

(51) Int. Cl.
*C12P 21/00*    (2006.01)
*A61K 39/12*   (2006.01)

(52) U.S. Cl.
USPC ....................... 435/71.1; 424/218.1

(58) Field of Classification Search
None
See application file for complete search history.

(56) References Cited

FOREIGN PATENT DOCUMENTS

WO    WO 01/39802 A1  *  7/2001

OTHER PUBLICATIONS

Breedenbeek et al., Virology, Jan. 18, 2006, 345(2):299-304.*
International Search Report, International Application No. PCT/BR2006/000237.

* cited by examiner

*Primary Examiner* — Stacy B. Chen
(74) *Attorney, Agent, or Firm* — Caesar, Rivise, Bernstein, Cohen & Pokotilow, Ltd.

(57) ABSTRACT

The purpose of the present invention is the production of recombinant virus through the cloning and expression of sequences of coding nucleotides of the whole or part of heterolog proteins, through the following method: (a) modification of the heterolog nucleotides sequences in such way they when cloned and expressed in the vector virus, they present in the 5' region, nucleotides present in the 5' edge of the gene NS1 of this vector virus or of other virus or equivalent functional sequences, and in its 3' region, the correspondent genome region in the whole or part of the spheres of the steam and anchor of the protein E of this vector virus or equivalent functional sequences, and not compromising the structure and the replication of the mention vector virus; (b) insertion of the modified heterolog sequences in (a) in the intergene region at the structural protein E level and of on structural NS1 vector virus; (c) obtention of the non pathogenic recombinant virus and owner of the immunologic properties, having the heterolog sequences integrated in the viral genome according to the insertion described in (b) and, like that, expressing the heterolog antigene in such way that it can induce an appropriate immune response. The present invention is also addressed to vaccine compositions to immune against the *Flavivirus* and/or other pathogens.

8 Claims, 26 Drawing Sheets

| virus | C-terminal E (7 residues) | N-terminal NS1 (9 residues) |
|---|---|---|
| FA | L S L G V G A | D Q G C A I N F G |
| JE | L A T N V H A | D T G C A I D I T |
| Den 2 | L G V M V Q A | D S G C V V S W K |
| Den 4 | L G F T V Q A | D M G C V A S W S |
| WN | L S V N V H A | D T G C A I D I G |
| TBE | M T L G V G A | D V G C A V D T E |

(B)

Motif             V X A ↓ D X G C
Consense

```
                1                                                                                               96
TBE  RVFQKTKKGIERLTVIGEHAWDFGSAGGFLSSIGKAVHTVLGGAFNSIFGGVGFLPKLLLGVALAWLGLNMRNPTMSMSFLLAGGLVLAMTLGVGA
FA   KLFTQTMKGVERLAVMGDTAWDFSSAGGFFTSVGKGIHTVFGSAFQGLFGGLNWITKVIMGAVLIWGINTRNMTMSMSMILVGVIMMFLSLGVGA
     ::* .:* **:.***:*:*: ****.******.:***..*:::*: **.* *:*:.* ** ******::*. :::  ::******
                    H1       CS          H2                  TMD 1                       TMD 2
```

(B)

| virus | N-terminal NS1 (9 residues) |
|---|---|
| FA | D Q G C A I N F G |
| JE | D T G C A I D I T |
| Den 2 | D S G C V V S W K |
| Den 4 | D M G C V A S W S |
| WN | D T G C A I D I G |
| TBE | D V G C A V D T E |

Figure 8

Insertion point of protein EGFP into viral polyprotein

(A)

E....M T M S M S M I L V G V I M M F L S L G V G A     D Q G C A I N F G....NS1

⎧⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎧ ⇧ ⎧⎯⎯⎯⎯⎯⎯⎯⎧

E TMD 2                                                         N-terminal NS1

(B)

TMD 2       ⇩

E .... MTMSMSMILVGVIMMFLSLGVGA     DQGCAINFGVSKGEELFTGVVPILVELDGDVNGHKFSVSGEGEGDATYGKLTLKF
ICTTGKLPVPWPTLVTTLTYGVQCFSRYPDHMKQHDFFKSAMPEGYVQERTIFFKDDGNYKTRAEVKFEGDTLVNRIELKGIDFKEDG
NILGHKLEYNYNSHNVYIMADKQKNGIKVNFKIRHNIEDGSVQLADHYQQNTPIGDGPVLLPDNHYLSTQSALSKDPNEKRDHMVLLE
FVTAAGITLGMDELYKKLFTQTMKGVERLAVMGDTAWDFSSAGGFFTSVGKGIHTVFGSAFQGLFGGLNWITKVIMGAVLIWVGINTR
NMTMSMSMILVGVIMMFLSLGVGA    DGCAINFG....NS1
                                 ⇧
                          N-terminal NS1

5'...-482 [ prM | E | | NS1 ] 3508...-3'

Nar I ↓ (above NS1 boundary)

↑ Rod / Anchor

(B) 17D/Esa/5.1 glic

5'...-482 [ prM | E | | EGFP | | NS1 ] 4537...-3'

Nar I ↓    Nar I ↓

↑↑ N-terminal NS1    ↑

Stem / Anchor    Stem / Anchor

(C)

| Gene/ position FA 17D (nt) | 5' | 3' |
|---|---|---|
| PrM | 482 | 973 |
| E | 974 | 2452 |
| E – stem anchor domain | 2165 | 2452 |
| NS1- N-terminal portion | 2453 | 2479 |
| NS1 | 2453 | 3508 |
| Gene/ position 17D/Esa/5.1 glic (nt) | 5' | 3' |
| PrM | 482 | 973 |
| E | 974 | 2452 |
| E – stem anchor domain | 2165 | 2452 |
| EGFP N- terminal of NS1 portion | 2453 | 2479 |
| EGFP | 2480 | 3193 |
| EGFP – stem anchor domain of E | 3194 | 3481 |
| NS1 | 3482 | 4537 |

Figure 12

Growth kinetic of FA 17D/Esa/5.1$_{glic}$ viruses expressing EGFP (moi 0.02)

- ··○·· 17DD  — □ — 17D/14  — △ — 17D/Esa/5.1 glic x-axis: time p.i. (hours)
y-axis: Log$_{10}$ PFU / mL

Figure 13 ic Challenge with FA 17DD virus

□ medium control
□ 17DD
□ 17D/E200T3
□ 17D/Esa/5.1glic

| Group | Medium | 17DD | 17D/E200$_{glic}$T3 | 17D/Esa/5.1$_{glic}$T3 |
|---|---|---|---|---|
| Mortality (%) | 100 | 13,3 | 40 | 50 |
| Mean time of overlife ± standard deviation (days) | 11 ± 0,94 | 4 ± 0* | 4 ± 0* | 4 ± 0* |
| Number of animals | 10 | 15 | 15 | 20 |
| Median dose/immunization | - | 62.000 | 85.000 | 40.000 |

(A) 17D/Den4/Esa/EGFP/6

(B) Position of genic sequences in the chimeric viral genome 17D/FA/Den4/Esa/EGFP/6

| Gene/position (nt) 17D/FA/Den4/Esa/EGFP/6 | 5′ | 3′ |
|---|---|---|
| C | 119 | 484 |
| prM den4 | 485 | 982 |
| E den4 | 983 | 2467 |
| E - stem anchor domain of E den4 | 2180 | 2467 |
| N- terminal of NS1 | 2468 | 2494 |
| EGFP | 2495 | 3208 |
| EGFP - stem anchor domain of E | 3209 | 3496 |
| NS1 | 3497 | 4552 |

Figure 20

| virus | hours p.i. | 24 | 48 | 72 | 96 | 122 | 140 |
|---|---|---|---|---|---|---|---|
| 17DD | log10 PFU/mL | 5,02 ± 0,25 | 6,95 ± 0,21 | 7,17 ± 0,03 | 7,13 ± 0,21 | 6,84 ± 0,28 | 7,01 ± 0,21 |
| FA/ DEN 4/4P | | 3,53 ± 0,27 | 5,35 ± 0,12 | 6,69 ± 0,21 | 6,45 ± 0,40 | 6,21 ± 0,28 | 6,42 ± 0,18 |
| FA/DEn4/ Esa/EGFP/ 6 | | 2,38 ± 0,54 | 3,70 ± 0,69 | 5,27 ± 0,33 | 6,31 ± 0,13 | 5,74 ± 0,28 | 5,79 ± 0,31 |

Genetic stability of 17D/FA/Den4/Esa/EGFP/6 virus in serial culture in monolayers of Vero cells

SEQUENCE LISTING

<160> NUMBER OF SEQ ID NOS: 47

<210> SEQ ID NO 1
<211> LENGTH: 27
<212> TYPE: DNA
<213> ORGANISM: Yellow Fever Virus

<400> SEQUENCE: 1
gatcaaggat gcgccatcaa ctttggc                                        27

<210> SEQ ID NO 2
<211> LENGTH: 714
<212> TYPE: DNA
<213> ORGANISM: Yellow fever virus

<400> SEQUENCE: 2
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg gcccaccctc   180
gtgaccaccc tgacctacgg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga cacactggtg   360
aaccgcatcg agctgaaggg catcgacttc aaggaggacg gcaacatcct ggggcacaag   420
ctggagtaca actacaacag ccacaacgtc tatatcatgg ccgacaagca gaagaacggc   480
atcaaggtga acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccgccct gagcaaagac cccaacgaga gcgcgatca catggtcctg    660 ctggagttcg tgaccgccgc cgggatcact ctcggcatgg acgagctgta caag          714

<210> SEQ ID NO 3
<211> LENGTH: 288
<212> TYPE: DNA
<213> ORGANISM: Yellow fever virus

<400> SEQUENCE: 3
aagttgttca ctcagaccat gaaaggcgtg gaacgcctgg ccgtcatggg agacaccgcc    60
tgggatttca gctccgctgg agggttcttc acttcggttg ggaaaggaat tcatacggtg   120
tttggctctg cctttcaggg gctatttggc ggcttgaact ggataacaaa ggtcatcatg   180
ggggcggtac ttatatgggt tggcatcaac acaagaaaca tgacaatgtc catgagcatg   240
atcttggtag gagtgatcat gatgtttttg tctctaggag ttggcgcc                 288

<210> SEQ ID NO 4
<211> LENGTH: 1029
<212> TYPE: DNA
<213> ORGANISM: recombinant yellow fever virus

<400> SEQUENCE: 4
gatcaaggat gcgccatcaa ctttggcgtg agcaagggcg aggagctgtt caccggggtg    60
gtgcccatcc tggtcgagct ggacggcgac gtaaacggcc acaagttcag cgtgtccggc   120
gagggcgagg gcgatgccac ctacggcaag ctgaccctga agttcatctg caccaccggc   180
aagctgcccg tgccctggcc caccctcgtg accaccctga cctacggcgt gcagtgcttc   240
agccgctacc ccgaccacat gaagcagcac gacttcttca gtccgccat gcccgaaggc    300

```
tacgtccagg agcgcaccat cttcttcaag gacgacggca actacaagac ccgcgccgag    360
gtgaagttcg agggcgacac cctggtgaac cgcatcgagc tgaagggcat cgacttcaag    420
gaggacggca acatcctggg gcacaagctg agtacaact acaacagcca caacgtctat    480
atcatggccg acaagcagaa gaacggcatc aaggtgaact tcaagatccg ccacaacatc    540
gaggacggca gcgtgcagct cgccgaccac taccagcaga caccccat cggcgacggc     600 cccgtgctgc tgcccgacaa ccactacctg agcacccagt ccgccctgag caaagacccc    660
aacgagaagc gcgatcacat ggtcctgctg gagttcgtga ccgccgccgg gatcactctc    720
ggcatggacg agctgtacaa gaagttgttc actcagacca tgaaaggcgt ggaacgcctg    780
gccgtcatgg agacaccgc ctgggatttc agctccgctg agggttctt cacttcggtt     840 gggaaaggaa ttcatacggt gtttggctct gcctttcagg ggctatttgg cggcttgaac    900
tggataacaa aggtcatcat gggggcggta cttatatggg ttggcatcaa cacaagaaac    960
atgacaatgt ccatgagcat gatcttggta ggagtgatca tgatgttttt gtctctagga   1020
gttggcgcc                                                            1029
```

<210> SEQ ID NO 5
<211> LENGTH: 9
<212> TYPE: PRT
<213> ORGANISM: yellow fever virus

<400> SEQUENCE: 5

Asp Gln Gly Cys Ala Ile Asn Phe Gly
1               5

<210> SEQ ID NO 6
<211> LENGTH: 238
<212> TYPE: PRT
<213> ORGANISM: Artificial Sequence
<220> FEATURE:
<223> OTHER INFORMATION: amino acid sequence of EGFP expressed by
      recombinant YF virus

<400> SEQUENCE: 6

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Leu
        50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

-continued

```
Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235

<210> SEQ ID NO 7
<211> LENGTH: 96
<212> TYPE: PRT
<213> ORGANISM: yellow fever virus

<400> SEQUENCE: 7

Lys Leu Phe Thr Gln Thr Met Lys Gly Val Glu Arg Leu Ala Val Met
1               5                   10                  15

Gly Asp Thr Ala Trp Asp Phe Ser Ser Ala Gly Gly Phe Phe Thr Ser
            20                  25                  30

Val Gly Lys Gly Ile His Thr Val Phe Gly Ser Ala Phe Gln Gly Leu
        35                  40                  45

Phe Gly Gly Leu Asn Trp Ile Thr Lys Val Ile Met Gly Ala Val Leu
    50                  55                  60

Ile Trp Val Gly Ile Asn Thr Arg Asn Met Thr Met Ser Met Ser Met
65                  70                  75                  80

Ile Leu Val Gly Val Ile Met Met Phe Leu Ser Leu Gly Val Gly Ala
                85                  90                  95

<210> SEQ ID NO 8
<211> LENGTH: 343
<212> TYPE: PRT
<213> ORGANISM: recombinant yellow fever virus

<400> SEQUENCE: 8

Asp Gln Gly Cys Ala Ile Asn Phe Gly Val Ser Lys Gly Glu Glu Leu
1               5                   10                  15

Phe Thr Gly Val Val Pro Ile Leu Val Glu Leu Asp Gly Asp Val Asn
            20                  25                  30

Gly His Lys Phe Ser Val Ser Gly Glu Gly Glu Gly Asp Ala Thr Tyr
        35                  40                  45

Gly Lys Leu Thr Leu Lys Phe Ile Cys Thr Thr Gly Lys Leu Pro Val
    50                  55                  60

Pro Trp Pro Thr Leu Val Thr Thr Leu Thr Tyr Gly Val Gln Cys Phe
65                  70                  75                  80

Ser Arg Tyr Pro Asp His Met Lys Gln His Asp Phe Phe Lys Ser Ala
                85                  90                  95

Met Pro Glu Gly Tyr Val Gln Glu Arg Thr Ile Phe Phe Lys Asp Asp
            100                 105                 110

Gly Asn Tyr Lys Thr Arg Ala Glu Val Lys Phe Glu Gly Asp Thr Leu
        115                 120                 125

Val Asn Arg Ile Glu Leu Lys Gly Ile Asp Phe Lys Glu Asp Gly Asn
    130                 135                 140

Ile Leu Gly His Lys Leu Glu Tyr Asn Tyr Asn Ser His Asn Val Tyr
145                 150                 155                 160
```

-continued

```
Ile Met Ala Asp Lys Gln Lys Asn Gly Ile Lys Val Asn Phe Lys Ile
            165                 170                 175
Arg His Asn Ile Glu Asp Gly Ser Val Gln Leu Ala Asp His Tyr Gln
        180                 185                 190
Gln Asn Thr Pro Ile Gly Asp Gly Pro Val Leu Leu Pro Asp Asn His
    195                 200                 205
Tyr Leu Ser Thr Gln Ser Ala Leu Ser Lys Asp Pro Asn Glu Lys Arg
210                 215                 220
Asp His Met Val Leu Leu Glu Phe Val Thr Ala Ala Gly Ile Thr Leu
225                 230                 235                 240
Gly Met Asp Glu Leu Tyr Lys Lys Leu Phe Thr Gln Thr Met Lys Gly
            245                 250                 255
Val Glu Arg Leu Ala Val Met Gly Asp Thr Ala Trp Asp Phe Ser Ser
        260                 265                 270
Ala Gly Gly Phe Phe Thr Ser Val Gly Lys Gly Ile His Thr Val Phe
    275                 280                 285
Gly Ser Ala Phe Gln Gly Leu Phe Gly Gly Leu Asn Trp Ile Thr Lys
290                 295                 300
Val Ile Met Gly Ala Val Leu Ile Trp Val Gly Ile Asn Thr Arg Asn
305                 310                 315                 320
Met Thr Met Ser Met Ser Met Ile Leu Val Gly Val Ile Met Met Phe
            325                 330                 335
Leu Ser Leu Gly Val Gly Ala
            340
```

<210> SEQ ID NO 9
<211> LENGTH: 62
<212> TYPE: DNA
<213> ORGANISM: recombinant yellow fever virus

<400> SEQUENCE: 9
ctaggagttg gcgccgatca aggatgcgcc atcaactttg gcgtgagcaa gggcgaggag    60
ct                                                                  62

<210> SEQ ID NO 10
<211> LENGTH: 51
<212> TYPE: DNA
<213> ORGANISM: recombinant yellow fever virus

<400> SEQUENCE: 10
gcctttcatg gtctgagtga acaacttctt gtacagctcg tccatgccga g             51

<210> SEQ ID NO 11
<211> LENGTH: 51
<212> TYPE: DNA
<213> ORGANISM: recombinant yellow fever virus

<400> SEQUENCE: 11
ctcggcatgg acgagctgta caagaagttg ttcactcaga ccatgaaagg c             51

<210> SEQ ID NO 12
<211> LENGTH: 46
<212> TYPE: DNA
<213> ORGANISM: recombinant yellow fever virus

<400> SEQUENCE: 12
gccaaagttg atggcgcatc cttgatcggc gccaactcct agagac                   46

```
<210> SEQ ID NO 13
<211> LENGTH: 11890
<212> TYPE: DNA
<213> ORGANISM: recombinant yellow fever virus

<400> SEQUENCE: 13
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
ctccttgtca aacaaataa aacaaaaaac aaaacaaatt ggaaacagac ctggaccttc      240
aagaggtgtt caaggattta tctttttctt tttgttcaac attttgactg gaaaaaagat     300
cacagcccac ctaaagaggt tgtggaaaat gctggaccca agacaaggct tggctgttct     360
aaggaaagtc aagagagtgg tggccagttt gatgagagga ttgtcctcaa ggaaacgccg     420
ttcccatgat gttctgactg tgcaattcct aattttggga atgctgttga tgacgggtgg     480
agtgaccttg gtgcggaaaa acagatggtt gctcctaaat gtgacatctg aggacctcgg     540
gaaaacattc tctgtgggca caggcaactg cacaacaaac attttggaag ccaagtactg     600
gtgcccagac tcaatggaat acaactgtcc caatctcagt ccaagagagg agccagatga     660
cattgattgc tggtgctatg gggtggaaaa cgttagagtc gcatatggta agtgtgactc     720
agcaggcagg tctaggaggt caagaaggc cattgacttg cctacgcatg aaaaccatgg     780
tttgaagacc cggcaagaaa aatggatgac tggaagaatg ggtgaaaggc aactccaaaa     840
gattgagaga tggttcgtga ggaaccccct ttttgcagtg acggctctga ccattgccta     900
ccttgtggga agcaacatga cgcaacgagt cgtgattgcc ctactggtct ggctgttgg      960 tccggcctac tcagctcact gcattggaat tactgacagg gatttcattg agggggtgca    1020
tggaggaact tgggtttcag ctaccctgga gcaagacaag tgtgtcactg ttatggcccc    1080
tgacaagcct tcattggaca tctcactaga gacagtagcc attgatagac ctgctgaggt    1140
gaggaaagtg tgttacaatg cagttctcac tcatgtgaag attaatgaca gtgccccag     1200 cactggagag gcccacctag ctgaagagaa cgaaggggac aatgcgtgca gcgcacttac    1260
ttctgataga ggctggggca atggctgtgg cctatttggg aaagggagca ttgtggcatg    1320
cgccaaattc acttgtgcca aatccatgag tttgtttgag gttgatcaga ccaaaattca    1380
gtatgtcatc agagcacaat gcatgtagg ggccaagcag gaaaattgga taccagcat     1440 taagactctc aagtttgatg ccctgtcagg ctcccaggaa gtcgagttca ttgggtatgg    1500
aaaagctaca ctggaatgcc aggtgcaaac tgcggtggac tttggtaaca gttacatcgc    1560
agagatggat atcgagagct ggatagtgga cagacagtgg gcccaggact tgaccctgcc    1620
atggcagagt ggaagtggcg gggtgtgag agagatgcat catcttgtcg aatttgaacc    1680
tccgcatgcc gccactatca gagtactggc cctgggaaac caggaaggct ccttgaaaac    1740
agctcttact ggcgcaatga gggttacaaa ggacacaaat gacaacaacc tttacaaact    1800
acatggtgga catgtttctt gcagagtgaa attgtcagct tgacactca aggggacatc    1860 ctacaaaata tgcactgaca aaatgttttt tgtcaagaac ccaactgaca ctggccatgg    1920
cactgttgtg atgcaggtga aagtgtcaaa aggaacccc tgcaggattc cagtgatagt    1980
agctgatgat cttacagcgg caatcaataa aggcatttg gttacagtta accccatcgc    2040
ctcaaccaat gatgatgaag tgctgattga ggtgaaccca ccttttggag acagctacat    2100
tatcgttggg agaggagatt cacgtctcac ttaccagtgg cacaaagagg gaagctcaat    2160
```

```
aggaaagttg ttcactcaga ccatgaaagg cgtggaacgc ctggccgtca tgggagacac   2220
cgcctgggat ttcagctccg ctggagggtt cttcacttcg gttgggaaag gaattcatac   2280
ggtgtttggc tctgcctttc aggggctatt tggcggcttg aactggataa caaaggtcat   2340
catgggggcg gtactcatat gggttggcat caacacaaga aacatgacaa tgtccatgag   2400
catgatcttg gtaggagtga tcatgatgtt tttgtctcta ggagttggcg ccgatcaagg   2460
atgcgccatc aactttggcg tgagcaaggg cgaggagctg ttcaccgggg tggtgcccat   2520
cctggtcgag ctggacggcg acgtaaacgg ccacaagttc agcgtgtccg gcgagggcga   2580
gggcgatgcc acctacggca agctgaccct gaagttcatc tgcaccaccg gcaagctgcc   2640
cgtgccctgg cccacccteg tgaccaccct gacctacggc gtgcagtgct tcagccgcta   2700
ccccgaccac atgaagcagc acgacttctt caagtccgcc atgcccgaag gctacgtcca   2760
ggagcgcacc atcttcttca aggacgacgg caactacaag acccgcgccg aggtgaagtt   2820
cgagggcgac accctggtga accgcatcga gctgaagggc atcgacttca aggaggacgg   2880
caacatcctg gggcacaagc tggagtacaa ctacaacagc cacaacgtct atatcatggc   2940
cgacaagcag aagaacggca tcaaggtgaa cttcaagatc cgccacaaca tcgaggacgg   3000
cagcgtgcag ctcgccgacc actaccagca gaacaccccc atcggcgacg gccccgtgct   3060
gctgcccgac aaccactacc tgagcaccca gtccgccctg agcaaagacc ccaacgagaa   3120
gcgcgatcac atggtcctgc tggagttcgt gaccgccgcc gggatcactc tcggcatgga   3180
cgagctgtac aagaagttgt tcactcagac catgaaaggc gtggaacgcc tggccgtcat   3240
gggagacacc gcctgggatt tcagctccgc tggagggttc ttcacttcgg ttgggaaagg   3300
aattcatacg gtgtttggct ctgcctttca ggggctattt ggcggcttga actggataac   3360
aaaggtcatc atggggcgg tacttatatg gttggcatc aacacaagaa acatgacaat   3420
gtccatgagc atgatcttgg taggagtgat catgatgttt ttgtctctag agttggcgc   3480 cgatcaagga tgcgccatca actttggcaa gagagagctc aagtgcggag atggtatctt   3540
catatttaga gactctgatg actggctgaa caagtactca tactatccag aagatcctgt   3600
gaagcttgca tcaatagtga aagcctcttt cgaagaaggg aagtgtggcc taaattcagt   3660
tgactccctt gagcatgaga tgtggagaag cagggcagat gagattaata ccattttttga  3720 ggaaaacgag gtggacattt ctgttgtcgt gcaggatcca aagaatgttt accagagagg   3780
aactcatcca ttttccagaa ttcgggatgg tctgcagtat ggttggaaga cttggggtaa   3840
gaaccttgtg ttctccccag ggaggaagaa tggaagcttc atcatagatg gaaagtccag   3900
gaaagaatgc ccgttttcaa accgggtctg gaattctttc cagatagagg agtttgggac   3960
gggagtgttc accacacgcg tgtacatgga cgcagtcttt gaatacacca tagactgcga   4020
tggatctatc ttgggtgcag cggtgaacgg aaaaaagagt gcccatggct ctccaacatt   4080
ttggatggga agtcatgaag taaatgggac atgatgatc acaccttgg aggcattaga   4140 ttacaaggag tgtgagtggc cactgacaca tacgattgga acatcagttg aagagagtga   4200
aatgttcatg ccgagatcaa tcggaggccc agttagctct cacaatcata tccctggata   4260
caaggttcag acgaacggac cttggatgca ggtaccacta gaagtgaaga gagaagcttg   4320
cccagggact agcgtgatca ttgatggcaa ctgtgatgga cggggaaaat caaccagatc   4380
caccacggat agcgggaaag ttattcctga atggtgttgc cgctcctgca caatgccgcc   4440
tgtgagcttc catggtagtg atgggtgttg gtatcccatg gaaattaggc caaggaaaac   4500
gcatgaaagc catctggtgc gctcctgggt tacagctgga gaaatacatg ctgtccettt   4560
```

-continued

```
tggtttggtg agcatgatga tagcaatgga agtggtccta aggaaaagac agggaccaaa    4620
gcaaatgttg gttggaggag tagtgctctt gggagcaatg ctggtcgggc aagtaactct    4680
ccttgatttg ctgaaactca cagtggctgt gggattgcat ttccatgaga tgaacaatgg    4740
aggagacgcc atgtatatgg cgttgattgc tgccttttca atcagaccag ggctgctcat    4800
cggctttggg ctcaggaccc tatggagccc tcgggaacgc cttgtgctga ccctaggagc    4860
agccatggtg gagattgcct tgggtggcgt gatgggcggc ctgtggaagt atctaaatgc    4920
agtttctctc tgcatcctga caataaatgc tgttgcttct aggaaagcat caaataccat    4980
cttgcccctc atggctctgt tgacacctgt cactatggct gaggtgagac ttgccgcaat    5040 gttctttttgt gccatggtta tcatagggdt ccttcaccag aatttcaagg acacctccat    5100
gcagaagact atacctctgg tggccctcac actcacatct tacctgggct tgacacaacc    5160
ttttttgggc ctgtgtgcat ttctggcaac ccgcatattt gggcgaagga gtatcccagt    5220
gaatgaggca ctcgcagcag ctggtctagt gggagtgctg gcaggactgg cttttcagga    5280
gatggagaac ttccttggtc cgattgcagt tggaggactc ctgatgatgc tggttagcgt    5340
ggctgggagg gtggatgggc tagagctcaa gaagcttggt gaagtttcat gggaagagga    5400
ggcggagatc agcgggagtt ccgcccgcta tgatgtggca ctcagtgaac aagggagtt    5460 caagctgctt tctgaagaga aagtgccatg ggaccaggtt gtgatgacct cgctggcctt    5520
ggttggggct gccctccatc catttgctct tctgctggtc cttgctgggt ggctgtttca    5580
tgtcagggga gctaggagaa gtggggatgt cttgtgggat attcccactc ctaagatcat    5640
cgaggaatgt gaacatctgg aggatgggat ttatggcata ttccagtcaa ccttcttggg    5700
ggcctcccag cgaggagtgg gagtggcaca gggaggggtg ttccacacaa tgtggcatgt    5760
cacaagagga gctttccttg tcaggaatgg caagaagttg attccatctt gggcttcagt    5820
aaaggaagac cttgtcgcct atggtggctc atggaagttg gaaggcagat gggatggaga    5880
ggaagaggtc cagttgatcg cggctgttcc aggaaagaac gtggtcaacg tccagacaaa    5940
accgagcttg ttcaaagtga ggaatggggg agaaatcggg gctgtcgctc ttgactatcc    6000
gagtggcact tcaggatctc ctattgttaa caggaacgga gaggtgattg ggctgtacgg    6060
caatggcatc cttgtcggtg acaactcctt cgtgtccgcc atatcccaga ctgaggtgaa    6120
ggaagaagga aaggaggagc tccaagagat cccgacaatg ctaaagaaag aatgacaac    6180 tgtccttgat tttcatcctg gagctgggaa gacaagacgt ttcctcccac agatcttggc    6240
cgagtgcgca cggagacgct gccgcactct tgtgttggcc cccaccaggg ttgttctttc    6300
tgaaatgaag gaggcttttc acggcctgga cgtgaaattc cacacacagg ctttttccgc    6360
tcacggcagc gggagagaag tcattgatgc catgtgccat gccaccctaa cttacaggat    6420
gttggaacca actagggttg ttaactggga agtgatcatt atggatgaag cccatttttt    6480
ggatccagct agcatagccg ctagaggttg gcagcgcac agagctaggg caaatgaaag    6540
tgcaacaatc ttgatgacag ccacaccgcc tgggactagt gatgaatttc cacattcaaa    6600
tggtgaaata gaagatgttc aaacggacat acccagtgag ccctggaaca cagggcatga    6660
ctggatcctg gctgacaaaa ggcccacggc atggttcctt ccatccatca gagctgcaaa    6720
tgtcatggct gcctctttgc gtaaggctgg aaagagtgtg gtggtcctga acaggaaaac    6780
ctttgagaga gaatacccca cgataaagca gaagaaacct gactttatat tggccactga    6840
catagctgaa atgggagcca acctttgcgt ggagcgagtg ctggattgca ggacggcttt    6900
```

| | |
|---|---|
| taagcctgtg cttgtggatg aagggaggaa ggtggcaata aaagggccac ttcgtatctc | 6960 |
| cgcatcctct gctgctcaaa ggaggggcg cattgggaga atcccaaca gagatggaga | 7020 |
| ctcatactac tattctgagc ctacaagtga aaataatgcc caccacgtct gctggttgga | 7080 |
| ggcctcaatg ctcttggaca acatggaggt gaggggtgga atggtcgccc cactctatgg | 7140 |
| cgttgaagga actaaaacac cagtttcccc tggtgaaatg agactgaggg atgaccagag | 7200 |
| gaaagtcttc agagaactag tgaggaattg tgacctgccc gtttggcttt cgtggcaagt | 7260 |
| ggccaaggct ggtttgaaga cgaatgatcg taagtggtgt tttgaaggcc ctgaggaaca | 7320 |
| tgagatcttg aatgacagcg gtgaaacagt gaagtgcagg gctcctggag gagcaaagaa | 7380 |
| gcctctgcgc ccaaggtggt gtgatgaaag ggtgtcatct gaccagagtg cgctgtctga | 7440 |
| atttattaag tttgctgaag gtaggagggg agctgctgaa gtgctagttg tgctgagtga | 7500 |
| actccctgat ttcctggcta aaaaaggtgg agaggcaatg gataccatca gtgtgttcct | 7560 |
| ccactctgag gaaggctcta gggcttaccg caatgcacta tcaatgatgc ctgaggcaat | 7620 |
| gacaatagtc atgctgttta tactggctgg actactgaca tcgggaatgg tcatctttt | 7680 |
| catgtctccc aaaggcatca gtagaatgtc tatggcgatg ggcacaatgg ccggctgtgg | 7740 |
| atatctcatg ttccttggag gcgtcaaacc cactcacatc tcctatgtca tgctcatatt | 7800 |
| ctttgtcctg atggtggttg tgatccccga gccagggcaa caaaggtcca tccaagacaa | 7860 |
| ccaagtggca tacctcatta ttggcatcct gacgctggtt tcagcggtgg cagccaacga | 7920 |
| gctaggcatg ctggagaaaa ccaaagagga cctctttggg aagaagaact taattccatc | 7980 |
| tagtgcttca ccctggagtt ggccggatct tgacctgaag ccaggagctg cctggacagt | 8040 |
| gtacgttggc attgttacaa tgctctctcc aatgttgcac cactggatca agtcgaata | 8100 |
| tggcaacctg tctctgtctg aatagcccca gtcagcctca gtccttctt tcatggacaa | 8160 |
| ggggatacca ttcatgaaga tgaatatctc ggtcataatg ctgctggtca gtggctggaa | 8220 |
| ttcaataaca gtgatgcctc tgctctgtgg catagggtgc gccatgctcc actggtctct | 8280 |
| cattttacct ggaatcaaag cgcagcagtc aaagcttgca cagagaaggg tgttccatgg | 8340 |
| cgttgccaag aaccctgtgg ttgatgggaa tccaacagtt gacattgagg aagctcctga | 8400 |
| aatgcctgcc ctttatgaga agaaactggc tctatatctc cttcttgctc tcagcctagc | 8460 |
| ttctgttgcc atgtgcagaa cgcccttttc attggctgaa ggcattgtcc tagcatcagc | 8520 |
| tgccttaggg ccgctcatag agggaaacac cagccttctt tggaatggac ccatggctgt | 8580 |
| ctccatgaca ggagtcatga gggggaatca ctatgctttt gtgggagtca tgtacaatct | 8640 |
| atggaagatg aaaactggac gccggggag cgcgaatgga aaaactttgg gtgaagtctg | 8700 |
| gaagagggaa ctgaatctgt tggacaagcg acagtttgag ttgtataaaa ggaccgacat | 8760 |
| tgtggaggtg gatcgtgata cggcacgcag gcatttggcc gaagggaagg tggacaccgg | 8820 |
| ggtggcggtc tccaggggga ccgcaaagtt aaggtggttc catgagcgtg ctatgtcaa | 8880 |
| gctggaaggt agggtgattg acctgggtg tggccgcgga gctggtgtt actacgctgc | 8940 |
| tgcgcaaaag gaagtgagtg gggtcaaagg atttactctt ggaagagacg gccatgagaa | 9000 |
| acccatgaat gtgcaaagtc tgggatggaa catcatcacc ttcaaggaca aaactgatat | 9060 |
| ccaccgccta gaaccagtga atgtgacac ccttttgtgt gacattggag agtcatcatc | 9120 |
| gtcatcggtc acagaggggg aaaggaccgt gagagttctt gatactgtag aaaaatggct | 9180 |
| ggcttgtggg gttgacaact tctgtgtgaa ggtgttagct ccatacatgc cagatgttct | 9240 |
| tgagaaactg gaattgctcc aaaggaggtt tggcggaaca gtgatcagga accctctctc | 9300 |

```
caggaattcc actcatgaaa tgtactacgt gtctggagcc cgcagcaatg tcacatttac    9360
tgtgaaccaa acatcccgcc tcctgatgag gagaatgagg cgtccaactg gaaaagtgac    9420
cctggaggct gacgtcatcc tcccaattgg gacacgcagt gttgagacag acaagggacc    9480
cctggacaaa gaggccatag aagaaagggt tgagaggata aaatctgagt acatgacctc    9540
ttggttttat gacaatgaca accccctacag gacctggcac tactgtggct cctatgtcac    9600
aaaaacctca ggaagtgcgg cgagcatggt aaatggtgtt attaaaattc tgacatatcc    9660
atgggacagg atagaggagg tcaccagaat ggcaatgact gacacaaccc cttttggaca    9720
gcaaagagtg tttaaagaaa aagttgacac cagagcaaag gatccaccag cgggaactag    9780
gaagatcatg aaagttgtca acaggtggct gttccgccac ctggccagag aaaagagccc    9840
cagactgtgc acaaaggaag aatttattgc aaaagtccga agtcatgcag ccattggagc    9900
ttacctggaa gaacaagaac agtggaagac tgccaatgag gctgtccaag acccaaagtt    9960
ctgggaactg gtggatgaag aaaggaagct gcaccaacaa ggcaggtgtc ggacttgtgt   10020
gtacaacatg atggggaaaa gagagaagaa gctgtcagag tttgggaaag caaagggaag   10080
ccgtgccata tggtatatgt ggctgggagc gcggtatctt gagtttgagg ccctgggatt   10140
cctgaatgag gaccattggg cttccaggga aaactcagga ggaggagtgg aaggcattgg   10200
cttacaatac ctaggatatg tgatcagaga cctggctgca atggatggtg gtggattcta   10260
cgcggatgac accgctggat gggacacgcg catcacagag gcagaccttg atgatgaaca   10320
ggagatcttg aactcatgag cccacatca caaaaaactg gcacaagcag tgatggaaat   10380
gacatacaag aacaaagtgg tgaaagtgtt gagaccagcc ccaggaggga aagcctacat   10440
ggatgtcata agtcgacgag accagagagg atccgggcag gtagtgactt atgctctgaa   10500
caccatcacc aacttgaaag tccaattgat cagaatggca gaagcagaga tggtgataca   10560
tcaccaacat gttcaagatt gtgatgaatc agttctgacc aggctggagg catggctcac   10620
tgagcacgga tgtaacagac tgaagaggat ggcggtgagt ggagacgact gtgtggtccg   10680
gcccatcgat gacaggttcg gcctggcccct gtcccatctc aacgccatgt ccaaggttag   10740
aaaggacata tctgaatggc agccatcaaa agggtggaat gattgggaga atgtgccctt   10800
ctgttcccac cacttccatg aactacagct gaaggatggc aggaggattg tggtgccttg   10860
ccgagaacag gacgagctca ttgggagagg aagggtgtct ccaggaaacg gctggatgat   10920
caaggaaaca gcttgcctca gcaaagccta tgccaacatg tggtcactga tgtattttca   10980
caaaagggac atgaggctac tgtcattggc tgtttcctca gctgttccca cctcatgggt   11040
tccacaagga cgcacaacat ggtcgattca tgggaaaggg gagtggatga ccacggaaga   11100
catgcttgag gtgtggaaca gagtatggat aaccaacaac ccacacatgc aggacaagac   11160
aatggtgaaa aaatggagag atgtcccctta tctaaccaag agacaagaca agctgtgcgg   11220
atcactgatt ggaatgacca ataggggccac ctgggcctcc cacatccatt tagtcatcca   11280
tcgtatccga acgctgattg acaggagaaa atacactgac tacctaacag tcatggacag   11340
gtattctgtg gatgctgacc tgcaactggg tgagcttatc tgaaacacca tctaacagga   11400
ataaccggga tacaaaccac gggtggagaa ccggactccc cacaacctga accgggata    11460 taaaccacgg ctggagaacc gggctccgca cttaaaatga aacagaaacc gggataaaaa   11520 ctacggatg agaaccggac tccacacatt gagacagaag aagttgtcag cccagaaccc   11580
cacacgagtt ttgccactgc taagctgtga ggcagtgcag gctgggacag ccgacctcca   11640
```

```
ggttgcgaaa aacctggttt ctgggacctc ccaccccaga gtaaaagaa cggagcctcc    11700 gctaccaccc tcccacgtgg tggtagaaag acggggtcta gaggttagag gagaccctcc    11760
agggaacaaa tagtgggacc atattgacgc cagggaaaga ccggagtggt tctctgcttt    11820
tcctccagag gtctgtgagc acagtttgct caagaataag cagacctttg gatgacaaac    11880
acaaaaccac                                                           11890
```

<210> SEQ ID NO 14
<211> LENGTH: 3754
<212> TYPE: PRT
<213> ORGANISM: recombinant yellow fever virus

<400> SEQUENCE: 14

```
Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Val Ala Ser Leu Met Arg Gly Leu Ser
                85                  90                  95

Ser Arg Lys Arg Arg Ser His Asp Val Leu Thr Val Gln Phe Leu Ile
            100                 105                 110

Leu Gly Met Leu Leu Met Thr Gly Gly Val Thr Leu Val Arg Lys Asn
        115                 120                 125

Arg Trp Leu Leu Leu Asn Val Thr Ser Glu Asp Leu Gly Lys Thr Phe
    130                 135                 140

Ser Val Gly Thr Gly Asn Cys Thr Thr Asn Ile Leu Glu Ala Lys Tyr
145                 150                 155                 160

Trp Cys Pro Asp Ser Met Glu Tyr Asn Cys Pro Asn Leu Ser Pro Arg
                165                 170                 175

Glu Glu Pro Asp Asp Ile Asp Cys Trp Cys Tyr Gly Val Glu Asn Val
            180                 185                 190

Arg Val Ala Tyr Gly Lys Cys Asp Ser Ala Gly Arg Ser Arg Arg Ser
        195                 200                 205

Arg Arg Ala Ile Asp Leu Pro Thr His Glu Asn His Gly Leu Lys Thr
    210                 215                 220

Arg Gln Glu Lys Trp Met Thr Gly Arg Met Gly Glu Arg Gln Leu Gln
225                 230                 235                 240

Lys Ile Glu Arg Trp Phe Val Arg Asn Pro Phe Phe Ala Val Thr Ala
                245                 250                 255

Leu Thr Ile Ala Tyr Leu Val Gly Ser Asn Met Thr Gln Arg Val Val
            260                 265                 270

Ile Ala Leu Leu Val Leu Ala Val Gly Pro Ala Tyr Ser Ala His Cys
        275                 280                 285

Ile Gly Ile Thr Asp Arg Asp Phe Ile Glu Gly Val His Gly Gly Thr
    290                 295                 300

Trp Val Ser Ala Thr Leu Glu Gln Asp Lys Cys Val Thr Val Met Ala
305                 310                 315                 320

Pro Asp Lys Pro Ser Leu Asp Ile Ser Leu Glu Thr Val Ala Ile Asp
```

```
                    325                 330                 335
Arg Pro Ala Glu Val Arg Lys Val Cys Tyr Asn Ala Val Leu Thr His
                340                 345                 350
Val Lys Ile Asn Asp Lys Cys Pro Ser Thr Gly Glu Ala His Leu Ala
                355                 360                 365
Glu Glu Asn Glu Gly Asp Asn Ala Cys Lys Arg Thr Tyr Ser Asp Arg
                370                 375                 380
Gly Trp Gly Asn Gly Cys Gly Leu Phe Gly Lys Gly Ser Ile Val Ala
385                 390                 395                 400
Cys Ala Lys Phe Thr Cys Ala Lys Ser Met Ser Leu Phe Glu Val Asp
                405                 410                 415
Gln Thr Lys Ile Gln Tyr Val Ile Arg Ala Gln Leu His Val Gly Ala
                420                 425                 430
Lys Gln Glu Asn Trp Asn Thr Ser Ile Lys Thr Leu Lys Phe Asp Ala
                435                 440                 445
Leu Ser Gly Ser Gln Glu Val Glu Phe Ile Gly Tyr Gly Lys Ala Thr
450                 455                 460
Leu Glu Cys Gln Val Gln Thr Ala Val Asp Phe Gly Asn Ser Tyr Ile
465                 470                 475                 480
Ala Glu Met Asp Ile Glu Ser Trp Ile Val Asp Arg Gln Trp Ala Gln
                485                 490                 495
Asp Leu Thr Leu Pro Trp Gln Ser Gly Ser Gly Gly Val Trp Arg Glu
                500                 505                 510
Met His His Leu Val Glu Phe Glu Pro Pro His Ala Ala Thr Ile Arg
                515                 520                 525
Val Leu Ala Leu Gly Asn Gln Glu Gly Ser Leu Lys Thr Ala Leu Thr
                530                 535                 540
Gly Ala Met Arg Val Thr Lys Asp Thr Asn Asp Asn Leu Tyr Lys Leu
545                 550                 555                 560
Leu His Gly Gly His Val Ser Cys Arg Val Lys Leu Ser Ala Leu Thr
                565                 570                 575
Leu Lys Gly Thr Ser Tyr Lys Ile Cys Thr Asp Lys Met Phe Phe Val
                580                 585                 590
Lys Asn Pro Thr Asp Thr Gly His Gly Thr Val Val Met Gln Val Lys
                595                 600                 605
Val Ser Lys Gly Thr Pro Cys Arg Ile Pro Val Ile Val Ala Asp Asp
                610                 615                 620
Leu Thr Ala Ala Ile Asn Lys Gly Ile Leu Val Thr Val Asn Pro Ile
625                 630                 635                 640
Ala Ser Thr Asn Asp Asp Glu Val Leu Ile Glu Val Asn Pro Pro Phe
                645                 650                 655
Gly Asp Ser Tyr Ile Ile Val Gly Arg Gly Asp Ser Arg Leu Thr Tyr
                660                 665                 670
Gln Trp His Lys Glu Gly Ser Ser Ile Gly Lys Leu Phe Thr Gln Thr
                675                 680                 685
Met Lys Gly Val Glu Arg Leu Ala Val Met Gly Asp Thr Ala Trp Asp
                690                 695                 700
Phe Ser Ser Ala Gly Gly Phe Phe Thr Ser Val Gly Lys Gly Ile His
705                 710                 715                 720
Thr Val Phe Gly Ser Ala Phe Gln Gly Leu Phe Gly Gly Leu Asn Trp
                725                 730                 735
Ile Thr Lys Val Ile Met Gly Ala Val Leu Ile Trp Val Gly Ile Asn
                740                 745                 750
```

```
Thr Arg Asn Met Thr Met Ser Met Ser Met Ile Leu Val Gly Val Ile
        755                 760                 765

Met Met Phe Leu Ser Leu Gly Val Gly Ala Asp Gln Gly Cys Ala Ile
    770                 775                 780

Asn Phe Gly Val Ser Lys Gly Glu Glu Leu Phe Thr Gly Val Val Pro
785                 790                 795                 800

Ile Leu Val Glu Leu Asp Gly Asp Val Asn Gly His Lys Phe Ser Val
                805                 810                 815

Ser Gly Glu Gly Glu Gly Asp Ala Thr Tyr Gly Lys Leu Thr Leu Lys
                820                 825                 830

Phe Ile Cys Thr Thr Gly Lys Leu Pro Val Pro Trp Pro Thr Leu Val
            835                 840                 845

Thr Thr Leu Thr Tyr Gly Val Gln Cys Phe Ser Arg Tyr Pro Asp His
    850                 855                 860

Met Lys Gln His Asp Phe Phe Lys Ser Ala Met Pro Glu Gly Tyr Val
865                 870                 875                 880

Gln Glu Arg Thr Ile Phe Phe Lys Asp Asp Gly Asn Tyr Lys Thr Arg
                885                 890                 895

Ala Glu Val Lys Phe Glu Gly Asp Thr Leu Val Asn Arg Ile Glu Leu
                900                 905                 910

Lys Gly Ile Asp Phe Lys Glu Asp Gly Asn Ile Leu Gly His Lys Leu
            915                 920                 925

Glu Tyr Asn Tyr Asn Ser His Asn Val Tyr Ile Met Ala Asp Lys Gln
    930                 935                 940

Lys Asn Gly Ile Lys Val Asn Phe Lys Ile Arg His Asn Ile Glu Asp
945                 950                 955                 960

Gly Ser Val Gln Leu Ala Asp His Tyr Gln Gln Asn Thr Pro Ile Gly
                965                 970                 975

Asp Gly Pro Val Leu Leu Pro Asp Asn His Tyr Leu Ser Thr Gln Ser
                980                 985                 990

Ala Leu Ser Lys Asp Pro Asn Glu  Lys Arg Asp His Met  Val Leu Leu
            995                 1000                1005

Glu Phe  Val Thr Ala Ala Gly  Ile Thr Leu Gly Met  Asp Glu Leu
    1010                1015                1020

Tyr Lys  Lys Leu Phe Thr Gln  Thr Met Lys Gly Val  Glu Arg Leu
    1025                1030                1035

Ala Val  Met Gly Asp Thr Ala  Trp Asp Phe Ser Ser  Ala Gly Gly
    1040                1045                1050

Phe Phe  Thr Ser Val Gly Lys  Gly Ile His Thr Val  Phe Gly Ser
    1055                1060                1065

Ala Phe  Gln Gly Leu Phe Gly  Leu Asn Trp Ile  Thr Lys Val
    1070                1075                1080

Ile Met  Gly Ala Val Leu Ile  Trp Val Gly Ile Asn  Thr Arg Asn
    1085                1090                1095

Met Thr  Met Ser Met Ser Met  Ile Leu Val Gly Val  Ile Met Met
    1100                1105                1110

Phe Leu  Ser Leu Gly Val Gly  Ala Asp Gln Gly Cys  Ala Ile Asn
    1115                1120                1125

Phe Gly  Lys Arg Glu Leu Lys  Cys Gly Asp Gly Ile  Phe Ile Phe
    1130                1135                1140

Arg Asp  Ser Asp Asp Trp Leu  Asn Lys Tyr Ser Tyr  Tyr Pro Glu
    1145                1150                1155
```

```
Asp Pro Val Lys Leu Ala Ser Ile Val Lys Ala Ser Phe Glu Glu
    1160                1165                1170

Gly Lys Cys Gly Leu Asn Ser Val Asp Ser Leu Glu His Glu Met
    1175                1180                1185

Trp Arg Ser Arg Ala Asp Glu Ile Asn Thr Ile Phe Glu Glu Asn
    1190                1195                1200

Glu Val Asp Ile Ser Val Val Gln Asp Pro Lys Asn Val Tyr
    1205                1210                1215

Gln Arg Gly Thr His Pro Phe Ser Arg Ile Arg Asp Gly Leu Gln
    1220                1225                1230

Tyr Gly Trp Lys Thr Trp Gly Lys Asn Leu Val Phe Ser Pro Gly
    1235                1240                1245

Arg Lys Asn Gly Ser Phe Ile Ile Asp Gly Lys Ser Arg Lys Glu
    1250                1255                1260

Cys Pro Phe Ser Asn Arg Val Trp Asn Ser Phe Gln Ile Glu Glu
    1265                1270                1275

Phe Gly Thr Gly Val Phe Thr Thr Arg Val Tyr Met Asp Ala Val
    1280                1285                1290

Phe Glu Tyr Thr Ile Asp Cys Asp Gly Ser Ile Leu Gly Ala Ala
    1295                1300                1305

Val Asn Gly Lys Lys Ser Ala His Gly Ser Pro Thr Phe Trp Met
    1310                1315                1320

Gly Ser His Glu Val Asn Gly Thr Trp Met Ile His Thr Leu Glu
    1325                1330                1335

Ala Leu Asp Tyr Lys Glu Cys Glu Trp Pro Leu Thr His Thr Ile
    1340                1345                1350

Gly Thr Ser Val Glu Glu Ser Glu Met Phe Met Pro Arg Ser Ile
    1355                1360                1365

Gly Gly Pro Val Ser Ser His Asn His Ile Pro Gly Tyr Lys Val
    1370                1375                1380

Gln Thr Asn Gly Pro Trp Met Gln Val Pro Leu Glu Val Lys Arg
    1385                1390                1395

Glu Ala Cys Pro Gly Thr Ser Val Ile Ile Asp Gly Asn Cys Asp
    1400                1405                1410

Gly Arg Gly Lys Ser Thr Arg Ser Thr Thr Asp Ser Gly Lys Val
    1415                1420                1425

Ile Pro Glu Trp Cys Cys Arg Ser Cys Thr Met Pro Pro Val Ser
    1430                1435                1440

Phe His Gly Ser Asp Gly Cys Trp Tyr Pro Met Glu Ile Arg Pro
    1445                1450                1455

Arg Lys Thr His Glu Ser His Leu Val Arg Ser Trp Val Thr Ala
    1460                1465                1470

Gly Glu Ile His Ala Val Pro Phe Gly Leu Val Ser Met Met Ile
    1475                1480                1485

Ala Met Glu Val Val Leu Arg Lys Arg Gln Gly Pro Lys Gln Met
    1490                1495                1500

Leu Val Gly Gly Val Val Leu Leu Gly Ala Met Leu Val Gly Gln
    1505                1510                1515

Val Thr Leu Leu Asp Leu Leu Lys Leu Thr Val Ala Val Gly Leu
    1520                1525                1530

His Phe His Glu Met Asn Asn Gly Gly Asp Ala Met Tyr Met Ala
    1535                1540                1545

Leu Ile Ala Ala Phe Ser Ile Arg Pro Gly Leu Leu Ile Gly Phe
```

-continued

```
                 1550                1555                1560

Gly  Leu  Arg  Thr  Leu  Trp  Ser  Pro  Arg  Glu  Arg  Leu  Val  Leu  Thr
                 1565                1570                1575

Leu  Gly  Ala  Ala  Met  Val  Glu  Ile  Ala  Leu  Gly  Gly  Val  Met  Gly
                 1580                1585                1590

Gly  Leu  Trp  Lys  Tyr  Leu  Asn  Ala  Val  Ser  Leu  Cys  Ile  Leu  Thr
                 1595                1600                1605

Ile  Asn  Ala  Val  Ala  Ser  Arg  Lys  Ala  Ser  Asn  Thr  Ile  Leu  Pro
                 1610                1615                1620

Leu  Met  Ala  Leu  Leu  Thr  Pro  Val  Thr  Met  Ala  Glu  Val  Arg  Leu
                 1625                1630                1635

Ala  Ala  Met  Phe  Phe  Cys  Ala  Met  Val  Ile  Ile  Gly  Val  Leu  His
                 1640                1645                1650

Gln  Asn  Phe  Lys  Asp  Thr  Ser  Met  Gln  Lys  Thr  Ile  Pro  Leu  Val
                 1655                1660                1665

Ala  Leu  Thr  Leu  Thr  Ser  Tyr  Leu  Gly  Leu  Thr  Gln  Pro  Phe  Leu
                 1670                1675                1680

Gly  Leu  Cys  Ala  Phe  Leu  Ala  Thr  Arg  Ile  Phe  Gly  Arg  Arg  Ser
                 1685                1690                1695

Ile  Pro  Val  Asn  Glu  Ala  Leu  Ala  Ala  Ala  Gly  Leu  Val  Gly  Val
                 1700                1705                1710

Leu  Ala  Gly  Leu  Ala  Phe  Gln  Glu  Met  Glu  Asn  Phe  Leu  Gly  Pro
                 1715                1720                1725

Ile  Ala  Val  Gly  Gly  Leu  Leu  Met  Met  Leu  Val  Ser  Val  Ala  Gly
                 1730                1735                1740

Arg  Val  Asp  Gly  Leu  Glu  Leu  Lys  Lys  Leu  Gly  Glu  Val  Ser  Trp
                 1745                1750                1755

Glu  Glu  Glu  Ala  Glu  Ile  Ser  Gly  Ser  Ser  Ala  Arg  Tyr  Asp  Val
                 1760                1765                1770

Ala  Leu  Ser  Glu  Gln  Gly  Glu  Phe  Lys  Leu  Leu  Ser  Glu  Glu  Lys
                 1775                1780                1785

Val  Pro  Trp  Asp  Gln  Val  Val  Met  Thr  Ser  Leu  Ala  Leu  Val  Gly
                 1790                1795                1800

Ala  Ala  Leu  His  Pro  Phe  Ala  Leu  Leu  Leu  Val  Leu  Ala  Gly  Trp
                 1805                1810                1815

Leu  Phe  His  Val  Arg  Gly  Ala  Arg  Arg  Ser  Gly  Asp  Val  Leu  Trp
                 1820                1825                1830

Asp  Ile  Pro  Thr  Pro  Lys  Ile  Ile  Glu  Glu  Cys  Glu  His  Leu  Glu
                 1835                1840                1845

Asp  Gly  Ile  Tyr  Gly  Ile  Phe  Gln  Ser  Thr  Phe  Leu  Gly  Ala  Ser
                 1850                1855                1860

Gln  Arg  Gly  Val  Gly  Val  Ala  Gln  Gly  Gly  Val  Phe  His  Thr  Met
                 1865                1870                1875

Trp  His  Val  Thr  Arg  Gly  Ala  Phe  Leu  Val  Arg  Asn  Gly  Lys  Lys
                 1880                1885                1890

Leu  Ile  Pro  Ser  Trp  Ala  Ser  Val  Lys  Glu  Asp  Leu  Val  Ala  Tyr
                 1895                1900                1905

Gly  Gly  Ser  Trp  Lys  Leu  Glu  Gly  Arg  Trp  Asp  Gly  Glu  Glu  Glu
                 1910                1915                1920

Val  Gln  Leu  Ile  Ala  Ala  Val  Pro  Gly  Lys  Asn  Val  Val  Asn  Val
                 1925                1930                1935

Gln  Thr  Lys  Pro  Ser  Leu  Phe  Lys  Val  Arg  Asn  Gly  Gly  Glu  Ile
                 1940                1945                1950
```

```
Gly Ala Val Ala Leu Asp Tyr Pro Ser Gly Thr Ser Gly Ser Pro
    1955                1960                1965

Ile Val Asn Arg Asn Gly Glu Val Ile Gly Leu Tyr Gly Asn Gly
    1970                1975                1980

Ile Leu Val Gly Asp Asn Ser Phe Val Ser Ala Ile Ser Gln Thr
    1985                1990                1995

Glu Val Lys Glu Glu Gly Lys Glu Glu Leu Gln Glu Ile Pro Thr
    2000                2005                2010

Met Leu Lys Lys Gly Met Thr Thr Val Leu Asp Phe His Pro Gly
    2015                2020                2025

Ala Gly Lys Thr Arg Arg Phe Leu Pro Gln Ile Leu Ala Glu Cys
    2030                2035                2040

Ala Arg Arg Arg Leu Arg Thr Leu Val Leu Ala Pro Thr Arg Val
    2045                2050                2055

Val Leu Ser Glu Met Lys Glu Ala Phe His Gly Leu Asp Val Lys
    2060                2065                2070

Phe His Thr Gln Ala Phe Ser Ala His Gly Ser Gly Arg Glu Val
    2075                2080                2085

Ile Asp Ala Met Cys His Ala Thr Leu Thr Tyr Arg Met Leu Glu
    2090                2095                2100

Pro Thr Arg Val Val Asn Trp Glu Val Ile Ile Met Asp Glu Ala
    2105                2110                2115

His Phe Leu Asp Pro Ala Ser Ile Ala Ala Arg Gly Trp Ala Ala
    2120                2125                2130

His Arg Ala Arg Ala Asn Glu Ser Ala Thr Ile Leu Met Thr Ala
    2135                2140                2145

Thr Pro Pro Gly Thr Ser Asp Glu Phe Pro His Ser Asn Gly Glu
    2150                2155                2160

Ile Glu Asp Val Gln Thr Asp Ile Pro Ser Glu Pro Trp Asn Thr
    2165                2170                2175

Gly His Asp Trp Ile Leu Ala Asp Lys Arg Pro Thr Ala Trp Phe
    2180                2185                2190

Leu Pro Ser Ile Arg Ala Ala Asn Val Met Ala Ala Ser Leu Arg
    2195                2200                2205

Lys Ala Gly Lys Ser Val Val Val Leu Asn Arg Lys Thr Phe Glu
    2210                2215                2220

Arg Glu Tyr Pro Thr Ile Lys Gln Lys Lys Pro Asp Phe Ile Leu
    2225                2230                2235

Ala Thr Asp Ile Ala Glu Met Gly Ala Asn Leu Cys Val Glu Arg
    2240                2245                2250

Val Leu Asp Cys Arg Thr Ala Phe Lys Pro Val Leu Val Asp Glu
    2255                2260                2265

Gly Arg Lys Val Ala Ile Lys Gly Pro Leu Arg Ile Ser Ala Ser
    2270                2275                2280

Ser Ala Ala Gln Arg Arg Gly Arg Ile Gly Arg Asn Pro Asn Arg
    2285                2290                2295

Asp Gly Asp Ser Tyr Tyr Tyr Ser Glu Pro Thr Ser Glu Asn Asn
    2300                2305                2310

Ala His His Val Cys Trp Leu Glu Ala Ser Met Leu Leu Asp Asn
    2315                2320                2325

Met Glu Val Arg Gly Gly Met Val Ala Pro Leu Tyr Gly Val Glu
    2330                2335                2340
```

```
Gly Thr Lys Thr Pro Val Ser Pro Gly Glu Met Arg Leu Arg Asp
2345                2350                2355

Asp Gln Arg Lys Val Phe Arg Glu Leu Val Arg Asn Cys Asp Leu
2360                2365                2370

Pro Val Trp Leu Ser Trp Gln Val Ala Lys Ala Gly Leu Lys Thr
2375                2380                2385

Asn Asp Arg Lys Trp Cys Phe Glu Gly Pro Glu Glu His Glu Ile
2390                2395                2400

Leu Asn Asp Ser Gly Glu Thr Val Lys Cys Arg Ala Pro Gly Gly
2405                2410                2415

Ala Lys Lys Pro Leu Arg Pro Arg Trp Cys Asp Glu Arg Val Ser
2420                2425                2430

Ser Asp Gln Ser Ala Leu Ser Glu Phe Ile Lys Phe Ala Glu Gly
2435                2440                2445

Arg Arg Gly Ala Ala Glu Val Leu Val Val Leu Ser Glu Leu Pro
2450                2455                2460

Asp Phe Leu Ala Lys Lys Gly Gly Glu Ala Met Asp Thr Ile Ser
2465                2470                2475

Val Phe Leu His Ser Glu Glu Gly Ser Arg Ala Tyr Arg Asn Ala
2480                2485                2490

Leu Ser Met Met Pro Glu Ala Met Thr Ile Val Met Leu Phe Ile
2495                2500                2505

Leu Ala Gly Leu Leu Thr Ser Gly Met Val Ile Phe Phe Met Ser
2510                2515                2520

Pro Lys Gly Ile Ser Arg Met Ser Met Ala Met Gly Thr Met Ala
2525                2530                2535

Gly Cys Gly Tyr Leu Met Phe Leu Gly Gly Val Lys Pro Thr His
2540                2545                2550

Ile Ser Tyr Val Met Leu Ile Phe Phe Val Leu Met Val Val Val
2555                2560                2565

Ile Pro Glu Pro Gly Gln Gln Arg Ser Ile Gln Asp Asn Gln Val
2570                2575                2580

Ala Tyr Leu Ile Ile Gly Ile Leu Thr Leu Val Ser Ala Val Ala
2585                2590                2595

Ala Asn Glu Leu Gly Met Leu Glu Lys Thr Lys Glu Asp Leu Phe
2600                2605                2610

Gly Lys Lys Asn Leu Ile Pro Ser Ser Ala Ser Pro Trp Ser Trp
2615                2620                2625

Pro Asp Leu Asp Leu Lys Pro Gly Ala Ala Trp Thr Val Tyr Val
2630                2635                2640

Gly Ile Val Thr Met Leu Ser Pro Met Leu His His Trp Ile Lys
2645                2650                2655

Val Glu Tyr Gly Asn Leu Ser Leu Ser Gly Ile Ala Gln Ser Ala
2660                2665                2670

Ser Val Leu Ser Phe Met Asp Lys Gly Ile Pro Phe Met Lys Met
2675                2680                2685

Asn Ile Ser Val Ile Met Leu Leu Val Ser Gly Trp Asn Ser Ile
2690                2695                2700

Thr Val Met Pro Leu Leu Cys Gly Ile Gly Cys Ala Met Leu His
2705                2710                2715

Trp Ser Leu Ile Leu Pro Gly Ile Lys Ala Gln Gln Ser Lys Leu
2720                2725                2730

Ala Gln Arg Arg Val Phe His Gly Val Ala Lys Asn Pro Val Val
```

|   |   |   |   |   |   |   |   |   |   |   |   |
|---|---|---|---|---|---|---|---|---|---|---|---|
|   | 2735 |   |   |   | 2740 |   |   |   | 2745 |   |   |
| Asp | Gly | Asn | Pro | Thr | Val | Asp | Ile | Glu | Glu | Ala | Pro | Glu | Met | Pro |
|   | 2750 |   |   |   | 2755 |   |   |   | 2760 |   |   |
| Ala | Leu | Tyr | Glu | Lys | Lys | Leu | Ala | Leu | Tyr | Leu | Leu | Leu | Ala | Leu |
|   | 2765 |   |   |   | 2770 |   |   |   | 2775 |   |   |
| Ser | Leu | Ala | Ser | Val | Ala | Met | Cys | Arg | Thr | Pro | Phe | Ser | Leu | Ala |
|   | 2780 |   |   |   | 2785 |   |   |   | 2790 |   |   |
| Glu | Gly | Ile | Val | Leu | Ala | Ser | Ala | Ala | Leu | Gly | Pro | Leu | Ile | Glu |
|   | 2795 |   |   |   | 2800 |   |   |   | 2805 |   |   |
| Gly | Asn | Thr | Ser | Leu | Leu | Trp | Asn | Gly | Pro | Met | Ala | Val | Ser | Met |
|   | 2810 |   |   |   | 2815 |   |   |   | 2820 |   |   |
| Thr | Gly | Val | Met | Arg | Gly | Asn | His | Tyr | Ala | Phe | Val | Gly | Val | Met |
|   | 2825 |   |   |   | 2830 |   |   |   | 2835 |   |   |
| Tyr | Asn | Leu | Trp | Lys | Met | Lys | Thr | Gly | Arg | Arg | Gly | Ser | Ala | Asn |
|   | 2840 |   |   |   | 2845 |   |   |   | 2850 |   |   |
| Gly | Lys | Thr | Leu | Gly | Glu | Val | Trp | Lys | Arg | Glu | Leu | Asn | Leu | Leu |
|   | 2855 |   |   |   | 2860 |   |   |   | 2865 |   |   |
| Asp | Lys | Arg | Gln | Phe | Glu | Leu | Tyr | Lys | Arg | Thr | Asp | Ile | Val | Glu |
|   | 2870 |   |   |   | 2875 |   |   |   | 2880 |   |   |
| Val | Asp | Arg | Asp | Thr | Ala | Arg | Arg | His | Leu | Ala | Glu | Gly | Lys | Val |
|   | 2885 |   |   |   | 2890 |   |   |   | 2895 |   |   |
| Asp | Thr | Gly | Val | Ala | Val | Ser | Arg | Gly | Thr | Ala | Lys | Leu | Arg | Trp |
|   | 2900 |   |   |   | 2905 |   |   |   | 2910 |   |   |
| Phe | His | Glu | Arg | Gly | Tyr | Val | Lys | Leu | Glu | Gly | Arg | Val | Ile | Asp |
|   | 2915 |   |   |   | 2920 |   |   |   | 2925 |   |   |
| Leu | Gly | Cys | Gly | Arg | Gly | Gly | Trp | Cys | Tyr | Tyr | Ala | Ala | Ala | Gln |
|   | 2930 |   |   |   | 2935 |   |   |   | 2940 |   |   |
| Lys | Glu | Val | Ser | Gly | Val | Lys | Gly | Phe | Thr | Leu | Gly | Arg | Asp | Gly |
|   | 2945 |   |   |   | 2950 |   |   |   | 2955 |   |   |
| His | Glu | Lys | Pro | Met | Asn | Val | Gln | Ser | Leu | Gly | Trp | Asn | Ile | Ile |
|   | 2960 |   |   |   | 2965 |   |   |   | 2970 |   |   |
| Thr | Phe | Lys | Asp | Lys | Thr | Asp | Ile | His | Arg | Leu | Glu | Pro | Val | Lys |
|   | 2975 |   |   |   | 2980 |   |   |   | 2985 |   |   |
| Cys | Asp | Thr | Leu | Leu | Cys | Asp | Ile | Gly | Glu | Ser | Ser | Ser | Ser | Ser |
|   | 2990 |   |   |   | 2995 |   |   |   | 3000 |   |   |
| Val | Thr | Glu | Gly | Glu | Arg | Thr | Val | Arg | Val | Leu | Asp | Thr | Val | Glu |
|   | 3005 |   |   |   | 3010 |   |   |   | 3015 |   |   |
| Lys | Trp | Leu | Ala | Cys | Gly | Val | Asp | Asn | Phe | Cys | Val | Lys | Val | Leu |
|   | 3020 |   |   |   | 3025 |   |   |   | 3030 |   |   |
| Ala | Pro | Tyr | Met | Pro | Asp | Val | Leu | Glu | Lys | Leu | Glu | Leu | Leu | Gln |
|   | 3035 |   |   |   | 3040 |   |   |   | 3045 |   |   |
| Arg | Arg | Phe | Gly | Gly | Thr | Val | Ile | Arg | Asn | Pro | Leu | Ser | Arg | Asn |
|   | 3050 |   |   |   | 3055 |   |   |   | 3060 |   |   |
| Ser | Thr | His | Glu | Met | Tyr | Tyr | Val | Ser | Gly | Ala | Arg | Ser | Asn | Val |
|   | 3065 |   |   |   | 3070 |   |   |   | 3075 |   |   |
| Thr | Phe | Thr | Val | Asn | Gln | Thr | Ser | Arg | Leu | Leu | Met | Arg | Arg | Met |
|   | 3080 |   |   |   | 3085 |   |   |   | 3090 |   |   |
| Arg | Arg | Pro | Thr | Gly | Lys | Val | Thr | Leu | Glu | Ala | Asp | Val | Ile | Leu |
|   | 3095 |   |   |   | 3100 |   |   |   | 3105 |   |   |
| Pro | Ile | Gly | Thr | Arg | Ser | Val | Glu | Thr | Asp | Lys | Gly | Pro | Leu | Asp |
|   | 3110 |   |   |   | 3115 |   |   |   | 3120 |   |   |
| Lys | Glu | Ala | Ile | Glu | Glu | Arg | Val | Glu | Arg | Ile | Lys | Ser | Glu | Tyr |
|   | 3125 |   |   |   | 3130 |   |   |   | 3135 |   |   |

```
Met Thr Ser Trp Phe Tyr Asp Asn Asp Asn Pro Tyr Arg Thr Trp
3140                3145                3150

His Tyr Cys Gly Ser Tyr Val Thr Lys Thr Ser Gly Ser Ala Ala
3155                3160                3165

Ser Met Val Asn Gly Val Ile Lys Ile Leu Thr Tyr Pro Trp Asp
3170                3175                3180

Arg Ile Glu Glu Val Thr Arg Met Ala Met Thr Asp Thr Thr Pro
3185                3190                3195

Phe Gly Gln Gln Arg Val Phe Lys Glu Lys Val Asp Thr Arg Ala
3200                3205                3210

Lys Asp Pro Pro Ala Gly Thr Arg Lys Ile Met Lys Val Val Asn
3215                3220                3225

Arg Trp Leu Phe Arg His Leu Ala Arg Glu Lys Ser Pro Arg Leu
3230                3235                3240

Cys Thr Lys Glu Glu Phe Ile Ala Lys Val Arg Ser His Ala Ala
3245                3250                3255

Ile Gly Ala Tyr Leu Glu Glu Gln Glu Gln Trp Lys Thr Ala Asn
3260                3265                3270

Glu Ala Val Gln Asp Pro Lys Phe Trp Glu Leu Val Asp Glu Glu
3275                3280                3285

Arg Lys Leu His Gln Gln Gly Arg Cys Arg Thr Cys Val Tyr Asn
3290                3295                3300

Met Met Gly Lys Arg Glu Lys Lys Leu Ser Glu Phe Gly Lys Ala
3305                3310                3315

Lys Gly Ser Arg Ala Ile Trp Tyr Met Trp Leu Gly Ala Arg Tyr
3320                3325                3330

Leu Glu Phe Glu Ala Leu Gly Phe Leu Asn Glu Asp His Trp Ala
3335                3340                3345

Ser Arg Glu Asn Ser Gly Gly Gly Val Glu Gly Ile Gly Leu Gln
3350                3355                3360

Tyr Leu Gly Tyr Val Ile Arg Asp Leu Ala Ala Met Asp Gly Gly
3365                3370                3375

Gly Phe Tyr Ala Asp Asp Thr Ala Gly Trp Asp Thr Arg Ile Thr
3380                3385                3390

Glu Ala Asp Leu Asp Asp Glu Gln Glu Ile Leu Asn Tyr Met Ser
3395                3400                3405

Pro His His Lys Lys Leu Ala Gln Ala Val Met Glu Met Thr Tyr
3410                3415                3420

Lys Asn Lys Val Val Lys Val Leu Arg Pro Ala Pro Gly Gly Lys
3425                3430                3435

Ala Tyr Met Asp Val Ile Ser Arg Arg Asp Gln Arg Gly Ser Gly
3440                3445                3450

Gln Val Val Thr Tyr Ala Leu Asn Thr Ile Thr Asn Leu Lys Val
3455                3460                3465

Gln Leu Ile Arg Met Ala Glu Ala Glu Met Val Ile His His Gln
3470                3475                3480

His Val Gln Asp Cys Asp Glu Ser Val Leu Thr Arg Leu Glu Ala
3485                3490                3495

Trp Leu Thr Glu His Gly Cys Asn Arg Leu Lys Arg Met Ala Val
3500                3505                3510

Ser Gly Asp Asp Cys Val Val Arg Pro Ile Asp Asp Arg Phe Gly
3515                3520                3525
```

| | | | | | | | | | | |
|---|---|---|---|---|---|---|---|---|---|---|
| Leu | Ala | Leu | Ser | His | Leu | Asn | Ala | Met | Ser | Lys | Val | Arg | Lys | Asp |
| | | | 3530 | | | | 3535 | | | | 3540 | | | |

Ile Ser Glu Trp Gln Pro Ser Lys Gly Trp Asn Asp Trp Glu Asn
3545                3550                3555

Val Pro Phe Cys Ser His His Phe His Glu Leu Gln Leu Lys Asp
3560                3565                3570

Gly Arg Arg Ile Val Val Pro Cys Arg Glu Gln Asp Glu Leu Ile
3575                3580                3585

Gly Arg Gly Arg Val Ser Pro Gly Asn Gly Trp Met Ile Lys Glu
3590                3595                3600

Thr Ala Cys Leu Ser Lys Ala Tyr Ala Asn Met Trp Ser Leu Met
3605                3610                3615

Tyr Phe His Lys Arg Asp Met Arg Leu Leu Ser Leu Ala Val Ser
3620                3625                3630

Ser Ala Val Pro Thr Ser Trp Val Pro Gln Gly Arg Thr Thr Trp
3635                3640                3645

Ser Ile His Gly Lys Gly Glu Trp Met Thr Thr Glu Asp Met Leu
3650                3655                3660

Glu Val Trp Asn Arg Val Trp Ile Thr Asn Asn Pro His Met Gln
3665                3670                3675

Asp Lys Thr Met Val Lys Lys Trp Arg Asp Val Pro Tyr Leu Thr
3680                3685                3690

Lys Arg Gln Asp Lys Leu Cys Gly Ser Leu Ile Gly Met Thr Asn
3695                3700                3705

Arg Ala Thr Trp Ala Ser His Ile His Leu Val Ile His Arg Ile
3710                3715                3720

Arg Thr Leu Ile Gly Gln Glu Lys Tyr Thr Asp Tyr Leu Thr Val
3725                3730                3735

Met Asp Arg Tyr Ser Val Asp Ala Asp Leu Gln Leu Gly Glu Leu
3740                3745                3750

Ile

<210> SEQ ID NO 15
<211> LENGTH: 10861
<212> TYPE: DNA
<213> ORGANISM: recombinant yellow fever virus

<400> SEQUENCE: 15

```
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaacccct gggcgtcaat atggtacgac gaggagttcg     180
ctccttgtca acaaaataa acaaaaaac aaaacaaatt ggaaacagac ctggaccttc       240
aagaggtgtt caaggattta tcttttttctt tttgttcaac attttgactg gaaaaaagat    300
cacagcccac ctaagaggt tgtggaaaat gctggaccca agacaaggct tggctgttct      360
aaggaaagtc aagagagtgg tggccagttt gatgagagga ttgtcctcaa ggaaacgccg     420
ttcccatgat gttctgactg tgcaattcct aattttggga atgctgttga tgacgggtgg     480
agtgaccttg gtgcggaaaa acagatggtt gctcctaaat gtgacatctg aggacctcgg     540 gaaacattc tctgtgggca caggcaactg cacaacaaac atttggaag ccaagtactg       600 gtgcccagac tcaatggaat acaactgtcc caatctcagt ccaagagagg agccagatga     660
cattgattgc tggtgctatg gggtggaaaa cgttagagtc gcatatggta agtgtgactc     720
```

| | |
|---|---|
| agcaggcagg tctaggaggt caagaagggc cattgacttg cctacgcatg aaaaccatgg | 780 |
| tttgaagacc cggcaagaaa aatggatgac tggaagaatg ggtgaaaggc aactccaaaa | 840 |
| gattgagaga tggttcgtga ggaaccccct ttttgcagtg acggctctga ccattgccta | 900 |
| ccttgtggga agcaacatga cgcaacgagt cgtgattgcc ctactggtct tggctgttgg | 960 |
| tccggcctac tcagctcact gcattggaat tactgacagg gatttcattg agggggtgca | 1020 |
| tggaggaact tgggtttcag ctaccctgga gcaagacaag tgtgtcactg ttatggcccc | 1080 |
| tgacaagcct tcattggaca tctcactaga gacagtagcc attgatagac ctgctgaggt | 1140 |
| gaggaaagtg tgttacaatg cagttctcac tcatgtgaag attaatgaca agtgccccag | 1200 |
| cactggagag gcccacctag ctgaagagaa cgaagggac aatgcgtgca agcgcactta | 1260 |
| ttctgataga ggctggggca atggctgtgg cctatttggg aaagggagca ttgtggcatg | 1320 |
| cgccaaattc acttgtgcca aatccatgag tttgtttgag gttgatcaga ccaaaattca | 1380 |
| gtatgtcatc agagcacaat tgcatgtagg ggccaagcag gaaaattgga ataccagcat | 1440 |
| taagactctc aagtttgatg ccctgtcagg ctcccaggaa gtcgagttca ttgggtatgg | 1500 |
| aaaagctaca ctggaatgcc aggtgcaaac tgcggtggac tttggtaaca gttacatcgc | 1560 |
| agagatggat atcgagagct ggatagtgga cagacagtgg gcccaggact tgaccctgcc | 1620 |
| atggcagagt ggaagtggcg gggtgtggag agagatgcat catcttgtcg aatttgaacc | 1680 |
| tccgcatgcc gccactatca gagtactggc cctgggaaac caggaaggct ccttgaaaac | 1740 |
| agctcttact ggcgcaatga gggttacaaa ggacacaaat gacaacaacc tttacaaact | 1800 |
| acatggtgga catgtttctt gcagagtgaa attgtcagct ttgacactca aggggacatc | 1860 |
| ctacaaaata tgcactgaca aaatgttttt tgtcaagaac ccaactgaca ctggccatgg | 1920 |
| cactgttgtg atgcaggtga aagtgtcaaa aggaacccc tgcaggattc cagtgatagt | 1980 |
| agctgatgat cttacagcgg caatcaataa aggcattttg ttacagtta accccatcgc | 2040 |
| ctcaaccaat gatgatgaag tgctgattga ggtgaaccca ccttttggag acagctacat | 2100 |
| tatcgttggg agaggagatt cacgtctcac ttaccagtgg cacaaagagg gaagctcaat | 2160 |
| aggaaagttg ttcactcaga ccatgaaagg cgtggaacgc tggccgtca tgggagacac | 2220 |
| cgcctgggat ttcagctccg ctggagggtt cttcacttcg gttgggaaag gaattcatac | 2280 |
| ggtgtttggc tctgcctttc aggggctatt tggcggcttg aactggataa caaaggtcat | 2340 |
| catgggggcg gtactcatat gggttggcat caacacaaga aacatgacaa tgtccatgag | 2400 |
| catgatcttg gtaggagtga tcatgatgtt tttgtctcta ggagttggcg ccgatcaagg | 2460 |
| atgcgccatc aactttggca agagagagct caagtgcgga gatggtatct tcatatttag | 2520 |
| agactctgat gactggctga caagtactc atactatcca gaagatcctg tgaagcttgc | 2580 |
| atcaatagtg aaagcctctt tcgaagaagg gaagtgtggc ctaaattcag ttgactccct | 2640 |
| tgagcatgag atgtggagaa gcagggcaga tgagattaat accattttg aggaaaacga | 2700 |
| ggtggacatt tctgttgtcg tgcaggatcc aaagaatgtt taccagagag gaactcatcc | 2760 |
| attttccaga attcgggatg gtctgcagta tggttggaag acttggggta agaaccttgt | 2820 |
| gttctccccca gggaggaaga atggaagctt catcatagat ggaaagtcca ggaaagaatg | 2880 |
| cccgttttca aaccgggtct ggaattcttt ccagatagag gagtttggga cgggagtgtt | 2940 |
| caccacacgc gtgtacatgg acgcagtctt tgaatacacc atagactgcg atggatctat | 3000 |
| cttgggtgca gcggtgaacg gaaaaaagag tgcccatggc tctccaacat tttgatgggg | 3060 |
| aagtcatgaa gtaaatggga catggatgat ccacaccttg gaggcattag attacaagga | 3120 |

```
gtgtgagtgg ccactgacac atacgattgg aacatcagtt gaagagagtg aaatgttcat    3180
gccgagatca atcggaggcc cagttagctc tcacaatcat atccctggat acaaggttca    3240
gacgaacgga ccttggatgc aggtaccact agaagtgaag agagaagctt gcccagggac    3300
tagcgtgatc attgatggca actgtgatgg acggggaaaa tcaaccagat ccaccacgga    3360
tagcgggaaa gttattcctg aatggtgttg ccgctcctgc acaatgccgc ctgtgagctt    3420
ccatggtagt gatgggtgtt ggtatcccat ggaaattagg ccaaggaaaa cgcatgaaag    3480
ccatctggtg cgctcctggg ttacagctgg agaaatacat gctgtcccctt ttggtttggt    3540 gagcatgatg atagcaatgg aagtggtcct aaggaaaaga cagggaccaa agcaaatgtt    3600
ggttggagga gtagtgctct tgggagcaat gctggtcggg caagtaactc tccttgattt    3660
gctgaaactc acagtggctg tgggattgca tttccatgag atgaacaatg gaggagacgc    3720
catgtatatg gcgttgattg ctgccttttc aatcagacca gggctgctca tcggctttgg    3780
gctcaggacc ctatggagcc ctcgggaacg ccttgtgctg accctaggag cagccatggt    3840
ggagattgcc ttgggtggcg tgatgggcgg cctgtggaag tatctaaatg cagtttctct    3900
ctgcatcctg acaataaatg ctgttgcttc taggaaagca tcaaatacca tcttgcccct    3960
catggctctg ttgacacctg tcactatggc tgaggtgaga cttgccgcaa tgttcttttg    4020
tgccatggtt atcatagggg tccttcacca gaatttcaag gacacctcca tgcagaagac    4080
tatacctctg gtggccctca cactcacatc ttacctgggc ttgacacaac ctttttggg     4140 cctgtgtgca tttctggcaa cccgcatatt tgggcgaagg agtatcccag tgaatgaggc    4200
actcgcagca gctggtctag tgggagtgct ggcaggactg gcttttcagg agatggagaa    4260
cttccttggt ccgattgcag ttggaggact cctgatgatg ctggttagcg tggctgggag    4320
ggtggatggg ctagagctca gaagcttggg tgaagtttca tgggaagagg aggcggagat    4380
cagcgggagt tccgcccgct atgatgtggc actcagtgaa caaggggagt tcaagctgct    4440
ttctgaagag aaagtgccat gggaccaggt tgtgatgacc tcgctggcct tggttggggc    4500
tgccctccat ccatttgctc ttctgctggt ccttgctggg tggctgtttc atgtcagggg    4560
agctaggaga agtggggatg tcttgtggga tattcccact cctaagatca tcgaggaatg    4620
tgaacatctg gaggatggga tttatggcat attccagtca accttcttgg gggcctccca    4680
gcgaggagtg ggagtggcac agggaggggt gttccacaca atgtggcatg tcacaagagg    4740
agctttcctt gtcaggaatg gcaagaagtt gattccatct tgggcttcag taaaggaaga    4800
ccttgtcgcc tatggtggct catggaagtt ggaaggcaga tgggatggag aggaagaggt    4860
ccagttgatc gcggctgttc caggaaagaa cgtggtcaac gtccagacaa aaccgagctt    4920
gttcaaagtg aggaatgggg gagaaatcgg ggctgtcgct cttgactatc cgagtggcac    4980
ttcaggatct cctattgtta acaggaacgg agaggtgatt gggctgtacg gcaatggcat    5040
ccttgtcggt gacaactcct tcgtgtccgc catatcccag actgaggtga aggaagaagg    5100
aaaggaggag ctccaagaga tcccgacaat gctaaagaaa ggaatgacaa ctgtccttga    5160
ttttcatcct ggagctggga agacaagacg tttcctccca cagatcttgg ccgagtgcgc    5220
acggagacgc ttgcgcactc ttgtgttggc ccccaccagg gttgttcttt ctgaaatgaa    5280
ggaggctttt cacggcctgg acgtgaaatt ccacacacag cttttttccg ctcacggcag    5340
cgggagagaa gtcattgatg ccatgtgcca tgccacccta acttacagga tgttggaacc    5400
aactagggtt gttaactggg aagtgatcat tatggatgaa gcccatttttt tggatccagc    5460
```

-continued

```
tagcatagcc gctagaggtt gggcagcgca cagagctagg gcaaatgaaa gtgcaacaat    5520
cttgatgaca gccacaccgc ctgggactag tgatgaattt ccacattcaa atggtgaaat    5580
agaagatgtt caaacggaca tacccagtga gccctggaac acagggcatg actggatcct    5640
ggctgacaaa aggcccacgg catggttcct tccatccatc agagctgcaa atgtcatggc    5700
tgcctctttg cgtaaggctg aaagagtgt ggtggtcctg aacaggaaaa cctttgagag    5760
agaatacccc acgataaagc agaagaaacc tgactttata ttggccactg acatagctga    5820
aatgggagcc aacctttgcg tggagcgagt gctggattgc aggacggctt ttaagcctgt    5880
gcttgtggat gaagggagga aggtggcaat aaaagggcca cttcgtatct ccgcatcctc    5940
tgctgctcaa aggaggggc gcattgggag aaatcccaac agagatggag actcatacta    6000
ctattctgag cctacaagtg aaaataatgc ccaccacgtc tgctggttgg aggcctcaat    6060
gctcttggac aacatggagg tgaggggtgg aatggtcgcc ccactctatg gcgttgaagg    6120
aactaaaaca ccagtttccc ctggtgaaat gagactgagg gatgaccaga ggaaagtctt    6180
cagagaacta gtgaggaatt gtgacctgcc cgtttggctt tcgtggcaag tggccaaggc    6240
tggtttgaag acgaatgatc gtaagtggtg ttttgaaggc cctgaggaac atgagatctt    6300
gaatgacagc ggtgaaacag tgaagtgcag ggctcctgga ggagcaaaga agcctctgcg    6360
cccaaggtgg tgtgatgaaa gggtgtcatc tgaccagagt gcgctgtctg aatttattaa    6420
gtttgctgaa ggtaggaggg agctgctgaa agtgctagtt gtgctgagtg aactccctga    6480
tttcctggct aaaaaaggtg gagaggcaat ggataccatc agtgtgttcc tccactctga    6540
ggaaggctct agggcttacc gcaatgcact atcaatgatg cctgaggcaa tgacaatagt    6600
catgctgttt atactggctg gactactgac atcgggaatg gtcatctttt tcatgtctcc    6660
caaaggcatc agtagaatgt ctatggcgat gggcacaatg gccggctgtg atatctcat    6720
gttccttgga ggcgtcaaac ccactcacat ctcctatgtc atgctcatat tctttgtcct    6780
gatggtggtt gtgatcccg agccagggca acaaaggtcc atccaagaca accaagtggc    6840
atacctcatt attggcatcc tgacgctggt ttcagcggtg cagccaacg agctaggcat    6900
gctggagaaa accaaagagg acctctttgg gaagaagaac ttaattccat ctagtgcttc    6960
accctggagt tggccggatc ttgacctgaa gccaggagct gcctggacag tgtacgttgg    7020
cattgttaca atgctctctc caatgttgca ccactggatc aaagtcgaat atggcaacct    7080
gtctctgtct ggaatagccc agtcagcctc agtcctttct ttcatggaca aggggatacc    7140
attcatgaag atgaatatct cggtcataat gctgctggtc agtggctgga attcaataac    7200
agtgatgcct ctgctctgtg gcatagggtg cgccatgctc cactggtctc tcattttacc    7260
tggaatcaaa gcgcagcagt caaagcttgc acagagaagg gtgttccatg cgttgccaa    7320
gaaccctgtg gttgatggga atccaacagt tgacattgag gaagctcctg aaatgcctgc    7380
cctttatgag aagaaactgg ctctatatct ccttcttgct ctcagcctag cttctgttgc    7440
catgtgcaga acgcccttt cattggctga aggcattgtc ctagcatcag ctgccttagg    7500
gccgctcata gagggaaaca ccagccttct ttggaatgga cccatggctg tctccatgac    7560
aggagtcatg aggggaatc actatgcttt tgtgggagtc atgtacaatc tatgaagat    7620
gaaaactgga cgccggggga gcgcgaatgg aaaaactttg ggtgaagtct ggaagaggga    7680
actgaatctg ttggacaagc gacagtttga gttgtataaa aggaccgaca ttgtggaggt    7740
ggatcgtgat acgcacgca ggcatttggc cgaagggaag gtggacaccg gggtggcggt    7800
ctccaggggg accgcaaagt taaggtggtt ccatgagcgt ggctatgtca agctggaagg    7860
```

```
tagggtgatt gacctggggt gtggccgcgg aggctggtgt tactacgctg ctgcgcaaaa   7920
ggaagtgagt ggggtcaaag gatttactct tggaagagac ggccatgaga aacccatgaa   7980
tgtgcaaagt ctgggatgga acatcatcac cttcaaggac aaaactgata tccaccgcct   8040
agaaccagtg aaatgtgaca ccctttttgtg tgacattgga gagtcatcat cgtcatcggt   8100
cacagagggg gaaaggaccg tgagagttct tgatactgta gaaaaatggc tggcttgtgg   8160
ggttgacaac ttctgtgtga aggtgttagc tccatacatg ccagatgttc ttgagaaact   8220
ggaattgctc caaaggaggt ttggcggaac agtgatcagg aaccctctct ccaggaattc   8280
cactcatgaa atgtactacg tgtctggagc ccgcagcaat gtcacattta ctgtgaacca   8340
aacatcccgc tcctgatga ggagaatgag gcgtccaact ggaaaagtga ccctggaggc   8400
tgacgtcatc ctcccaattg ggacacgcag tgttgagaca gacaagggac ccctggacaa   8460
agaggccata aagaaaggg ttgagaggat aaaatctgag tacatgacct cttggtttta   8520
tgacaatgac aaccctaca ggacctggca ctactgtggc tcctatgtca caaaaaccctc   8580
aggaagtgcg gcgagcatgg taaatggtgt tattaaaatt ctgacatatc catgggacag   8640
gatagaggag gtcaccagaa tggcaatgac tgacacaacc ccttttggac agcaaagagt   8700
gtttaaagaa aaagttgaca ccagagcaaa ggatccacca gcgggaacta ggaagatcat   8760
gaaagttgtc aacaggtggc tgttccgcca cctggccaga gaaaagagcc ccagactgtg   8820
cacaaaggaa gaatttattg caaaagtccg aagtcatgca gccattggag cttacctgga   8880
agaacaagaa cagtggaaga ctgccaatga ggctgtccaa gacccaaagt tctgggaact   8940
ggtggatgaa gaaaggaagc tgcaccaaca aggcaggtgt cggacttgtg tgtacaacat   9000
gatggggaaa agagagaaga agctgtcaga gtttgggaaa gcaaagggaa gccgtgccat   9060
atggtatatg tggctgggag cgcggtatct tgagtttgag gccctgggat tcctgaatga   9120
ggaccattgg gcttccaggg aaaactcagg aggaggagtg gaaggcattg gcttacaata   9180
cctaggatat gtgatcagag acctggctgc aatggatggt ggtggattct acgcggatga   9240
caccgctgga tgggacacgc gcatcacaga ggcagaccct gatgatgaac aggagatctt   9300
gaactacatg agcccacatc acaaaaaact ggcacaagca gtgatggaaa tgacatacaa   9360
gaacaaagtg gtgaaagtgt tgagaccagc cccaggaggg aaagcctaca tggatgtcat   9420
aagtcgacga gaccagagag gatccgggca ggtagtgact tatgctctga acaccatcac   9480
caacttgaaa gtccaattga tcagaatggc agaagcagag atggtgatac atcaccaaca   9540
tgttcaagat tgtgatgaat cagttctgac caggctggag gcatggctca ctgagcacgg   9600
atgtaacaga ctgaagagga tggcggtgag tggagacgac tgtgtggtcc ggcccatcga   9660
tgacaggttc ggcctggccc tgtcccatct caacgccatg tccaaggtta aaaggacat   9720
atctgaatgg cagccatcaa aagggtggaa tgattgggag aatgtgccct tctgttccca   9780
ccacttccat gaactacagc tgaaggatgg caggaggatt gtggtgcctt gccgagaaca   9840
ggacgagctc attgggagag aagggtgtc tccaggaaac ggctggatga tcaaggaaac   9900
agcttgcctc agcaaagcct atgccaacat gtggtcactg atgtattttc acaaaaggga   9960
catgaggcta ctgtcattgg ctgtttcctc agctgttccc acctcatggg ttccacaagg  10020
acgcacaaca tggtcgattc atgggaaagg ggagtggatg accacggaag acatgcttga  10080
ggtgtggaac agagtatgga taccaacaa cccacacatg caggacaaga aatggtgaa  10140
aaaatggaga gatgtccctt atctaaccaa gagacaagac aagctgtgcg gatcactgat  10200
```

-continued

```
tggaatgacc aatagggcca cctgggcctc ccacatccat ttagtcatcc atcgtatccg   10260
aacgctgatt ggacaggaga aatacactga ctacctaaca gtcatggaca ggtattctgt   10320
ggatgctgac ctgcaactgg gtgagcttat ctgaaacacc atctaacagg aataaccggg   10380
atacaaacca cgggtggaga accgactccc cacaacctg aaaccgggat ataaaccacg    10440
gctggagaac cgggctccgc acttaaaatg aaacagaaac cgggataaaa actacggatg   10500
gagaaccgga ctccacacat tgagacagaa gaagttgtca gcccagaacc ccacacgagt   10560
tttgccactg ctaagctgtg aggcagtgca ggctgggaca gccgacctcc aggttgcgaa   10620
aaacctggtt tctgggacct cccaccccag agtaaaaaga acggagcctc cgctaccacc   10680
ctcccacgtg gtggtagaaa gacggggtct agaggttaga ggagaccctc cagggaacaa   10740
atagtgggac catattgacg ccagggaaag accggagtgg ttctctgctt ttcctccaga   10800
ggtctgtgag cacagtttgc tcaagaataa gcagaccttt ggatgacaaa cacaaaacca   10860
c                                                                  10861
```

<210> SEQ ID NO 16
<211> LENGTH: 21
<212> TYPE: DNA
<213> ORGANISM: yellow fever virus

<400> SEQUENCE: 16
cggggtgtgg agagagatgc a                                            21

<210> SEQ ID NO 17
<211> LENGTH: 21
<212> TYPE: DNA
<213> ORGANISM: yellow fever virus

<400> SEQUENCE: 17
gggagtcaac tgaatttagg c 21

<210> SEQ ID NO 18
<211> LENGTH: 47
<212> TYPE: DNA
<213> ORGANISM: Dengue 4 virus

<400> SEQUENCE: 18
gcttgattcc caccggtatg gcgttttccc tcagcacaag agatggc 47

<210> SEQ ID NO 19
<211> LENGTH: 19
<212> TYPE: DNA
<213> ORGANISM: dengue 4 virus

<400> SEQUENCE: 19
gggcagaatg catggctcc 19

<210> SEQ ID NO 20
<211> LENGTH: 19
<212> TYPE: DNA
<213> ORGANISM: dengue 4 virus

<400> SEQUENCE: 20
ggagccatgc attctgccc 19

<210> SEQ ID NO 21
<211> LENGTH: 49
<212> TYPE: DNA
<213> ORGANISM: dengue 4 virus

<400> SEQUENCE: 21

```
gacgccacac aacccatgtc ggcgccaact gtgaagccca gaaacagag          49
```

<210> SEQ ID NO 22
<211> LENGTH: 14498
<212> TYPE: DNA
<213> ORGANISM: recombinant E.coli

<400> SEQUENCE: 22

```
gtgaccacgg gataataccg cgccacatag cagaacttta aaagtgctca tcattggaaa    60
acgttcttcg gggcgaaaac tctcaaggat cttaccgctg ttgagatcca gttcgatgta   120
acccactcgt gcacccaact gatcttcagc atcttttact ttcaccagcg tttctgggtg   180
agcaaaaaca ggaaggcaaa atgccgcaaa aagggaata agggcgacac ggaaatgttg   240
aatactcata ctcttccttt ttcaatatta ttgaagcatt tatcagggtt attgtctcat   300
gagcggatac atatttgaat gtatttagaa aaataaacaa ataggggttc cgcgcacatt   360
tccccgaaaa gtgccacctg acgtcgatcg cggccgctag cgatgaccct gctgattggt   420
tcgctgacca tttccgggtg cgggacggcg ttaccagaaa ctcagaaggt tcgtccaacc   480
aaaccgactc tgacggcagt ttacgagaga gatgataggg tctgcatcag taagccagat   540
gctacacaat taggcttgta catattgtcg ttagaacgcg gctacaatta atacataacc   600
ttatgtatca tacacatacg atttaggtga cactatagag taaatcctgt gtgctaattg   660
aggtgcattg gtctgcaaat cgagttgcta ggcaataaac acatttggat taattttaat   720
cgttcgttga gcgattagca gagaactgac cagaacatgt ctggtcgtaa agctcaggga   780
aaaccctgg gcgtcaatat ggtacgacga ggagttcgct ccttgtcaaa caaaataaaa   840
caaaaacaa aacaaattgg aaacagacct ggaccttcaa gaggtgttca aggatttatc   900
tttttctttt tgttcaacat tttgactgga aaaaagatca cagcccacct aaagaggttg   960
tggaaaatgc tggacccaag acaaggcttg gctgttctaa ggaaagtcaa gagagtggtg  1020
gccagtttga tgagaggatt gtcctcaagg aaacgccgtt cccatgatgt tctgactgtg  1080
caattcctaa ttttgggaat gctgttgatg accggtatgc cgtttccct cagcacaaga  1140
gatggcgaac ccctcatgat agtggcaaaa catgaaaggg ggagacctct cttgtttaag  1200
acaacagagg ggatcaacaa atgcactctc attgccatgg acttgggtga atgtgtgag  1260
gacactgtca cgtataaatg cccctactg gtcaataccg aacctgaaga cattgattgc  1320
tggtgcaacc tcacgtctac ctgggtcatg tatgggacat gcacccagag cggagaacgg  1380
agacgagaga agcgctcagt agctttaaca ccacattcag gaatgggatt ggaaacaaga  1440
gctgagacat ggatgtcatc ggaaggggct tggaagcatg ctcagagagt agagagctgg  1500
atactcagaa acccaggatt cgcgctcttg gcaggattta tggcttatat gattgggcaa  1560
acaggaatcc agcgaactgt cttctttgtc ctaatgatgc tggtcgcccc atcctacgga  1620
atgcgatgcg taggagtagg aaacagagac tttgtggaag gagtctcagg tggagcatgg  1680
gtcgacctgg tgctagaaca tggaggatgc gtcacaacca tggcccaggg aaaaccaacc  1740
ttggattttg aactgactaa gacaacagcc aaggaagtgg ctctgttaag aacctattgc  1800
attgaagcct caatatcaaa cataactacg gcaacaagat gtccaacgca aggagagcct  1860
tatctgaaag aggaacagga ccaacagtac atttgccgga gagatgtggt agacagaggg  1920
tggggcaatg gctgtggctt gtttggaaaa ggaggagttg tgacatgtgc gaagttttca  1980
```

```
tgttcgggga agataacagg caatttggtc caaattgaga accttgaata cacagtggtt    2040
gtaacagtcc acaatggaga cacccatgca gtaggaaatg acacatccaa tcatggagtt    2100
acagccatga taactcccag gtcaccatcg gtggaagtca aattgccgga ctatggagaa    2160
ctaacactcg attgtgaacc caggtctgga attgacttta atgagatgat tctgatgaaa    2220
atgaaaaaga aaacatggct cgtgcataag caatggtttt tggatctgcc tcttccatgg    2280
acagcaggag cagacacatc agaggttcac tggaattaca agagagaat ggtgacattt      2340
aaggttcctc atgccaagag acaggatgtg acagtgctgg atctcaggaa aggagccatg    2400
cattctgccc tcgctggagc cacagaagtg gactccggtg atggaaatca catgtttgca    2460
ggacatctca agtgcaaagt ccgtatggag agattgagaa tcaagggaat gtcatacacg    2520
atgtgttcag aaagttttc aattgacaaa gagatggcag aaacacagca tgggacaaca     2580
gtgatgaaag tcaagtatga aggtgctgga gctccgtgta aagtccccat agagataaga    2640
gatgtaaaca aggaaaaagt ggttgggcgt atcatctcat ccaccccttt ggctgagaat    2700
accaacagtg taaccaacat agaattagaa ccccccttg gggacagcta catagtgata     2760
ggtgttggaa acagcgcatt aacactccac tggttcagga agggagttc cattggcaag     2820
atgtttgagt ccacatacag aggtgcaaaa cgaatggcca ttctaggtga aacagcttgg    2880
gattttggtt ccgttggtgg actgttcaca tcattgggaa aggctgtgca ccaggttttt    2940
ggaagtgtgt acacaaccat gtttggagga gtctcatgga tgattagaat cctaattggg    3000
ttcttagtgt tgtggattgg cacgaactca aggaacactt caatggctat gacgtgcata    3060
gctgttggag gaatcactct gtttctgggc ttcacagttg gcgccgatca aggatgcgcc    3120
atcaactttg gcgtgagcaa gggcgaggag ctgttcaccg gggtggtgcc catcctggtc    3180
gagctggacg gcgacgtaaa cggccacaag ttcagcgtgt ccggcgaggg cgagggcgat    3240
gccacctacg gcaagctgac cctgaagttc atctgcacca ccggcaagct gcccgtgccc    3300
tggcccaccc tcgtgaccac cctgacctac ggcgtgcagt gcttcagccg ctaccccgac    3360
cacatgaagc agcacgactt cttcaagtcc gccatgcccg aaggctacgt ccaggagcgc    3420
accatcttct tcaaggacga cggcaactac aagacccgcg ccgaggtgaa gttcgagggc    3480
gacaccctgg tgaaccgcat cgagctgaag ggcatcgact tcaaggagga cggcaacatc    3540
ctggggcaca agctggagta caactacaac agccacaacg tctatatcat ggccgacaag    3600
cagaagaacg gcatcaaggt gaacttcaag atccgccaca acatcgagga cggcagcgtg    3660
cagctcgccg accactacca gcagaacacc cccatcggcg acggccccgt gctgctgccc    3720
gacaaccact acctgagcac ccagtccgcc ctgagcaaag accccaacga gaagcgcgat    3780
cacatggtcc tgctggagtt cgtgaccgcc gccgggatca ctctcggcat ggacgagctg    3840
tacaagaagt tgttcactca gaccatgaaa ggcgtggaac gcctggccgt catgggagac    3900
accgcctggg atttcagctc cgctggaggg ttcttcactt cggttgggaa aggaattcat    3960
acggtgtttg gctctgcctt tcaggggcta tttggcggct tgaactggat aacaaaggtc    4020
atcatggggg cggtacttat atgggttggc atcaacacaa gaaacatgac aatgtccatg    4080
agcatgatct tggtaggagt gatcatgatg ttttgtctc taggagttgg cgccgatcaa    4140
ggatgcgcca tcaactttgg caagagagag ctcaagtgcg gagatggtat cttcatattt    4200
agagactctg atgactggct gaacaagtac tcatactatc cagaagatcc tgtgaagctt    4260
gcatcaatag tgaaagcctc tttcgaagaa gggaagtgtg gcctaaattc agttgactcc    4320
cttgagcatg agatgtggag aagcagggca gatgagatta ataccatttt tgaggaaaac    4380
```

```
gaggtggaca tttctgttgt cgtgcaggat ccaaagaatg tttaccagag aggaactcat    4440
ccattttcca gaattcggga tggtctgcag tatggttgga agacttgggg taagaacctt    4500
gtgttctccc cagggaggaa gaatggaagc ttcatcatag atggaaagtc caggaaagaa    4560
tgcccgtttt caaaccgggt ctggaattct ttccagatag aggagtttgg gacgggagtg    4620
ttcaccacac gcgtgtacat ggacgcagtc tttgaataca ccatagactg cgatggatct    4680
atcttgggtg cagcggtgaa cggaaaaaag agtgcccatg gctctccaac attttggatg    4740
ggaagtcatg aagtaaatgg gacatggatg atccacacct tggaggcatt agattacaag    4800
gagtgtgagt ggccactgac acatacgatt ggaacatcag ttgaagagag tgaaatgttc    4860
atgccgagat caatcggagg cccagttagc tctcacaatc atatccctgg atacaaggtt    4920
cagacgaacg gaccttggat gcaggtacca ctagaagtga agagagaagc ttgcccaggg    4980
actagcgtga tcattgatgg caactgtgat ggacggggaa aatcaaccag atccaccacg    5040
gatagcggga aagttattcc tgaatggtgt gccgctcct gcacaatgcc gcctgtgagc    5100
ttccatggta gtgatgggtg ttggtatccc atggaaatta ggccaaggaa aacgcatgaa    5160
agccatctgg tgcgctcctg ggttacagct ggagaaatac atgctgtccc ttttggtttg    5220
gtgagcatga tgatagcaat ggaagtggtc ctaaggaaaa gacagggacc aaagcaaatg    5280
ttggttggag gagtagtgct cttgggagca atgctggtcg ggcaagtaac tctccttgat    5340
ttgctgaaac tcacagtggc tgtgggattg catttccatg agatgaacaa tggaggagac    5400
gccatgtata tggcgttgat tgctgccttt tcaatcagac cagggctgct catcggcttt    5460
gggctcagga cccctatggag ccctcgggaa cgccttgtgc tgaccctagg agcagccatg    5520
gtggagattg ccttgggtgg cgtgatgggc ggcctgtgga agtatctaaa tgcagtttct    5580
ctctgcatcc tgacaataaa tgctgttgct tctaggaaag catcaaatac catcttgccc    5640
ctcatggctc tgttgacacc tgtcactatg gctgaggtga gacttgccgc aatgttcttt    5700
tgtgccatgg ttatcatagg ggtccttcac cagaatttca aggacacctc catgcagaag    5760
actatacctc tggtggccct cacactcaca tcttacctgg gcttgacaca acctttttg    5820 ggcctgtgtg catttctggc aacccgcata tttgggcgaa ggagtatccc agtgaatgag    5880
gcactcgcag cagctggtct agtgggagtg ctggcaggac tggctttca ggagatggag    5940 aacttccttg gtccgattgc agttggagga ctcctgatga tgctggttag cgtggctggg    6000
agggtggatg ggctagagct caagaagctt ggtgaagttt catgggaaga ggaggcggag    6060
atcagcggga gttccgcccg ctatgatgtg gcactcagtg aacaagggga gttcaagctg    6120
ctttctgaag agaaagtgcc atgggaccag gttgtgatga cctcgctggc cttggttggg    6180
gctgccctcc atccatttgc tcttctgctg gtccttgctg ggtggctgtt tcatgtcagg    6240
ggagctagga gaagtgggga tgtcttgtgg gatattccca ctcctaagat catcgaggaa    6300
tgtgaacatc tggaggatgg gatttatggc atattccagt caaccttctt gggggcctcc    6360
cagcgaggag tgggagtggc acaggagggg tgttccacca atgtggca tgtcacaaga    6420 ggagctttcc ttgtcaggaa tggcaagaag ttgattccat cttgggcttc agtaaaggaa    6480
gaccttgtcg cctatggtgg ctcatggaag ttgaaggca gatgggatgg agaggaagag    6540
gtccagttga tcgcggctgt tccaggaaag aacgtggtca acgtccagac aaaaccgagc    6600
ttgttcaaag tgaggaatgg gggagaaatc ggggctgtcg ctcttgacta tccgagtggc    6660
acttcaggat ctccttattgt taacaggaac ggagaggtga ttgggctgta cggcaatggc    6720
```

```
atccttgtcg gtgacaactc cttcgtgtcc gccatatccc agactgaggt gaaggaagaa    6780
ggaaaggagg agctccaaga gatcccgaca atgctaaaga aaggaatgac aactgtcctt    6840
gattttcatc ctggagctgg gaagacaaga cgtttcctcc cacagatctt ggccgagtgc    6900
gcacggagac gcttgcgcac tcttgtgttg gcccccacca gggttgttct ttctgaaatg    6960
aaggaggctt ttcacggcct ggacgtgaaa ttccacacac aggcttttc cgctcacggc     7020 agcgggagag aagtcattga tgccatgtgc catgccaccc taacttacag gatgttggaa    7080
ccaactaggg ttgttaactg ggaagtgatc attatggatg aagcccattt tttggatcca    7140
gctagcatag ccgctagagg ttgggcagcg cacagagcta gggcaaatga aagtgcaaca    7200
atcttgatga cagccacacc gcctgggact agtgatgaat tccacattc aaatggtgaa     7260 atagaagatg ttcaaacgga catacccagt gagccctgga acacagggca tgactggatc    7320
ctggctgaca aaaggcccac ggcatggttc cttccatcca tcagagctgc aaatgtcatg    7380
gctgcctctt tgcgtaaggc tggaaagagt gtggtggtcc tgaacaggaa aacctttgag    7440
agagaatacc ccacgataaa gcagaagaaa cctgacttta tattggccac tgacatagct    7500
gaaatgggag ccaacctttg cgtggagcga gtgctggatt gcaggacggc ttttaagcct    7560
gtgcttgtgg atgaagggag gaaggtggca ataaaagggc cacttcgtat ctccgcatcc    7620
tctgctgctc aaaggagggg gcgcattggg agaaatccca acagagatgg agactcatac    7680
tactattctg agcctacaag tgaaaataat gcccaccacg tctgctggtt ggaggcctca    7740
atgctcttgg acaacatgga ggtgaggggt ggaatggtcg ccccactcta tggcgttgaa    7800
ggaactaaaa caccagtttc ccctggtgaa atgagactga gggatgacca gaggaaagtc    7860
ttcagagaac tagtgaggaa ttgtgacctg cccgtttggc tttcgtggca gtggccaag    7920 gctggtttga gacgaatga tcgtaagtgg tgttttgaag gccctgagga acatgagatc    7980
ttgaatgaca gcggtgaaac agtgaagtgc agggctcctg gaggagcaaa gaagcctctg    8040
cgcccaaggt ggtgtgatga aagggtgtca tctgaccaga gtgcgctgtc tgaatttatt    8100
aagtttgctg aaggtaggag gggagctgct gaagtgctag ttgtgctgag tgaactccct    8160
gatttcctgg ctaaaaaagg tggagaggca atggatacca tcagtgtgtt cctccactct    8220
gaggaaggct ctagggctta ccgcaatgca ctatcaatga tgcctgaggc aatgacaata    8280
gtcatgctgt ttatactggc tggactactg acatcgggaa tggtcatctt tttcatgtct    8340
cccaaaggca tcagtagaat gtctatggcg atgggcacaa tggccggctg tggatatctc    8400
atgttccttg gaggcgtcaa acccactcac atctcctatg tcatgctcat attctttgtc    8460
ctgatggtgg ttgtgatccc cgagccaggg caacaaaggt ccatccaaga caaccaagtg    8520
gcatacctca ttattggcat cctgacgctg gtttcagcgg tggcagccaa cgagctaggc    8580
atgctggaga aaaccaaaga ggacctcttt gggaagaaga cttaattcc atctagtgct     8640 tcaccctgga gttggccgga tcttgacctg aagccaggag ctgcctggac agtgtacgtt    8700
ggcattgtta caatgctctc tccaatgttg caccactgga tcaaagtcga atatggcaac    8760
ctgtctctgt ctggaatagc ccagtcagcc tcagtccttt cttcatgga caaggggata    8820 ccattcatga agatgaatat ctcggtcata atgctgctgg tcagtggctg gaattcaata    8880
acagtgatgc ctctgctctg tggcataggg tgcgccatgc tccactggtc tctcattta    8940 cctggaatca aagcgcagca gtcaaagctt gcacagagaa gggtgttcca tggcgttgcc    9000
aagaaccctg tggttgatgg gaatccaaca gttgacattg aggaagctcc tgaaatgcct    9060
gcccttttag agaagaaact ggctctatat ctccttcttg ctctcagcct agcttctgtt    9120
```

```
gccatgtgca gaacgccctt ttcattggct gaaggcattg tcctagcatc agctgcctta   9180
gggccgctca tagagggaaa caccagcctt ctttggaatg gacccatggc tgtctccatg   9240
acaggagtca tgagggggaa tcactatgct tttgtgggag tcatgtacaa tctatggaag   9300
atgaaaactg gacgccgggg gagcgcgaat ggaaaaactt tgggtgaagt ctggaagagg   9360
gaactgaatc tgttggacaa gcgacagttt gagttgtata aaaggaccga cattgtggag   9420
gtggatcgtg atacggcacg caggcatttg gccgaaggga aggtgacaca cggggtggcg   9480
gtctccaggg ggaccgcaaa gttaaggtgg ttccatgagc gtggctatgt caagctggaa   9540
ggtagggtga ttgacctggg gtgtggccgc ggaggctggt gttactacgc tgctgcgcaa   9600
aaggaagtga gtggggtcaa aggatttact cttggaagag acggccatga gaaacccatg   9660
aatgtgcaaa gtctgggatg gaacatcatc accttcaagg acaaaactga tatccaccgc   9720
ctagaaccag tgaaatgtga cacccttttg tgtgacattg gagagtcatc atcgtcatcg   9780
gtcacagagg gggaaaggac cgtgagagtt cttgatactg tagaaaaatg gctggcttgt   9840
ggggttgaca acttctgtgt gaaggtgtta gctccataca tgccagatgt tcttgagaaa   9900
ctggaattgc tccaaaggag gtttggcgga acagtgatca ggaaccctct ctccaggaat   9960
tccactcatg aaatgtacta cgtgtctgga gcccgcagca atgtcacatt tactgtgaac  10020
caaacatccc gcctcctgat gaggagaatg aggcgtccaa ctggaaaagt gaccctggag  10080
gctgacgtca tcctcccaat tgggacacgc agtgttgaga cagacaaggg accccctggac 10140
aaagaggcca tagaagaaag ggttgagagg ataaaatctg agtacatgac ctcttggttt  10200
tatgacaatg acaaccccta caggacctgg cactactgtg gctcctatgt cacaaaaacc  10260
tcaggaagtg cggcgagcat ggtaaatggt gttattaaaa ttctgacata tccatgggac  10320
aggatagagg aggtcaccag aatggcaatg actgacacaa cccctttttgg acagcaaaga 10380
gtgtttaaag aaaaagttga caccagagca aaggatccac cagcgggaac taggaagatc  10440
atgaaagttg tcaacaggtg gctgttccgc cacctggcca gagaaaagag ccccagactg  10500
tgcacaaagg aagaatttat tgcaaaagtc cgaagtcatg cagccattgg agcttacctg  10560
gaagaacaag aacagtggaa gactgccaat gaggctgtcc aagacccaaa gttctgggaa  10620
ctggtggatg aagaaggaa gctgcaccaa caaggcaggt gtcggacttg tgtgtacaac  10680
atgatgggga aaagagagaa gaagctgtca gagtttggga agcaaagggg aagccgtgcc  10740
atatggtata tgtggctggg agcgcggtat cttgagtttg aggccctggg attcctgaat  10800
gaggaccatt gggcttccag ggaaaactca ggaggaggag tggaaggcat ggcttacaa   10860
tacctaggat atgtgatcag agacctggct gcaatggatg gtggtggatt ctacgcggat  10920
gacaccgctg gatgggacac gcgcatcaca gaggcagacc ttgatgatga acaggagatc  10980
ttgaactaca tgagcccaca tcacaaaaaa ctggcacaag cagtgatgga aatgacatac  11040
aagaacaaag tggtgaaagt gttgagacca gccccaggag ggaaagccta catggatgtc  11100
ataggtcgac gagaccagag aggatccggg caggtagtga cttatgctct gaacaccatc  11160
accaacttga aagtccaatt gatcagaatg cagaagcag agatggtgat acatcaccaa  11220
catgttcaag attgtgatga atcagttctg accaggctgg aggcatggct cactgagcac  11280
ggatgtaaca gactgaagag gatggcggtg agtggagacg actgtgtggt ccggcccatc  11340
gatgacaggt tcgcctggc cctgtcccat ctcaacgcca tgtccaaggt tagaaaggac  11400
atatctgaat ggcagccatc aaaagggtgg aatgattggg agaatgtgcc cttctgttcc  11460
```

-continued

```
caccacttcc atgaactaca gctgaaggat ggcaggagga ttgtggtgcc ttgccgagaa    11520
caggacgagc tcattgggag aggaagggtg tctccaggaa acggctggat gatcaaggaa    11580
acagcttgcc tcagcaaagc ctatgccaac atgtggtcac tgatgtattt tcacaaaagg    11640
gacatgaggc tactgtcatt ggctgttttcc tcagctgttc ccacctcatg ggttccacaa   11700
ggacgcacaa catggtcgat tcatgggaaa ggggagtgga tgaccacgga agacatgctt    11760
gaggtgtgga acagagtatg gataaccaac aacccacaca tgcaggacaa gacaatggtg    11820
aaaaaatgga gagatgtccc ttatctaacc aagagacaag acaagctgtg cggatcactg    11880
attggaatga ccaatagggc cacctgggcc tcccacatcc atttagtcat ccatcgtatc    11940
cgaacgctga ttggacagga gaaatacact gactacctaa cagtcatgga caggtattct    12000
gtggatgctg acctgcaact gggtgagctt atctgaaaca ccatctaaca ggaataaccg    12060
ggatacaaac cacgggtgga gaaccggact ccccacaacc tgaaaccggg atataaacca    12120
cggctggaga accgggctcc gcacttaaaa tgaaacagaa accgggataa aaactacgga    12180
tggagaaccg gactccacac attgagacag aagaagttgt cagcccagaa ccccacacga    12240
gttttgccac tgctaagctg tgaggcagtg caggctggga cagccgacct ccaggttgcg    12300
aaaaacctgg tttctgggac ctcccacccc agagtaaaaa gaacgagcc tccgctacca    12360 ccctcccacg tggtggtaga aagacggggt ctagaggtta gaggagaccc tccagggaac    12420
aaatagtggg accatattga cgccagggaa agaccggagt ggttctctgc ttttcctcca    12480
gaggtctgtg agcacagttt gctcaagaat aagcagacct ttggatgaca aacacaaaac    12540
cactcgagca agacgtttcc cgttgaatat ggctcataac accccttgta ttactgttta    12600
tgtaagcaga cagttttatt gttcatgatg atatatttttt atcttgtgca atgtaacatc    12660
agagattttg agacacaacg tggctttgtt gaataaatcg aacttttgct gagttgaagg    12720
atcagatcac gcatcttccc gacaacgcag accgttccgt ggcaaagcaa agttcaaaa     12780 tcaccaactg gtccacctac aacaaagctc tcatcaaccg tggctccctc actttctggc    12840
tggatgatgg ggcgattcag gcctggtatg agtcagcaac accttcttca cgaggcagac    12900
ctcagcgcta gcggagtgta tactggctta ctatgttggc actgatgagg gtgtcagtga    12960
agtgcttcat gtggcaggag aaaaaaggct gcaccggtgc gtcagcagaa tatgtgatac    13020
aggatatatt ccgcttcctc gctcactgac tcgctacgct cggtcgttcg actgcggcga    13080
gcggaaatgg cttacgaacg gggcggagat ttcctggaag atgccaggaa gatacttaac    13140
agggaagtga gagggccgcg gcaaagccgt ttttccatag gctccgcccc cctgacaagc    13200
atcacgaaat ctgacgctca aatcagtggt ggcgaaaccc gacaggacta taaagatacc    13260
aggcgtttcc cctggcggct ccctcgtgcg ctctcctgtt cctgcctttc ggtttaccgg    13320
tgtcattccg ctgttatggc cgcgtttgtc tcattccacg cctgacactc agttccgggt    13380
aggcagttcg ctccaagctg gactgtatgc acgaacccc cgttcagtcc gaccgctgcg     13440
ccttatccgg taactatcgt cttgagtcca acccggaaag acatgcaaaa gcaccactgg    13500
cagcagccac tggtaattga tttagaggag ttagtcttga agtcatgcgc cggttaaggc    13560
taaactgaaa ggacaagttt tggtgactgc gctcctccaa gccagttacc tcggttcaaa    13620
gagttggtag ctcagagaac cttcgaaaaa ccgccctgca aggcggtttt ttcgttttca    13680
gagcaagaga ttacgcgcag accaaaacga tctcaagaag atcatcttat taagggtct    13740 gacgctcagt ggaacgaaaa ctcacgttaa gggattttgg tcatgagatt atcaaaaagg    13800
atcttcacct agatcctttt aaattaaaaa tgaagtttta aatcaatcta agtatatat     13860
```

```
gagtaaactt ggtctgacag ttaccaatgc ttaatcagtg aggcacctat ctcagcgatc    13920
tgtctatttc gttcatccat agttgcctga ctccccgtcg tgtagataac tacgatacgg    13980
gagggcttac catctggccc cagtgctgca atgataccgc gagacccacg ctcaccggct    14040
ccagatttat cagcaataaa ccagccagcc ggaagggccg agcgcagaag tggtcctgca    14100
actttatccg cctccatcca gtctattaat tgttgccggg aagctagagt aagtagttcg    14160
ccagttaata gtttgcgcaa cgttgttgcc attgctgcag gcatcgtggt gtcacgctcg    14220
tcgtttggta tggcttcatt cagctccggt tcccaacgat caaggcgagt tacatgatcc    14280
cccatgttgt gcaaaaaagc ggttagctcc ttcggtcctc cgatcgttgt cagaagtaag    14340
ttggccgcag tgttatcact catggttatg gcagcactgc ataattctct tactgtcatg    14400
ccatccgtaa gatgctttc tgtgactggt gagtactcaa ccaagtcatt ctgagaatag    14460
tgtatgcggc gaccgagttg ctcttgcccg gcgtcaac                           14498
```

<210> SEQ ID NO 23  
<211> LENGTH: 11905  
<212> TYPE: DNA  
<213> ORGANISM: recombinant chimeric yellow fever dengue 4 virus

<400> SEQUENCE: 23

```
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
ctccttgtca aacaaaataa aacaaaaaac aaaacaaatt ggaaacagac ctggaccttc     240
aagaggtgtt caaggattta ctttttcttt tttgttcaac atttttgactg gaaaaaagat     300 cacagcccac ctaaagaggt tgtggaaaat gctggaccca agacaaggct tggctgttct     360
aaggaaagtc aagagagtgg tggccagttt gatgagagga ttgtcctcaa ggaaacgccg     420
ttcccatgat gttctgactg tgcaattcct aattttggga atgctgttga tgaccggtat     480
ggcgttttcc ctcagcacaa gagatggcga acccctcatg ataagtggcaa acatgaaaag     540 ggggagacct ctcttgttta gacaacaga ggggatcaac aaatgcactc tcattgccat     600
ggacttgggt gaaatgtgtg aggacactgt cacgtataaa tgcccctac tggtcaatac     660 cgaacctgaa gacattgatt gctggtgcaa cctcacgtct acctgggtca tgtatggac     720 atgcacccag agcggagaac ggagacgaga gaagcgctca gtagctttaa caccacattc     780
aggaatggga ttgaaacaa gagctgagac atggatgtca tcggaagggg cttggaagca     840
tgctcagaga gtagagagct ggatactcag aaacccagga ttcgcgctct ggcaggatt     900 tatggcttat atgattgggc aaacaggaat ccagcgaact gtcttctttg tcctaatgat     960
gctggtcgcc ccatcctacg gaatgcgatg cgtaggagta ggaaacagag actttgtgga    1020
aggagtctca ggtggagcat gggtcgacct ggtgctagaa catggaggat gcgtcacaac    1080
catggcccag ggaaaaccaa ccttggattt tgaactgact aagacaacag ccaaggaagt    1140
ggctctgtta agaacctatt gcattgaagc ctcaatatca aacataacta cggcaacaag    1200
atgtccaacg caaggagagc cttatctgaa agaggaacag gaccaacagt acatttgccg    1260
gagagatgtg gtagacagag ggtggggcaa tggctgtggc ttgtttggaa aggaggagt    1320 tgtgacatgt gcgaagtttt catgttcggg aagataaca ggcaatttgg tccaaattga    1380
gaaccttgaa tacacagtgg ttgtaacagt ccacaatgga gacacccatg cagtaggaaa    1440
```

-continued

```
tgacacatcc aatcatggag ttacagccat gataactccc aggtcaccat cggtggaagt      1500
caaattgccg gactatggag aactaacact cgattgtgaa cccaggtctg gaattgactt      1560
taatgagatg attctgatga aaatgaaaaa gaaaacatgg ctcgtgcata agcaatggtt      1620
tttggatctg cctcttccat ggacagcagg agcagacaca tcagaggttc actggaatta      1680
caaagagaga atggtgacat ttaaggttcc tcatgccaag agacaggatg tgacagtgct      1740
gggatctcag gaaggagcca tgcattctgc cctcgctgga gccacagaag tggactccgg      1800
tgatggaaat cacatgtttg caggacatct caagtgcaaa gtccgtatgg agagattgag      1860
aatcaaggga atgtcataca cgatgtgttc aggaaagttt tcaattgaca aagagatggc      1920
agaaacacag catgggacaa cagtgatgaa agtcaagtat gaaggtgctg agctccgtg      1980 taaagtcccc atagagataa gagatgtaaa caaggaaaaa gtggttgggc gtatcatctc      2040
atccacccct ttggctgaga ataccaacag tgtaaccaac atagaattag aaccccccTT      2100
tggggacagc tacatagtga taggtgttgg aaacagcgca ttaacactcc actggttcag      2160
gaaagggagt tccattggca agatgtttga gtccacatac agaggtgcaa aacgaatggc      2220
cattctaggt gaaacagctt gggattttgg ttccgttggt ggactgttca catcattggg      2280
aaaggctgtg caccaggttt ttggaagtgt gtacacaacc atgtttggag gagtctcatg      2340
gatgattaga atcctaattg ggttcttagt gttgtggatt ggcacgaact caaggaacac      2400
ttcaatggct atgacgtgca tagctgttgg aggaatcact ctgtttctgg gcttcacagt      2460
tggcgccgat caaggatgcg ccatcaactt ggcgtgagc aagggcgagg agctgttcac      2520
cggggtggtg cccatcctgg tcgagctgga cggcgacgta aacggccaca gttcagcgt      2580 gtccggcgag ggcgagggcg atgccaccta cggcaagctg accctgaagt tcatctgcac      2640
caccggcaag ctgcccgtgc cctggcccac cctcgtgacc accctgacct acggcgtgca      2700
gtgcttcagc cgctacccg accacatgaa gcagcacgac ttcttcaagt ccgccatgcc      2760
cgaaggctac gtccaggagc gcaccatctt cttcaaggac gacggcaact acaagacccg      2820
cgccgaggtg aagttcgagg gcgacaccct ggtgaaccgc atcgagctga agggcatcga      2880
cttcaaggag gacggcaaca tcctggggca caagctggag tacaactaca acagccacaa      2940
cgtctatatc atggccgaca agcagaagaa cggcatcaag gtgaacttca gatccgcca      3000 caacatcgag gacggcagcg tgcagctcgc cgaccactac cagcagaaca cccccatcgg      3060
cgacggcccc gtgctgctgc ccgacaacca ctacctgagc acccagtccg ccctgagcaa      3120
agaccccaac gagaagcgcg atcacatggt cctgctggag ttcgtgaccg ccgcgggat      3180 cactctcggc atggacgagc tgtacaagaa gttgttcact cagaccatga aggcgtgga      3240 acgcctggcc gtcatgggag acaccgcctg ggatttcagc tccgctggag ggttcttcac      3300
ttcggttggg aaaggaattc atacggtgtt tggctctgcc tttcagggc tatttggcgg      3360 cttgaactgg ataacaaagg tcatcatggg ggcggtactt atatggttg catcaacac      3420 aagaaacatg acaatgtcca tgagcatgat cttggtagga gtgatcatga tgtttttgtc      3480
tctaggagtt ggcgccgatc aaggatgcgc catcaacttt ggcaagagag agctcaagtg      3540
cggagatggt atcttcatat ttagagactc tgatgactgg ctgaacaagt actcatacta      3600
tccagaagat cctgtgaagc ttgcatcaat agtgaaagcc tctttcgaag aagggaagtg      3660
tggcctaaat tcagttgact cccttgagca tgagatgtgg agaagcaggg cagatgagat      3720 taatacccatt tttgaggaaa acgaggtgga catttctgtt gtcgtgcagg atccaaagaa      3780
tgtttaccag agaggaactc atccattttc cagaattcgg gatggtctgc agtatggttg      3840
```

```
gaagacttgg ggtaagaacc ttgtgttctc cccagggagg aagaatgaa gcttcatcat    3900
agatggaaag tccaggaaag aatgcccgtt ttcaaaccgg gtctggaatt ctttccagat    3960
agaggagttt gggacgggag tgttcaccac acgcgtgtac atggacgcag tctttgaata    4020
caccatagac tgcgatggat ctatcttggg tgcagcggtg aacggaaaaa agagtgccca    4080
tggctctcca acattttgga tgggaagtca tgaagtaaat gggacatgga tgatccacac    4140
cttggaggca ttagattaca aggagtgtga gtggccactg acacatacga ttggaacatc    4200
agttgaagag agtgaaatgt tcatgccgag atcaatcgga ggcccagtta gctctcacaa    4260
tcatatccct ggatacaagg ttcagacgaa cggaccttgg atgcaggtac cactagaagt    4320
gaagagagaa gcttgcccag ggactagcgt gatcattgat ggcaactgtg atggacgggg    4380
aaaatcaacc agatccacca cggatagcgg gaaagttatt cctgaatggt gttgccgctc    4440
ctgcacaatg ccgcctgtga gcttccatgg tagtgatggg tgttggtatc ccatggaaat    4500
taggccaagg aaaacgcatg aaagccatct ggtgcgctcc tgggttacag ctggagaaat    4560
acatgctgtc ccttttggtt tggtgagcat gatgatagca atggaagtgg tcctaaggaa    4620
aagacaggga ccaaagcaaa tgttggttgg aggagtagtg ctcttgggag caatgctggt    4680
cgggcaagta actctccttg atttgctgaa actcacagtg gctgtgggat tgcatttcca    4740
tgagatgaac aatggaggag acgccatgta tatggcgttg attgctgcct tttcaatcag    4800
accagggctg ctcatcggct ttgggctcag gacccatgg agccctcggg aacgccttgt    4860
gctgacccta ggagcagcca tggtggagat tgccttgggt ggcgtgatgg gcggcctgtg    4920
gaagtatcta aatgcagttt ctctctgcat cctgacaata aatgctgttg cttctaggaa    4980
agcatcaaat accatcttgc ccctcatggc tctgttgaca cctgtcacta tggctgaggt    5040
gagacttgcc gcaatgttct tttgtgccat ggttatcata ggggtccttc accagaattt    5100
caaggacacc tccatgcaga agactatacc tctggtggcc ctcacactca catcttacct    5160
gggcttgaca caacctttt tgggcctgtg tgcatttctg gcaacccgca tatttgggcg    5220
aaggagtatc ccagtgaatg aggcactcgc agcagctggt ctagtgggag tgctggcagg    5280
actggctttt caggagatgg agaacttcct tggtccgatt gcagttggag gactcctgat    5340
gatgctggtt agcgtggctg ggagggtgga tgggctagag ctcaagaagc ttggtgaagt    5400
ttcatgggaa gaggaggcgg agatcagcgg gagttccgcc cgctatgatg tggcactcag    5460
tgaacaaggg gagttcaagc tgctttctga agagaaagtg ccatgggacc aggttgtgat    5520
gacctcgctg gccttggttg gggctgccct ccatccattt gctcttctgc tggtccttgc    5580
tgggtggctg tttcatgtca ggggagctag agaagtgggg gatgtcttgt gggatattcc    5640
cactcctaag atcatcgagg aatgtgaaca tctggaggat gggatttatg gcatattcca    5700
gtcaaccttc ttgggggcct cccagcgagg agtgggagtg gcacagggag gggtgttcca    5760
cacaatgtgg catgtcacaa gaggagcttt ccttgtcagg aatggcaaga agttgattcc    5820
atcttgggct tcagtaaagg aagaccttgt cgcctatggt ggctcatgga agttggaagg    5880
cagatgggat ggagaggaag aggtccagtt gatcgcggct gttccaggaa agaacgtggt    5940
caacgtccag acaaaaccga gcttgttcaa agtgaggaat gggggagaaa tcggggctgt    6000
cgctcttgac tatccgagtg gcacttcagg atctcctatt gttaacagga cggagaggt    6060
gattgggctg tacggcaatg gcatccttgt cggtgacaac tccttcgtgt ccgccatatc    6120
ccagactgag gtgaaggaag aaggaaagga ggagctccaa gagatcccga caatgctaaa    6180
```

```
gaaaggaatg acaactgtcc ttgattttca tcctggagct gggaagacaa gacgtttcct    6240
cccacagatc ttggccgagt gcgcacggag acgcttgcgc actcttgtgt tggccccccac   6300 cagggttgtt ctttctgaaa tgaaggaggc ttttcacggc ctggacgtga aattccacac    6360
acaggctttt tccgctcacg gcagcgggag agaagtcatt gatgccatgt gccatgccac    6420
cctaacttac aggatgttgg aaccaactag ggttgttaac tgggaagtga tcattatgga    6480
tgaagcccat ttttggatc cagctagcat agccgctaga ggttgggcag cgcacagagc      6540
tagggcaaat gaaagtgcaa caatcttgat gacagccaca ccgcctggga ctagtgatga    6600
atttccacat tcaaatggtg aaatagaaga tgttcaaacg gacataccca gtgagccctg    6660
gaacacaggg catgactgga tcctggctga caaaaggccc acggcatggt tccttccatc    6720
catcagagct gcaaatgtca tggctgcctc tttgcgtaag gctggaaaga gtgtggtggt    6780
cctgaacagg aaaacctttg agagagaata ccccacgata aagcagaaga aacctgactt    6840
tatattggcc actgacatag ctgaaatggg agccaacctt tgcgtggagc gagtgctgga    6900
ttgcaggacg gcttttaagc ctgtgcttgt ggatgaaggg aggaaggtgg caataaaagg    6960
gccacttcgt atctccgcat cctctgctgc tcaaaggagg gggcgcattg ggagaaatcc    7020
caacagagat ggagactcat actactattc tgagcctaca agtgaaaata atgcccacca    7080
cgtctgctgg ttgaggcct caatgctctt ggacaacatg gaggtgaggg gtggaatggt    7140
cgccccactc tatggcgttg aaggaactaa acaccagtt tcccctggtg aaatgagact    7200
gagggatgac cagaggaaag tcttcagaga actagtgagg aattgtgacc tgcccgtttg    7260
gctttcgtgg caagtggcca aggctggttt gaagacgaat gatcgtaagt ggtgttttga    7320
aggccctgag gaacatgaga tcttgaatga cagcggtgaa acagtgaagt gcagggctcc   7380
tggaggagca aagaagcctc tgcgcccaag gtggtgtgat gaaagggtgt catctgacca    7440
gagtgcgctg tctgaattta ttaagtttgc tgaaggtagg aggggagctg ctgaagtgct    7500
agttgtgctg agtgaactcc ctgatttcct ggctaaaaaa ggtggagagg caatggatac    7560
catcagtgtg ttcctccact ctgaggaagg ctctagggct taccgcaatg cactatcaat    7620
gatgcctgag gcaatgacaa tagtcatgct gtttatactg gctggactac tgacatcggg    7680
aatggtcatc tttttcatgt ctcccaaagg catcagtaga atgtctatgg cgatgggcac    7740 aatgccggc tgtggatatc tcatgttcct tggaggcgtc aaacccactc acatctccta     7800
tgtcatgctc atattctttg tcctgatggt ggttgtgatc cccgagccag gcaacaaag    7860 gtccatccaa gacaaccaag tggcatacct cattattggc atcctgacgc tggtttcagc    7920
ggtggcagcc aacgagctag gcatgctgga gaaaaccaaa gaggacctct ttgggaagaa   7980
gaacttaatt ccatcagtg cttcaccctg gagttggccg gatcttgacc tgaagccagg    8040
agctgcctgg acagtgtacg ttggcattgt tacaatgctc tctccaatgt tgcaccactg    8100
gatcaaagtc gaatatggca acctgtctct gtctggaata gcccagtcag cctcagtcct   8160
ttctttcatg gacaagggga taccattcat gaagatgaat atctcggtca taatgctgct    8220
ggtcagtggc tggaattcaa taacagtgat gcctctgctc tgtggcatag ggtgcgccat    8280
gctccactgg tctctcatttt tacctggaat caaagcgcag cagtcaaagc ttgcacagag   8340
aagggtgttc catggcgttg ccaagaaccc tgtggttgat gggaatccaa cagttgacat    8400
tgaggaagct cctgaaatgc ctgccсcttta tgagaagaaa ctggctctat atctccttct    8460
tgctctcagc ctagcttctg ttgccatgtg cagaacgccc ttttcattgg ctgaaggcat    8520
tgtcctagca tcagctgcct tagggccgct catagaggga aacaccagcc ttctttggaa    8580
```

```
tggacccatg gctgtctcca tgacaggagt catgaggggg aatcactatg cttttgtggg   8640
agtcatgtac aatctatgga agatgaaaac tggacgccgg gggagcgcga atggaaaaac   8700
tttgggtgaa gtctggaaga gggaactgaa tctgttggac aagcgacagt ttgagttgta   8760
taaaaggacc gacattgtgg aggtggatcg tgatacggca cgcaggcatt tggccgaagg   8820
gaaggtggac accggggtgg cggtctccag ggggaccgca aagttaaggt ggttccatga   8880
gcgtggctat gtcaagctgg aaggtagggt gattgacctg gggtgtggcc gcggaggctg   8940
gtgttactac gctgctgcgc aaaaggaagt gagtggggtc aaaggattta ctcttggaag   9000
agacggccat gagaaaccca tgaatgtgca aagtctggga tggaacatca tcaccttcaa   9060
ggacaaaact gatatccacc gcctagaacc agtgaaatgt gacacccttt tgtgtgacat   9120
tggagagtca tcatcgtcat cggtcacaga ggggaaagg  accgtgagag ttcttgatac   9180
tgtagaaaaa tggctggctt gtggggttga caacttctgt gtgaaggtgt tagctccata   9240
catgccagat gttcttgaga aactggaatt gctccaaagg aggtttggcg gaacagtgat   9300
caggaaccct ctctccagga attccactca tgaaatgtac tacgtgtctg gagcccgcag   9360
caatgtcaca tttactgtga accaaacatc ccgcctcctg atgaggagaa tgaggcgtcc   9420
aactggaaaa gtgaccctgg aggctgacgt catcctccca attgggacac gcagtgttga   9480
gacagacaag ggaccctgg  acaaagaggc catagaagaa agggttgaga ggataaaatc   9540
tgagtacatg acctcttggt tttatgacaa tgacaacccc tacaggacct ggcactactg   9600
tggctcctat gtcacaaaaa cctcaggaag tgcggcgagc atggtaaatg gtgttattaa   9660
aattctgaca tatccatggg acaggataga ggaggtcacc agaatggcaa tgactgacac   9720 aaccccttt  ggacagcaaa gagtgtttaa agaaaaagtt gacaccagag caaaggatcc   9780
accagcggga actaggaaga tcatgaaagt tgtcaacagg tggctgttcc gccacctggc   9840
cagagaaaag agcccagac  tgtgcacaaa ggaagaattt attgcaaaag tccgaagtca   9900
tgcagccatt ggagcttacc tggaagaaca agaacagtgg aagactgcca atgaggctgt   9960
ccaagaccca aagttctggg aactggtgga tgaagaaagg aagctgcacc aacaaggcag   10020
gtgtcggact tgtgtgtaca acatgatggg gaaagagag  aagaagctgt cagagtttgg   10080
gaaagcaaag ggaagccgtg ccatatggta tatgtggctg ggagcgcggt atcttgagtt   10140
tgaggccctg ggattcctga atgaggacca ttgggcttcc agggaaaact caggaggagg   10200
agtggaaggc attggcttac aatacctagg atatgtgatc agagaccto  ctgcaatgga   10260 tggtggtgga ttctacgcgg atgacaccgc tggatgggac acgcgcatca cagaggcaga   10320
ccttgatgat gaacaggaga tcttgaacta catgagccca catcacaaaa aactggcaca   10380
agcagtgatg gaaatgacat acaagaacaa agtggtgaaa gtgttgagac agcccccagg   10440
agggaaagcc tacatggatg tcataggtcg acgagaccag agaggatccg gcaggtagt   10500 gacttatgct ctgaacacca tcaccaactt gaaagtccaa ttgatcagaa tggcagaagc   10560
agagatggtg atacatcacc aacatgttca agattgtgat gaatcagttc tgaccaggct   10620
ggaggcatgg ctcactgagc acggatgtaa cagactgaag aggatggcgg tgagtggaga   10680
cgactgtgtg gtccggccca tcgatgacag gttcggcctg gccctgtccc atctcaacgc   10740
catgtccaag gttagaaagg acatatctga atggcagcca tcaaaagggt ggaatgattg   10800
ggagaatgtg cccttctgtt cccaccactt ccatgaacta cagctgaagg atggcaggag   10860
gattgtggtg ccttgccgag aacaggacga gctcattggg agaggaaggg tgtctccagg   10920
```

```
aaacggctgg atgatcaagg aaacagcttg cctcagcaaa gcctatgcca acatgtggtc  10980
actgatgtat tttcacaaaa gggacatgag gctactgtca ttggctgttt cctcagctgt  11040
tcccacctca tgggttccac aaggacgcac aacatggtcg attcatggga aaggggagtg  11100
gatgaccacg gaagacatgc ttgaggtgtg gaacagagta tggataacca acaacccaca  11160
catgcaggac aagacaatgg tgaaaaaatg gagagatgtc ccttatctaa ccaagagaca  11220
agacaagctg tgcggatcac tgattggaat gaccaatagg gccacctggg cctcccacat  11280
ccatttagtc atccatcgta tccgaacgct gattggacag gagaaataca ctgactacct  11340
aacagtcatg gacaggtatt ctgtggatgc tgacctgcaa ctgggtgagc ttatctgaaa  11400
caccatctaa caggaataac cgggatacaa accacgggtg gagaaccgga ctccccacaa  11460
cctgaaaccg ggatataaac cacggctgga gaaccgggct ccgcacttaa aatgaaacag  11520
aaaccgggat aaaaactacg gatggagaac cggactccac acattgagac agaagaagtt  11580
gtcagcccag aaccccacac gagttttgcc actgctaagc tgtgaggcag tgcaggctgg  11640
gacagccgac ctccaggttg cgaaaaacct ggtttctggg acctcccacc ccagagtaaa  11700
aagaacggag cctccgctac caccctccca cgtggtggta gaaagacggg gtctagaggt  11760
tagaggagac cctccaggga acaaatagtg ggaccatatt gacgccaggg aaagaccgga  11820
gtggttctct gcttttcctc cagaggtctg tgagcacagt ttgctcaaga ataagcagac  11880
ctttggatga caaacacaaa accac                                         11905
```

<210> SEQ ID NO 24
<211> LENGTH: 19
<212> TYPE: DNA
<213> ORGANISM: Dengue 4 virus

<400> SEQUENCE: 24

```
catggacagc aggagcaga                                                   19
```

<210> SEQ ID NO 25
<211> LENGTH: 198
<212> TYPE: DNA
<213> ORGANISM: Yellow fever virus

<400> SEQUENCE: 25

```
acttcggttg ggaaaggaat tcatacggtg tttggctctg cctttcaggg gctatttggc     60
ggcttgaact ggataacaaa ggtcatcatg gggcggtac ttatatgggt tggcatcaac    120
acaagaaaca tgacaatgtc catgagcatg atcttggtag gagtgatcat gatgtttttg    180
tctctaggag ttggcgcc                                                   198
```

<210> SEQ ID NO 26
<211> LENGTH: 66
<212> TYPE: PRT
<213> ORGANISM: Yellow fever virus

<400> SEQUENCE: 26

```
Thr Ser Val Gly Lys Gly Ile His Thr Val Phe Gly Ser Ala Phe Gln
1               5                   10                  15

Gly Leu Phe Gly Gly Leu Asn Trp Ile Thr Lys Val Ile Met Gly Ala
            20                  25                  30

Val Leu Ile Trp Val Gly Ile Asn Thr Arg Asn Met Thr Met Ser Met
        35                  40                  45

Ser Met Ile Leu Val Gly Val Ile Met Met Phe Leu Ser Leu Gly Val
    50                  55                  60
```

Gly Ala
65

<210> SEQ ID NO 27
<211> LENGTH: 50
<212> TYPE: DNA
<213> ORGANISM: recombinant yellow fever virus

<400> SEQUENCE: 27
ccgtatgaat tcctttccca accgaagtct tgtacagctc gtccatgccg         50

<210> SEQ ID NO 28
<211> LENGTH: 50
<212> TYPE: DNA
<213> ORGANISM: recombinant yellow fever virus

<400> SEQUENCE: 28
cggcatggac gagctgtaca agacttcggt tgggaaagga attcatacgg         50

<210> SEQ ID NO 29
<211> LENGTH: 939
<212> TYPE: DNA
<213> ORGANISM: recombinant yellow fever virus

<400> SEQUENCE: 29
gatcaaggat gcgccatcaa ctttggcgtg agcaagggcg aggagctgtt caccggggtg        60
gtgcccatcc tggtcgagct ggacggcgac gtaaacggcc acaagttcag cgtgtccggc       120
gagggcgagg gcgatgccac ctacggcaag ctgaccctga agttcatctg caccaccggc       180
aagctgcccg tgccctggcc caccctcgtg accaccctga cctacggcgt gcagtgcttc       240
agccgctacc ccgaccacat gaagcagcac gacttcttca gtccgccat gcccgaaggc       300
tacgtccagg agcgcaccat cttcttcaag gacgacggca actacaagac ccgcgccgag       360
gtgaagttcg agggcgacac cctggtgaac cgcatcgagc tgaagggcat cgacttcaag       420
gaggacggca acatcctggg gcacaagctg gagtacaact acaacagcca caacgtctat       480
atcatggccg acaagcagaa gaacggcatc aaggtgaact tcaagatccg ccacaacatc       540
gaggacggca gcgtgcagct cgccgaccac taccagcaga caccccccat cggcgacggc       600
cccgtgctgc tgcccgacaa ccactacctg agcacccagt ccgccctgag caaagacccc       660
aacgagaagc gcgatcacat ggtcctgctg gagttcgtga ccgccgccgg gatcactctc       720
ggcatggacg agctgtacaa gacttcggtt gggaaaggaa ttcatacggt gtttggctct       780
gcctttcagg ggctatttgg cggcttgaac tggataacaa aggtcatcat ggggggcggta       840
cttatatggg ttggcatcaa cacaagaaac atgacaatgt ccatgagcat gatcttggta       900
ggagtgatca tgatgttttt gtctctagga gttggcgcc              939

<210> SEQ ID NO 30
<211> LENGTH: 313
<212> TYPE: PRT
<213> ORGANISM: recombinant yellow fever virus

<400> SEQUENCE: 30

Asp Gln Gly Cys Ala Ile Asn Phe Gly Val Ser Lys Gly Glu Glu Leu
1               5                   10                  15

Phe Thr Gly Val Val Pro Ile Leu Val Glu Leu Asp Gly Asp Val Asn
            20                  25                  30

Gly His Lys Phe Ser Val Ser Gly Glu Gly Glu Gly Asp Ala Thr Tyr

```
                    35                  40                  45
Gly Lys Leu Thr Leu Lys Phe Ile Cys Thr Thr Gly Lys Leu Pro Val
 50                  55                  60

Pro Trp Pro Thr Leu Val Thr Thr Leu Thr Tyr Gly Val Gln Cys Phe
 65                  70                  75                  80

Ser Arg Tyr Pro Asp His Met Lys Gln His Asp Phe Phe Lys Ser Ala
                 85                  90                  95

Met Pro Glu Gly Tyr Val Gln Glu Arg Thr Ile Phe Phe Lys Asp Asp
            100                 105                 110

Gly Asn Tyr Lys Thr Arg Ala Glu Val Lys Phe Glu Gly Asp Thr Leu
        115                 120                 125

Val Asn Arg Ile Glu Leu Lys Gly Ile Asp Phe Lys Glu Asp Gly Asn
130                 135                 140

Ile Leu Gly His Lys Leu Glu Tyr Asn Tyr Asn Ser His Asn Val Tyr
145                 150                 155                 160

Ile Met Ala Asp Lys Gln Lys Asn Gly Ile Lys Val Asn Phe Lys Ile
                165                 170                 175

Arg His Asn Ile Glu Asp Gly Ser Val Gln Leu Ala Asp His Tyr Gln
            180                 185                 190

Gln Asn Thr Pro Ile Gly Asp Gly Pro Val Leu Leu Pro Asp Asn His
        195                 200                 205

Tyr Leu Ser Thr Gln Ser Ala Leu Ser Lys Asp Pro Asn Glu Lys Arg
    210                 215                 220

Asp His Met Val Leu Leu Glu Phe Val Thr Ala Ala Gly Ile Thr Leu
225                 230                 235                 240

Gly Met Asp Glu Leu Tyr Lys Thr Ser Val Gly Lys Gly Ile His Thr
                245                 250                 255

Val Phe Gly Ser Ala Phe Gln Gly Leu Phe Gly Gly Leu Asn Trp Ile
            260                 265                 270

Thr Lys Val Ile Met Gly Ala Val Leu Ile Trp Val Gly Ile Asn Thr
        275                 280                 285

Arg Asn Met Thr Met Ser Met Ser Met Ile Leu Val Gly Val Ile Met
    290                 295                 300

Met Phe Leu Ser Leu Gly Val Gly Ala
305                 310

<210> SEQ ID NO 31
<211> LENGTH: 16
<212> TYPE: PRT
<213> ORGANISM: Yellow fever virus

<400> SEQUENCE: 31

Leu Ser Leu Gly Val Gly Ala Asp Gln Gly Cys Ala Ile Asn Phe Gly
  1               5                  10                  15

<210> SEQ ID NO 32
<211> LENGTH: 16
<212> TYPE: PRT
<213> ORGANISM: Japanese encephalitis virus

<400> SEQUENCE: 32

Leu Ala Thr Asn Val His Ala Asp Thr Gly Cys Ala Ile Asp Ile Thr
  1               5                  10                  15

<210> SEQ ID NO 33
<211> LENGTH: 16
<212> TYPE: PRT
```

```
<213> ORGANISM: Dengue virus type 2

<400> SEQUENCE: 33

Leu Gly Val Met Val Gln Ala Asp Ser Gly Cys Val Val Ser Trp Lys
1               5                   10                  15

<210> SEQ ID NO 34
<211> LENGTH: 16
<212> TYPE: PRT
<213> ORGANISM: Dengue virus type 4

<400> SEQUENCE: 34

Leu Gly Phe Thr Val Gln Ala Asp Met Gly Cys Val Ala Ser Trp Ser
1               5                   10                  15

<210> SEQ ID NO 35
<211> LENGTH: 16
<212> TYPE: PRT
<213> ORGANISM: West Nile virus

<400> SEQUENCE: 35

Leu Ser Val Asn Val His Ala Asp Thr Gly Cys Ala Ile Asp Ile Gly
1               5                   10                  15

<210> SEQ ID NO 36
<211> LENGTH: 16
<212> TYPE: PRT
<213> ORGANISM: Tick-borne encephalitis virus

<400> SEQUENCE: 36

Met Thr Leu Gly Val Gly Ala Asp Val Gly Cys Ala Val Asp Thr Glu
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: Designed peptide based on consense motif of
      flavivirus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 37

Val Xaa Ala Asp Xaa Gly Cys
1               5

<210> SEQ ID NO 38
<211> LENGTH: 96
<212> TYPE: PRT
<213> ORGANISM: Tick-borne encephalitis virus
<220> FEATURE:
<221> NAME/KEY: misc_feature
<223> OTHER INFORMATION: C-TERMINAL OF E PROTEIN OF TICK-BORNE
      ENCEPHALITIS VIRUS

<400> SEQUENCE: 38

Arg Val Phe Gln Lys Thr Lys Lys Gly Ile Glu Arg Leu Thr Val Ile
1               5                   10                  15

Gly Glu His Ala Trp Asp Phe Gly Ser Ala Gly Gly Phe Leu Ser Ser
                20                  25                  30
```

```
Ile Gly Lys Ala Val His Thr Val Leu Gly Gly Ala Phe Asn Ser Ile
            35                  40                  45

Phe Gly Gly Val Gly Phe Leu Pro Lys Leu Leu Leu Gly Val Ala Leu
    50                  55                  60

Ala Trp Leu Gly Leu Asn Met Arg Asn Pro Thr Met Ser Met Ser Phe
65                  70                  75                  80

Leu Leu Ala Gly Gly Leu Val Leu Ala Met Thr Leu Gly Val Gly Ala
                85                  90                  95

<210> SEQ ID NO 39
<211> LENGTH: 96
<212> TYPE: PRT
<213> ORGANISM: Yellow fever virus
<220> FEATURE:
<221> NAME/KEY: misc_feature
<223> OTHER INFORMATION: C-TERMINAL OF E PROTEIN OF YELLOW FEVER VIRUS

<400> SEQUENCE: 39

Lys Leu Phe Thr Gln Thr Met Lys Gly Val Glu Arg Leu Ala Val Met
1               5                   10                  15

Gly Asp Thr Ala Trp Asp Phe Ser Ser Ala Gly Gly Phe Phe Thr Ser
            20                  25                  30

Val Gly Lys Gly Ile His Thr Val Phe Gly Ser Ala Phe Gln Gly Leu
        35                  40                  45

Phe Gly Gly Leu Asn Trp Ile Thr Lys Val Ile Met Gly Ala Val Leu
    50                  55                  60

Ile Trp Val Gly Ile Asn Thr Arg Asn Met Thr Met Ser Met Ser Met
65                  70                  75                  80

Ile Leu Val Gly Val Ile Met Met Phe Leu Ser Leu Gly Val Gly Ala
                85                  90                  95

<210> SEQ ID NO 40
<211> LENGTH: 9
<212> TYPE: PRT
<213> ORGANISM: Yellow fever virus
<220> FEATURE:
<221> NAME/KEY: misc_feature
<223> OTHER INFORMATION: N-TERMINAL OF NS1 PROTEIN OF YELLOW FEVER VIRUS

<400> SEQUENCE: 40

Asp Gln Gly Cys Ala Ile Asn Phe Gly
1               5

<210> SEQ ID NO 41
<211> LENGTH: 9
<212> TYPE: PRT
<213> ORGANISM: Japanese encephalitis virus
<220> FEATURE:
<221> NAME/KEY: misc_feature
<223> OTHER INFORMATION: N-TERMINAL OF NS1 PROTEIN OF JAPANESE
      ENCEPHALITIS VIRUS

<400> SEQUENCE: 41

Asp Thr Gly Cys Ala Ile Asp Ile Thr
1               5

<210> SEQ ID NO 42
<211> LENGTH: 9
<212> TYPE: PRT
<213> ORGANISM: Dengue virus type 2
<220> FEATURE:
<221> NAME/KEY: misc_feature
<223> OTHER INFORMATION: N-TERMINAL OF NS1 PROTEIN OF DENGUE 2 VIRUS
```

```
<400> SEQUENCE: 42

Asp Ser Gly Cys Val Val Ser Trp Lys
1               5

<210> SEQ ID NO 43
<211> LENGTH: 9
<212> TYPE: PRT
<213> ORGANISM: Dengue virus type 4
<220> FEATURE:
<221> NAME/KEY: misc_feature
<223> OTHER INFORMATION: N-TERMINAL OF NS1 PROTEIN OF DENGUE 4 VIRUS

<400> SEQUENCE: 43

Asp Met Gly Cys Val Ala Ser Trp Ser
1               5

<210> SEQ ID NO 44
<211> LENGTH: 9
<212> TYPE: PRT
<213> ORGANISM: West Nile virus
<220> FEATURE:
<221> NAME/KEY: misc_feature
<223> OTHER INFORMATION: N-TERMINAL OF NS1 PROTEIN OF WEST NILE VIRUS

<400> SEQUENCE: 44

Asp Thr Gly Cys Ala Ile Asp Ile Gly
1               5

<210> SEQ ID NO 45
<211> LENGTH: 9
<212> TYPE: PRT
<213> ORGANISM: Tick-borne encephalitis virus
<220> FEATURE:
<221> NAME/KEY: misc_feature
<223> OTHER INFORMATION: N-TERMINAL OF NS1 PROTEIN OF TICK BORNE VIRUS

<400> SEQUENCE: 45

Asp Val Gly Cys Ala Val Asp Thr Glu
1               5

<210> SEQ ID NO 46
<211> LENGTH: 32
<212> TYPE: PRT
<213> ORGANISM: Yellow fever virus
<220> FEATURE:
<221> NAME/KEY: misc_feature
<223> OTHER INFORMATION: AMINO ACID RESIDUES CORRESPONDING TO THE 23
      AMINO ACID OF THE CARBOXI END OF YELLOW FEVER VIRUS E PROTEIN AND
      THE 9 N-TERMINAL AMINO ACID RESIDUES OF YELLOW FEVER NS1 PROTEIN
      TOTAL OF 32 RESIDUES

<400> SEQUENCE: 46

Met Thr Met Ser Met Ser Met Ile Leu Val Gly Val Ile Met Met Phe
1               5                   10                  15

Leu Ser Leu Gly Val Gly Ala Asp Gln Gly Cys Ala Ile Asn Phe Gly
            20                  25                  30

<210> SEQ ID NO 47
<211> LENGTH: 375
<212> TYPE: PRT
<213> ORGANISM: Yellow fever virus
<220> FEATURE:
<221> NAME/KEY: misc_feature
<223> OTHER INFORMATION: RECOMBINANT POLYPROTEIN REGION (375 AMINO ACID
      RESIDUES) ENCOMPASSING THE LAST 23 RESIDUES OF YF E PROTEIN, THE
      RECOMBINANT GFP PROTEIN (343 AMINO ACID RESIDUES) AND THE
      N-TERMINAL OF YF NS1 PROTEIN (9 AMINO ACID RESIDUES)
```

<400> SEQUENCE: 47

Met Thr Met Ser Met Ser Met Ile Leu Val Gly Val Ile Met Met Phe
1               5                   10                  15
Leu Ser Leu Gly Val Gly Ala Asp Gln Gly Cys Ala Ile Asn Phe Gly
            20                  25                  30
Val Ser Lys Gly Glu Glu Leu Phe Thr Gly Val Val Pro Ile Leu Val
        35                  40                  45
Glu Leu Asp Gly Asp Val Asn Gly His Lys Phe Ser Val Ser Gly Glu
    50                  55                  60
Gly Glu Gly Asp Ala Thr Tyr Gly Lys Leu Thr Leu Lys Phe Ile Cys
65                  70                  75                  80
Thr Thr Gly Lys Leu Pro Val Pro Trp Pro Thr Leu Val Thr Thr Leu
                85                  90                  95
Thr Tyr Gly Val Gln Cys Phe Ser Arg Tyr Pro Asp His Met Lys Gln
            100                 105                 110
His Asp Phe Phe Lys Ser Ala Met Pro Glu Gly Tyr Val Gln Glu Arg
        115                 120                 125
Thr Ile Phe Phe Lys Asp Asp Gly Asn Tyr Lys Thr Arg Ala Glu Val
    130                 135                 140
Lys Phe Glu Gly Asp Thr Leu Val Asn Arg Ile Glu Leu Lys Gly Ile
145                 150                 155                 160
Asp Phe Lys Glu Asp Gly Asn Ile Leu Gly His Lys Leu Glu Tyr Asn
                165                 170                 175
Tyr Asn Ser His Asn Val Tyr Ile Met Ala Asp Lys Gln Lys Asn Gly
            180                 185                 190
Ile Lys Val Asn Phe Lys Ile Arg His Asn Ile Glu Asp Gly Ser Val
        195                 200                 205
Gln Leu Ala Asp His Tyr Gln Gln Asn Thr Pro Ile Gly Asp Gly Pro
    210                 215                 220
Val Leu Leu Pro Asp Asn His Tyr Leu Ser Thr Gln Ser Ala Leu Ser
225                 230                 235                 240
Lys Asp Pro Asn Glu Lys Arg Asp His Met Val Leu Leu Glu Phe Val
                245                 250                 255
Thr Ala Ala Gly Ile Thr Leu Gly Met Asp Glu Leu Tyr Lys Lys Leu
            260                 265                 270
Phe Thr Gln Thr Met Lys Gly Val Glu Arg Leu Ala Val Met Gly Asp
        275                 280                 285
Thr Ala Trp Asp Phe Ser Ser Ala Gly Gly Phe Phe Thr Ser Val Gly
    290                 295                 300
Lys Gly Ile His Thr Val Phe Gly Ser Ala Phe Gln Gly Leu Phe Gly
305                 310                 315                 320
Gly Leu Asn Trp Ile Thr Lys Val Ile Met Gly Ala Val Leu Ile Trp
                325                 330                 335
Val Gly Ile Asn Thr Arg Asn Met Thr Met Ser Met Ser Met Ile Leu
            340                 345                 350
Val Gly Val Ile Met Met Phe Leu Ser Leu Gly Val Gly Ala Asp Gln
        355                 360                 365
Gly Cys Ala Ile Asn Phe Gly
    370                 375

METHOD FOR THE PRODUCTION OF RECOMBINANT VIRUS, DNA CONSTRUCTS, RECOMBINANT VIRUS AND VACCINE COMPOSITIONS

The present invention is related to the genetic manipulation of virus, including, but not limited to, *Flavivirus*, mainly the vaccine amarilico virus 17D strain or its derivatives; resulting in recombinant virus containing heterolog nucleotides coming from other pathogens among the genes which codify the viral proteins E and NS1. Such recombinant virus, resulting from its attenuation characteristics, immunogeneticity and genetic stability, may be applied in the development of attenuated alive vaccines to human and animal use, granting immune response not only to the Yellow Fever or any other disease caused by virus, but also to diseases caused by other pathogens.

BACKGROUND OF INVENTION

The Flaviviridae family includes three genera: *Flavivirus*, having as main representatives the virus of the yellow fever, the virus of dengue, the virus of the Japanese encephalite; the genera *Hepacivirus* (virus of hepatite C) and the genera of *Pestivirus* (virus of diarrhea bovine). Even though they belong to different genera, with distinct biological properties and without crossed serological reactivity, the virus of the 3 types share a great similarity in the viral morphology, in the genomic organization and in the replication strategy (Rice, C. M. 1996. Flaviviridae: the viruses and their replication, Third ed, vol. 1. Lippincott-Raven, Philadelphia, Pa.).

The virus of the yellow fever is the prototype of the genera *Flavivirus* from the family Flaviviridae, which includes about 70 virus. The *flavivirus* are small (40-60 nm), spherical, enclosed, with RNA genome of single strain, with the majority of these arbovirus called as such due to their transmission by arthropod-born viruses ("arthropod-borne viruses"), as mosquitoes or ticks, causing important diseases on man and animals.

FIG. 1 presents the genomic organization of the *Flavivirus* (Chambers, T. J., C. S. Hahn, R. Galler, and C. M. Rice. 1990. *Flavivirus* genome organization, expression, and replication. Annu Rev Microbiol 44:649-88). The genome is represented on the top part, with the indication of the 5' and 3' non translated sequences and the open reading phase of 10.862 nucleotides. On this reading phase, 5'→3' direction, the three structural proteins (C, prM and E) and the seven genes to the non structural proteins (NS1, NS2A, NS2B, NS3, NS4A, NS4B e NS5) are codified. The arrows indicated the proteolitic clivage sites performed by the viral protease (NS2B/NS3); and the lozenges, the cleavages by the cellular signalase (occurs inside the endoplasmatic reticule). The asterisks indicate the glycosilation sites linked to asparagines.

The yellow fever virus (FIG. 1) has a genome constituted by one single RNA molecule with 10.862 nucleotides (nt), one CAP structure at the 5' edge ($^{m7}$GpppG, to be recognized by the ribosomes), 5' region non translated short (118 nt) and a 3' edge not poliadenilated (511 nt). Such data were obtained from the first nucleotide sequencing of *flavivirus* genome— the vaccine virus vacinal 17D-204 (Rice, C. M., E. M. Lenches, S. R. Eddy, S. J. Shin, R. L. Sheets, and J. H. Strauss. 1985. Nucleotide sequence of yellow fever virus: implications for *flavivirus* gene expression and evolution. Science 229:726-33).

In the cytoplasm of the host cell, the viral RNA is used as a shape to the synthesis of the negative complementary strain, which, by its turn, will be the shape to the synthesis of more positive strains to be used in the set up of new viral particles. The replication is a semi conservative process and involves replicative intermediates, as well as replicative ways. The formation of viral particles occurs through the relationship of the viral nucleocapsid, with the envelope protein anchored on the membrane of the cellular Endoplasmatic Reticule (RER). The set up of viral particles occurs in very close association with the RER. The viral particles are carried through vesicles and, from that point, released by the exocytose through the Golgy system.

The RNA is also the viral messenger and the transduction of infected cells results in the synthesis of a polyprotein forerunner of 3.411 aminoacids, which, when proteolytically processed, create the 10 viral polypeptides. From the 5' edge, the order of genes is C; prM/M; E; NS1; NS2A; NS2B; NS3; NS4A; NS4B and NS5. The three first genes codify the structural viral proteins, that means, the ones which form the virus together with the encapsid RNA molecule, being denominated as capsid (C, 12-14 kDa), membrane (M of 8 kDa, and its forerunner prM of 18-22 kDa) and envelope (E, 52-54 kDa). These three genes are transcoded in the first quarter of the genome. The remaining genome codifies the non structural proteins (NS), numbered from 1 to 5 (NS1 a NS5), in accordance with the order of synthesis (Rice, C. M., E. M. Lenches, S. R. Eddy, S. J. Shin, R. L. Sheets, and J. H. Strauss. 1985. Nucleotide sequence of yellow fever virus: implications for *flavivirus* gene expression and evolution. Science 229:726-33).

Among the different. *Flavivirus*, three great non structural proteins have very well conserved sequences: NS1 (38-41 kDa), NS3 (68-70 kDa) and NS5 (100-103 kDa).

The first one (NS1) has an important role in the replication of the negative strand of RNA (Lindenbach, B. D., and C. M. Rice. 1999. Genetic interaction of *flavivirus* nonstructural proteins NS1 and NS4A as a determinant of replicase function. J Virol 73:4611-21; Lindenbach, B. D., and C. M. Rice. 1997. trans-Complementation of yellow fever virus NS1 reveals a role in early RNA replication. J Virol 71:9608-17; Muylaert, I. R., T. J. Chambers, R. Galler, and C. M. Rice. 1996. Mutagenesis of the N-linked glycosylation sites of the yellow fever virus NS1 protein: effects on virus replication and mouse neurovirulence. Virology 222:159-68; Muylaert, I. R., R. Galler, and C. M. Rice. 1997. Genetic analysis of the yellow fever virus NS1 protein: identification of a temperature-sensitive mutation which blocks RNA accumulation. J Virol 71:291-8). Released extracellularly as hexameric structure, may be located in the cellular surface. Antibodies against NS1 do not neutralize the viral infectivity, but exert protective immunity through mediation of the complement lyzing infected cells (Rice, C. M. 1996. Flaviviridae: the viruses and their replication, Third ed, vol. 1. Lippincott-Raven, Philadelphia, Pa.).

The second one, NS3, make up three distinct enzymatic activities: (1) protease, being responsible for the proteolytic process of the viral polyprotein in sites where the cellular protease does not act (Lee, E., C. E. Stocks, S. M. Amberg, C. M. Rice, and M. Lobigs. 2000. Mutagenesis of the signal sequence of yellow fever virus prM protein: enhancement of signalase cleavage In vitro is lethal for virus production. J Virol 74:24-32; Stocks, C. E., and M. Lobigs. 1995. Post-translational signal peptidase cleavage at the *flavivirus* C-prM junction in vitro. J Virol 69:8123-6; Yamshchikov, V. F., and R. W. Compans. 1995. Formation of the *flavivirus* envelope: role of the viral NS2B-NS3 protease. J Virol 69:1995-2003; Yamshchikov, V. F., D. W. Trent, and R. W. Compans. 1997. Upregulation of signalase processing and induction of prM-E secretion by the *flavivirus* NS2B-NS3 protease: roles of protease components. Virol 71:4364-71); (2) helicase and (3) nucleotide-trifosfatase (Gorbalenya, A. E., E. V. Koonin, A. P. Donchenko, and V. M. Blinov. 1989. Two related superfamilies of putative helicases involved in replication, recombination, repair and expression of DNA and RNA genomes. Nucleic Acids Res 17:4713-30; Wengler, G., and G. Wengler. 1993. The NS 3 nonstructural protein of *flaviviruses* contains an RNA triphosphatase activity. Virology 197:265-73; Wu, J., A. K. Sera, R. J. Kuhn, and J. L. Smith. 2005. Structure of the *Flavivirus* helicase: implications for catalytic activity, protein interactions, and proteolytic processing. J Virol 79:10268-77). The two last ones give to this protein an important role also in the replication of the viral RNA.

The third one, NS5, is the greatest and most conserved viral protein, making up the viral RNA polimerase, since its sequence contains several structural elements characteristic of RNA polymerases (Chambers, T. J., C. S. Hahn, R. Geller, and C. M. Rice. 1990. *Flavivirus* genome organization, expression, and replication. Annu Rev Microbiol 44:649-88) and still exhibits RNA polimerase activity, dependent of RNA (Steffens, S., H. J. Thiel, and S. E. Behrens. 1999. The RNA-dependent RNA polymerases of different members of the family Flaviviridae exhibit similar properties in vitro. J Gen Virol 80 (Pt 10):2583-90).

The four small proteins NS2A, NS2B, NS4A and NS4B are not enough conserved in its aminoacid sequence, but not in its patterns of multiple hydrophobic parts. These small proteins were related, up to the moment, to some processes of viral propagation: NS2A seems to be necessary to the correct processing of NS1 (Falgout, B., R. Chanock, and C. J. Lai. 1989. Proper processing of dengue virus nonstructural glycoprotein NS1 requires the N-terminal hydrophobic signal sequence and the downstream nonstructural protein NS2a. J Virol 63:1852-60) and to the set up of the viral particle together with NS3 (Kummerer, B. M., and C. M. Rice. 2002. Mutations in the yellow fever virus nonstructural protein NS2A selectively block production of infectious particles. J Virol 76:4773-84); NS2B is associated with NS3, acting as a complex proteolitic viral cofactor (Chambers, T. J., A. Nestorowicz, S. M. Amberg, and C. M. Rice. 1993. Mutagenesis of the yellow fever virus NS2B protein: effects on proteolytic processing, NS2B-NS3 complex formation, and viral replication. J Virol 67:6797-807; Falgout, B., M. Pethel, Y. M. Zhang, and C. J. Lai. 1991. Both nonstructural proteins NS2B and NS3 are required for the proteolytic processing of dengue virus nonstructural proteins. J Virol 65:2467-75; Jan, L. R., C. S. Yang, D. W. Trent, B. Falgout, and C. J. Lai. 1995. Processing of non-structural Japanese encephalitis virus proteins: NS2B-NS3 complex and heterologous proteases. J Gen Virol 76 (Pt 3):573-80); NS4A would interact with NS1, allowing its integration in the citoplasmatic process of RNA replication (Lindenbach, B. D., and C. M. Rice. 1999. Genetic interaction of *flavivirus* nonstructural proteins NS1 and NS4A as a determinant of replicase function. J Virol 73:4611-21). Considering that the synthesis of the viral RNA occurs in the cellular cytoplasm in association with membranes of RER, it is assumed that these viral hydrophobic viral proteins would be immersed in membranes and, through interactions with NS3 and NS5, they would be participating with them in complex viral replicatives.

Structural elements present in the non translated 5' and 3' edges (NTR) are also important in the replication and wrapping of the viral RNA (Chambers, T. J., C. S. Hahn, R. Galler, and C. M. Rice. 1990. *Flavivirus* genome organization, expression, and replication. Annu Rev Microbiol 44:649-88; Cologna, R., and R. Rico-Hesse. 2003. American genotype structures decrease dengue virus output from human monocytes and dendritic cells. J Virol 77:3929-38; Elghonemy, S., W. G. Davis, and M. A. Brinton. 2005. The majority of the nucleotides in the top loop of the genomic 3' terminal stem loop structure are cis-acting in a West Nile virus infectious clone. Virology 331:238-46; Hanley, K. A., L. R. Manlucu, G. G. Manipon, C. T. Hanson, S. S. Whitehead, B. R. Murphy, and J. E. Blaney, Jr. 2004. Introduction of mutations into the non-structural genes or 3' untranslated region of an attenuated dengue virus type 4 vaccine candidate further decreases replication in rhesus monkeys while retaining protective immunity. Vaccine 22:3440-8; Khromykh, A. A., H. Meka, K. J. Guyatt, and E. G. Westaway. 2001. Essential role of cyclization sequences in *flavivirus* RNA replication. J Virol 75:6719-28; Thurner, C., C. Witwer, I. L. Hofacker, and P. F. Stadler. 2004. Conserved RNA secondary structures in Flaviviridae genomes. Gen Virol 85:1113-24; Tilgner, M., T. S. Deas, and P. Y. Shi. 2005. The *flavivirus*-conserved penta-nucleotide in the 3' stem-loop of the West Nile virus genome requires a specific sequence and structure for RNA synthesis, but not for viral translation. Virology 331:375-86; Tilgner, M., and P. Y. Shi. 2004. Structure and function of the 3'terminal six nucleotides of the west nile virus genome in viral replication. J Virol 78:8159-71; Yu, L., and L. Markoff. 2005. The topology of bulges in the long stem of the *flavivirus* 3' stem-loop is a major determinant of RNA replication competence. J Virol 79:2309-24).

The protein C of the capsid interacts with the viral RNA, forming the viral nucleocapsid (Chambers, T. J., C. S. Hahn, R. Galler, and C. M. Rice. 1990. *Flavivirus* genome organization, expression, and replication. Annu Rev Microbiol 44:649-88). The protein prM is a glicosilated forerunner of the membrane protein. It is present on the surface of immature viral particles, with the cleavage by cellular proteases furina type at the level of the Golgy complex, before the release of viral particles, in such way that the mature virus contains the protein M. The role of the prM is to stabilize the protein E, avoiding the premature show off of the fusion peptide to the reduced pH found in the exocite via (Heinz, F. X., and S. L. Allison. 2003. *Flavivirus* structure and membrane fusion. Adv Virus Res 59:63-97). The retention of prM protein may affect the conformation and antigenicity of the protein E and reduce the infectivity, inhibiting the acid-dependent fusion.

On FIG. 2, the immature (intracellular form) and mature (extracellular form) viral particles of the *Flavivirus* are represented. The capsid of the virus has an icosahedra symmetry, but the shape is not necessarily the one presented on the Figure, which also shows the genome of the virus associated with the internal side of the capsid. Here are represented the envelope proteins (E) and its dimeric form, the protein of the membrane (M) and its forerunner (prM), which is still present in the envelope in an extracellular shape. Oppositely to the extracellular particles, the intracellular particles are not infective (Chambers, T. J., C. S. Hahn, R. Galler, and C. M. Rice. 1990. *Flavivirus* genome organization, expression, and replication. Annu Rev Microbiol 44:649-88).

The protein E is the main component of the viral envelope. It promotes the linkage to glicoproteic receptors on the cellular surface and the internalization by dependent fusion of pH, processes that trigger a viral infection. This protein has multiple determinant antigens and it is the main target to the immune-protective response of the vertebrate host. Therefore, it plays a key role in the cellular infections, in the viral tropism, in virulence and in the immunity.

The discovery of the three-dimensional atomic structure of the protein E of the mature viral particle of *flavivirus* TBE (tick-borne encephalitis virus), reveals that this protein exists as a homodimers, about 110 kDa, with three defined spheres, anchored by the hydrophobic carboxylic edge on the envelope surface (Rey, F. A., F. X. Heinz, C. Mandl, C. Kunz, and S. C. Harrison. 1995. The envelope glycoprotein from tick-borne encephalitis virus at 2 A resolution. Nature 375:291-8). This model has been seen applied to all *Flavivirus*, contributing mainly to the detection of antigen tracers and the study of mutations linked to the increase or decrease of virulence (Arroyo, J., F. Guirakhoo, S. Fenner, Z. X. Zhang, T. P. Monath, and T. J. Chambers. 2001. Molecular basis for attenuation of neurovirulence of a yellow fever Virus/Japanese encephalitis virus chimera vaccine (ChimeriVax-J E). J Virol 75:934-42; Guirakhoo, F., Z. Zhang, G. Myers, B. W. Johnson, K. Pugachev, R. Nichols, N. Brown, I. Levenbook, K. Draper, S. Cyrek, J. Lang, C. Fournier, B. Barrere, S. Delagrave, and T. P. Monath. 2004. A single amino acid substitution in the envelope protein of chimeric yellow fever-dengue 1 vaccine virus reduces neurovirulence for suckling mice and viremia/viscerotropism for monkeys. J Virol 78:9998-10008; Halstead, S. B., F. X. Heinz, A. D. Barrett, and J. T. Roehrig. 2005. Dengue virus: molecular basis of cell entry and pathogenesis, 25-27 Jun. 2003, Vienna, Austria. Vaccine 23:849-56; Hurrelbrink, R. J., and P. C. McMinn. 2003. Molecular determinants of virulence: the structural and functional basis for *flavivirus* attenuation. Adv Virus Res 60:1-42; Kolaskar, A. S., and U. Kulkarni-Kale. 1999. Prediction of three-dimensional structure and mapping of conformational epitopes of envelope glycoprotein of Japanese encephalitis virus. Virology 261:31-42; Lee, E., R. A. Hall, and M. Lobigs. 2004. Common E protein determinants for attenuation of glycosaminoglycan-binding variants of Japanese encephalitis and West Nile viruses. J Virol 78:8271-80; Lee, E., and M. Lobigs. 2000. Substitutions at the putative receptor-binding site of an encephalitic *flavivirus* alter virulence and host cell tropism and reveal a role for glycosaminoglycans in entry. J Virol 74:8867-75; Lee, E., C. E. Stocks, S. M. Amberg, C. M. Rice, and M. Lobigs. 2000. Mutagenesis of the signal sequence of yellow fever virus prM protein: enhancement of signalase cleavage In vitro is lethal for virus production. J Virol 74:24-32; Mandl, C. W., S. L. Allison, H. Holzmann, T. Meixner, and F. X. Heinz. 2000. Attenuation of tick-borne encephalitis virus by structure-based site-specific mutagenesis of a putative *flavivirus* receptor binding site. J Virol 74:9601-9; Nickells, M., and T. J. Chambers. 2003. Neuroadapted yellow fever virus 17D: determinants in the envelope protein govern neuroinvasiveness for SCID mice. J Virol 77:12232-42; Ryman, K. D., H. Xie, T. N. Ledger, G. A. Campbell, and A. D. Barrett. 1997. Antigenic variants of yellow fever virus with an altered neurovirulence phenotype in mice. Virology 230:376-80; Shirato, K., H. Miyoshi, A. Goto, Y. Ako, T. Ueki, H. Kariwa, and I. Takashima. 2004. Viral envelope protein glycosylation is a molecular determinant of the neuroinvasiveness of the New York strain of West Nile virus. J Gen Virol 85:3637-45).

The bonding of protein E to cell receptors leads to the formation of de endocitic vesicles, covered by clatrine. After the internalization by endocitose mediated by receptor, the virus are released in the cytoplasm through conformation changes, induced by acidic pH which takes the peptide of fusion to be exposed after the trimerization of protein E (Bonaldo, M. C., R. C. Garratt, R. S. Marchevsky, E. S. Coutinho, A. V. Jabor, L. F. Almeida, A. M. Yamamura, A. S. Duarte, P. J. Oliveira, J. O. Lizeu, L. A. Camacho, M. S. Freire, and R. Galler. 2005. Attenuation of recombinant yellow fever 17D viruses expressing foreign protein epitopes at the surface. J Virol 79:8602-13; Bressanelli, S., K. Stiasny, S. L. Allison, E. A. Stura, S. Duquerroy, J. Lescar, F. X. Heinz, and F. A. Rey. 2004. Structure of a *flavivirus* envelope glycoprotein in its low-pH-induced membrane fusion conformation. Embo J 23:728-38; Heinz, F. X., and S. L. Allison. 2003. *Flavivirus* structure and membrane fusion. Adv Virus Res 59:63-97; Stiasny, K., S. Bressanelli, J. Lepault, F. A. Rey, and F. X. Heinz. 2004. Characterization of a membrane-associated trimeric low-pH-induced Form of the class II viral fusion protein E from tick-borne encephalitis virus and its crystallization. J Virol 78:3178-83).

In 1927, the virus which causes the yellow fever was isolated in the Rhesus (Macaca mulatta), through the straight inoculation of blood from an African patient named Asibi (Stokes A, B. J., Hudson N P. 1928, The transmission of yellow fever to Macacus rhesus. Rev Med. Virol. 11:141-148). After the set up of a pattern of an animal model sensitive to the virus, new perspectives showed up and the viral propagation and the clinical evaluation became possible. The Asibi virus, the original sample, is one of the most virulent among the yellow fever virus ever studied. When inoculated in monkeys, through subcutaneous via, in 4 to 7 days it caused death in 95% of the animals, and high rates of viremia are detected in the blood of theses infected animals.

The serial passage of Asibi cepa, in different types of cultivation, as described priorly, lead to the production of the parental 17D cepa, in the passage 180, to 17DD in the passage 195, and to 17D-204 cepa in the passage 204. The 17DD cepa was cultivated afterwards until the passage 243 and suffered 43 extra passages in chicken embryo (passage 286). The 17D-204 cepa, by its turn, created by cultivation, to Colombia 88 cepa, that by its turn, originated the different seed shares used in France (I. Pasteur, passage 235) and in the United States (Connaught, passage 234). The 17D-204 and 17DD virus are the two sub cepas of the 17D cepas used actually to produce vaccines in the world, which accumulated the genotype and phenotype differences due to the independent serial passages (Galler, R., P. R. Post, C. N. Santos, and Ferreira, II. 1998. Genetic variability among yellow fever virus 17D substrains. Vaccine 16:1024-8; Marchevsky, R. S., M. S. Freire, E. S. Coutinho, and R. Galler. 2003. Neurovirulence of yellow fever 17DD vaccine virus to rhesus monkeys. Virology 316:55-63; Post, P. R., R. de Carvalho, M. da Silva Freire, and R. Galler. 2001. The early use of yellow fever virus strain 17D for vaccine production in Brazil—a review. Mem Inst Oswaldo Cruz 96:849-57). However, both are equally immunogenic and safe for human vaccine (Camacho, L. A., S. G. Aguiar, M. D. Freire, M. D. Leal, J. P. Nascimento, T. Iguchi, J. A. Lozana, and R. H. Farias. 2005. Reactogenicity of yellow fever vaccines in a randomized, placebo-controlled trial. Rev Saude Publica 39:413-420; Camacho, L. A., S. Freire Mda, L. Leal Mda, S. G. Aguiar, J. P. Nascimento., T. Iguchi, A. Lozana Jde, and R. H. Farias. 2004. Immunogenicity of WHO-17D and Brazilian 17DD yellow fever vaccines: a randomized trial. Rev Saude Publica 38:671-8).

The attenuated alive virus vaccine of the yellow fever (FA) 17D strain, constitutes one of the best and safer vaccines nowadays, having a well established methodology of production and a serious quality control, including the monkey neurovirulence test. Besides, it promotes lifetime immunity (Monath, T. 2003. Yellow Fever Vaccine, 4th ed. W.B. Saunders Company, USA) and it is capable of inducing both cellular immune and humoral responses (Co, M. D., M. Terajima, J. Cruz, F. A. Ennis, and A. L. Rothman. 2002. Human cytotoxic T lymphocyte responses to live attenuated 17D yellow fever vaccine: identification of HLA-B35-restricted CTL epitopes on nonstructural proteins NS1, NS2b, NS3, and the structural protein E. Virology 293:151-63); in addition to being low cost and one single dose. Its use was estimated in 400 million doses.

Due to this, its characteristics make it appropriate for the development of 17D virus as a vaccine expression vector of the heterolog antigens.

But, for the development of the *flavivirus*, expressing heterolog antigens, it is necessary to:
(a) the sketch of strategies that allow the introduction of heterolog antigens, without compromise of the structure and replication of the virus;
(b) ensure that the construction of the cDNA (and the RNA transcripts) generate a non-pathogenic virus and moreover that the foreign sequence stays integrated in the viral genome; and
(c) guarantee that the FA recombinant virus, besides being attenuated, keeps the immunologic properties, expressing the heterolog antigens, inserted in a way that it induces the appropriated immune response. It is also important that the replication capacity in certified cells for production of vaccines is maintained.

The development of the recombinant DNA technology made it possible the progress in the studies of structure and expression of viral RNA genome. To manipulate the genomic RNA, it is necessary that the complementary DNA become available. Genetic modifications may be introduced in determined sites of the viral genome.

The pioneer study of David Baltimore (Racaniello, V. R., and D. Baltimore. 1981. Cloned poliovirus complementary DNA is infectious in mammalian cells. Science 214:916-9), was the first one to demonstrate that it possible to regenerate virus for the complementary DNA of the poliomyelitis virus. With the development of efficient systems in vitro transcription, it made it possible to the complete synthesis of viral RNA viral in vitro with efficiency much greater than the cDNA transcription in the cell. The development of efficient methods of cells transfection with nucleic acids, as for example electroporation and the use of cationic liposome's contributed to the increase of the transfection efficiency of cell transfection with RNA and viral regeneration. The basis of methodology of the infectious clone is established and has been used to obtain infectious clones to other virus of the positive strand.

The infectious clones may be used to better understand the molecular bases of diverse biological phenomena such as: the virulence, attenuation, mechanism of cell penetration, replication, relation with the host, conditional mutant and the design of mutants for the required functions (Bonaldo, M. C., P. S. Caufour, M. S. Freire, and R. Galler. 2000. The yellow fever 17D vaccine virus as a vector for the expression of foreign proteins: development of new live *flavivirus* vaccines. Mem Inst Oswaldo Cruz 95 Suppl 1:215-23; Bonaldo, M. C., R. C. Garratt, P. S. Caufour, M. S. Freire, M. M. Rodrigues, R. S. Nussenzweig, and R. Galler. 2002. Surface expression of an immunodominant malaria protein B cell epitope by yellow fever virus. J Mol Biol 315:873-85).

The construction of a complete cDNA shape of the 17D vaccine virus, that can be transcript in vitro, producing RNA infectious virus, was described for the first time by Rice and colleagues (Rice, C. M., A. Grakoui, R. Galler, and T. J. Chambers. 1989. Transcription of infectious yellow fever RNA from full-length cDNA templates produced by in vitro ligation. New Biol 1:285-96). The virus—obtained from cDNA—was indistinguished from the parental virus, the 17D-204 subcepa, by different criteria (Rice, C. M., A. Grakoui, R. Galler, and T. J. Chambers. 1989. Transcription of infectious yellow fever RNA from full-length cDNA templates produced by in vitro ligation. New Biol 1:285-96).

The acquisition of vaccines shares seeds from cDNA in good production practices was described by the first time by Marchevsky and collaborators (Marchevsky, R. S., J. Mariano, V. S. Ferreira, E. Almeida, M. J. Cerqueira, R. Carvalho, J. W. Pissurno, A. P. da Rosa, M. C. Simoes, and C. N. Santos. 1995. Phenotypic analysis of yellow fever virus derived from complementary DNA. Am J Trop Med Hyg 52:75-80), and later by Galler and Freire (patent documents U.S. Pat. No. 6,171,854 and U.S. Pat. No. 6,859,522) and Freire and collaborators (document of patent BRPI 9804283). The production process described by Freire and collaborators (patent document BRPI 9804283) may also be, in a near future, the modernization of the production of the amarilic vaccine; making it possible a significative increase in the production and improvement of the product quality (Freire, M. S., G. F. Mann, R. S. Marchevsky, A. M. Yamamura, L. F. Almeida, A. V. Jabor, J. M. Malachias, E. S. Coutinho, and R. Galler. 2005. Production of yellow fever 17DD vaccine virus in primary culture of chicken embryo fibroblasts: yields, thermo and genetic stability, attenuation and immunogenicity. Vaccine 23:2501-12).

This work created the perspective for the use of the 17D virus as an expression vector for heterolog antigens. There are several ways to obtain an expression vector from the virus with positive string RNA genome, some of which are described in published revisions by our research group (Bonaldo, M. C., P. S. Caufour, M. S. Freire, and R. Galler. 2000. The yellow fever 17D vaccine virus as a vector for the expression of foreign proteins: development of new live *flavivirus* vaccines. Mem Inst Oswaldo Cruz 95 Suppl 1:215-23; Galler, R., M. S. Freire, A. V. Jabor, and G. F. Mann. 1997. The yellow fever 17D vaccine virus: molecular basis of viral attenuation and its use as an expression vector. Braz J Med Biol Res 30:157-68).

One of the alternatives in which our research group is working refers to the substitution of the prM/E proteins of yellow fever by the equivalent proteins of the dengue virus, so it can be obtained a chimeric virus. This approach has the advantage of the previous immunity against the vector wouldn't be a limit, since the envelope E protein contains all the epitopes for viral neutralization.

The approach of change of prM/E genes among the *flavivirus* was described for the first time in the patent document U.S. Pat. No. 6,184,024 and U.S. Pat. No. 6,676,936, which described the new virus with the prM/E genes of dengue 1 or 2 and the remaining of the virus genome Den 4. The first chimeric virus from 17D genome was created by change of prM/E genes of the Japanese encephalitis virus (JE) (Chambers, T. J., A. Nestorowicz, P. W. Mason, and C. M. Rice. 1999. Yellow fever/Japanese encephalitis chimeric viruses: construction and biological properties. J Virol 73:3095-101). This Chimeric was immunogenic and attenuated in monkeys, so it could promote a total protection to these animals, in face of a intracerebral challenge (IC) with the wild JE virus (Monath, T. P., I. Levenbook, K. Soike, Z. X. Zhang, M. Ratterree, K. Draper, A. D. Barrett, R. Nichols, R. Weltzin, J. Arroyo, and F. Guirakhoo. 2000. Chimeric yellow fever virus 17D-Japanese encephalitis virus vaccine: dose-response effectiveness and extended safety testing in rhesus monkeys. J Virol 74:1742-51). Recently, a clinical study in humans demonstrated that the chimerical vaccine FA/JE is safe and immunogenic in man, in similar levels to the FA 17D, with a high possibility of use, in the future, for the prevention of the Japanese encephalitis in travelers and residents in endemic regions (Monath, T. P. 2002. Japanese encephalitis vaccines:

current vaccines and future prospects. Curr Top Microbiol Immunol 267:105-38; Monath, T. P., F. Guirakhoo, R. Nichols, S. Yoksan, R. Schrader, C. Murphy, P. Blum, S. Woodward, K. McCarthy, D. Mathis, C. Johnson, and P. Bedford. 2003. Chimeric live, attenuated vaccine against Japanese encephalitis (ChimeriVax-JE): phase 2 clinical trials for safety and immunogenicity, effect of vaccine dose and schedule, and memory response to challenge with inactivated Japanese encephalitis antigen. J Infect Dis 188:1213-30).

Our research group constituted four chimeric virus containing the cDNA of different dengue 2 cepas, and one of these constructions was selected for immunogenicity tests. Theses tests were performed in murine model, the results being published with the characterization of the growth and viral attenuation (Caufour, P. S., M. C. Motta, A. M. Yamamura, S. Vazquez, Ferreira, II, A. V. Jabor, M. C. Bonaldo, M. S. Freire, and R. Galler. 2001. Construction, characterization and immunogenicity of recombinant yellow fever 17D-dengue type 2 viruses. Virus Res 79:1-14).

In this strategy it was also used the creation of a chimeric virus FA 17D for the creation of a tetravalent vaccine against the different sorotypes of dengue virus (Guirakhoo, F., J. Arroyo, K. V. Pugachev, C. Miller, Z. X. Zhang, R. Weltzin, K. Georgakopoulos, J. Catalan, S. Ocran, K. Soike, M. Ratterree, and T. P. Monath. 2001. Construction, safety, and immunogenicity in nonhuman primates of a chimeric yellow fever-dengue virus tetravalent vaccine. J Virol 75:7290-304; Guirakhoo, F., K. Pugachev, J. Arroyo, C. Miller, Z. X. Zhang, R. Weltzin, K. Georgakopoulos, J. Catalan, S. Ocran, K. Draper, and T. P. Monath. 2002. Viremia and immunogenicity in nonhuman primates of a tetravalent yellow fever-dengue chimeric vaccine: genetic reconstructions, dose adjustment, and antibody responses against wild-type dengue virus isolates. Virology 298:146-59; Guirakhoo, F., K. Pugachev, Z. Zhang, G. Myers, I. Levenbook, K. Draper, J. Lang, S. Ocran, F. Mitchell, M. Parsons, N. Brown, S. Brandler, C. Fournier, B. Barrere, F. Rizvi, A. Travassos, R. Nichols, D. Trent, and T. Monath. 2004. Safety and efficacy of chimeric yellow Fever-dengue virus tetravalent vaccine formulations in nonhuman primates. J Virol 78:4761-75, US Patent Documents U.S. Pat. No. 6,696,281 and WO0139802). In tissue culture, these chimera grow in high degrees, and were immunogenic in inoculated monks with individual formulations and tetravalent of these recombinants. But, we may stress that a higher immune response against one of the recombinant, the chimera FA/den2, due, probably, to a grater replication rate of this virus.

An ideal vaccine against the four sorotypes, as well as inducing a long-lasting response, should protect the individual against the four sorotypes efficiently, because an incomplete immunization may unleash the sickness in its more serious form. Later, other formulations were tested in monkeys, with the intention of reducing the dominant immunogenicity of the chimera FA/Den2 (Guirakhoo, F., K. Pugachev, J. Arroyo, C. Miller, Z. X. Zhang, R. Weltzin, K. Georgakopoulos, J. Catalan, S. Ocran, K. Draper, and T. P. Monath. 2002. Viremia and immunogenicity in nonhuman primates of a tetravalent yellow fever-dengue chimeric vaccine: genetic reconstructions, dose adjustment, and antibody responses against wild-type dengue virus isolates. Virology 298:146-59). In the meantime, the adjustment of the dose for the chimera den2 resulted, in spite of a more balanced reply against the chimeric viruses types 1, 2 and 3, in a more accented reply against the chimera type 4. These results indicate that the development of a tetravalent vaccine should pass by tests with different formulations, so that an ideal adjustment may be obtained to be tested in monkeys before an optimum formulation may be attained to be used in tests of safety and immunogenicity in humans in a phase I clinical study.

The second approach refers to the insertion of the protein epitopes in the virus 17D genome of. Such insertions may be done in very immunogenic proteins of the amarilic virus, through duplication of the processing signals of the viral polyprotein by viral protease and the creation of expression cassettes—as was done with an epitope of ovalbumin, response inductor of the lymphocyte T cytotoxic, that was inserted between the genes NS2B and NS3 (McAllister, A., A. E. Arbetman, S. Mandl, C. Pena-Rossi, and R. Andino. 2000. Recombinant yellow fever viruses are effective therapeutic vaccines for treatment of murine experimental solid tumors and pulmonary metastases. J Virol 74:9197-205), Patent Documents U.S. Pat. No. 6,589,531 and US20030157128). Immunization of mice with the recombinant virus induced protection against a lethal dose of malignant melanoma cells that expressed the same epitope. It is important that the new viruses be attenuated with the vaccine 17D, that they are genetically stable and retain the immunogenic properties do heterologous antigen, promoting the correct induction of the immune response. In this sense, it should be noted that the expression of the epitope de *Plasmodium yoelii* through its insertion between the NS2B-NS3 genes of the virus 17D (Tao, D., G. Barba-Spaeth, U. Rai, V. Nussenzweig, C. M. Rice, and R. S. Nussenzweig. 2005. Yellow fever 17D as a vaccine vector for microbial CTL epitopes: protection in a rodent malaria model. J Exp Med 201:201-9).

It became interesting to test this system for the expression of larger genetic fragments. In this sense, our research group opted to insert the green fluorescent algae genes (GFP). This gene facilitates monitoring the infectiousness of the transcribed RNA in vitro, as from plasmidial molds, to allow the direct visualization of the synthesized proteins in transfected cultures through fluorescent microscopy.

The insertion strategy is described in FIG. 3, in which the upper part represents the genomic structure and the genetic expression. The *Flavivirus* genome is translated into a single polyprotein, which is cleaved by cellular proteases (↓) or viral (▼). Black vertical bars indicate transmembrane hydrophobic domains, and the asterisks indicate glycosylation sites connected to asparagine. Shadowed areas in C and prM/E represent as structural proteins present, in the mature infectious viruses. The lower part presents the general genome structure, the sequences in the cleavage sites and the proteolytic cleavages necessary for the insertion of the gene reporter between NS2A and 2B. Such strategy applies to the other sites cleaved by viral protease, situated between C-prM, NS2B-3, NS3-4A, NS4A-4B and NS4B-5.

The GFP gene was inserted between NS2A-2B and NS2B-NS3 without the recovery of the infectious virus, suggesting that the insertion of larger genetic fragments in the virus 17D genome through this approach is not possible (Bonaldo M C and Galler R, data not published).

Another manner of developing recombinant amarylic viruses having various pathogenic epitopes was the expression of protean epitopes previously classified as important in some kinds of immune replies, whether humoral or cellular, by direct insertion in the viral polyprotein. The different viral proteins contain epitopes related to the induction of the cellular reply (CTL) and humoral (formation of antibodies), in such a way that there are different possibilities of optimizing expression and immunogenicity.

A new version of the FA infectious clone was developed, containing restriction sites in the viral envelope protein gene that allowed the insertion "in-frame" of the heterologous epitopes. This was possible due to the availability of their three-dimensional structure, which allowed an analysis of the areas where insertions would be viable. A site for the insertion of the epitopes was identified in these three-dimensional analyses (f-g loop of the envelope protein), and various epitopes of different microorganisms were already inserted and expressed in the f-g loop, including epitopes de *Plasmodium* sp, dengue and arenavirus (Bonaldo, M. C., R. C. Garratt, M. S. Freire, and R. Galler. 2005. Novel *Flavivirus* vector useful for expressing heterologous antigens comprises foreign gene sequences inserted at sites in the level of its envelope protein. Great-Britain).

With relation to the *Plasmodium* sp epitopes, a total of 16 new viruses were created, which expressed epitopes related to the response by the T CD4+ or T CD8+ cells or the B cells. A repetitive humoral epitope of the CS surface protein of the sporozoite form of the *P. falciparum* was inserted in the fg loop and the virus regenerated. This virus was classified in terms of the culture growth of the cells, neutralization by soros against yellow fever and monoclonal against the epitope, this experiment proved its correct presentation in the viral surface as expected from the three-dimensional modeling, and attenuation and immunogenicity in mice (Bonaldo, M. C., R. C. Garratt, P. S. Caufour, M. S. Freire, M. M. Rodrigues, R. S. Nussenzweig, and R. Galler. 2002. Surface expression of an immunodominant malaria protein B cell epitope by yellow fever virus. J Mol Biol 315:873-85).

A recombinant Virus 17D expressing an epitope of the *P. yoelii* T CD8 cell, through insertion in the f-g loop, also was constructed. This virus did not have its growth in vitro characteristics altered, but showed itself more attenuated in the virulence test in mice than the virus vaccine 17DD. This epitope was correctly presented on the viral surface and is immunogenic, based on the results of immunization of mice and the Elispot tests and response with *P. yoelii* sporozoites, response against which was observed a protection of 70%.

Our research group also made a more detailed evaluation of the attenuation of the chimeric viruses, expressing the humoral epitopes *P. falciparum* and *P. yoelii* T CD8 through the intracerebral inoculation test in rhesus monkeys, in accordance with the requirements established by the World Health Organization for the amarilic virus vaccine. The results suggest that both the viruses are, at the minimum, as attenuated as the 17DD virus vaccine used in human vaccination. A comparative analysis of the virus envelope containing the two insertions showed that the original structural "design" of the insertion, long from the domain III involved in the connection to the receptor/tropism, was enough to not cause any alteration in the viral virulence, a fundamental aspect in the validation of this approach (Bonaldo, M. C., R. C. Garratt, R. S. Marchevsky, E. S. Coutinho, A. V. Jabor, L. F. Almeida, A. M. Yamamura, A. S. Duarte, P. J. Oliveira, J. O. Lizeu, L. A. Camacho, M. S. Freire, and R. Galler. 2005. Attenuation of recombinant yellow fever 17D viruses expressing foreign protein epitopes at the surface. J Virol 79:8602-13). This approach constitutes a recently conceded patent (Bonaldo M C, Garrat R C, Freire M S & Galler R (2001) Use of *Flaviviruses* for the expression of foreign protein epitopes and the development of new live attenuated vaccines for immunization against *Flaviviruses* and other infectious agents, GB 0105877.5 e PCT PCT/BR02/00036).

A fourth approach in the use of the 17D virus as an expression vector refers to the insertion of genes in the non translated 3' region (NTR). This approach was done a lot in function of the variability of the length of this region in the FA virus (from Filippis, A. M., R. M. Nogueira, H. G. Schatzmayr, D. S. Tavares, A. V. Jabor, S. C. Diniz, J. C. Oliveira, E. Moreira, M. P. Miagostovich, E. V. Costa, and R. Galler. 2002. Outbreak of jaundice and hemorrhagic fever in the Southeast of Brazil in 2001: detection and molecular characterization of yellow fever virus. J Med Virol 68:620-7; Mutebi, J. P., R. C. Rijnbrand, H. Wang, K. D. Ryman, E. Wang, L. D. Fulop, R. Titball, and A. D. Barrett. 2004. Genetic relationships and evolution of genotypes of yellow fever virus and other members of the yellow fever virus group within the *Flavivirus* genus based on the 3' noncoding region. J Virol 78:9652-65).

This methodology was described by Andino- and collaborators (Andino, P. R., Mcallister, M. N., 2002, Recombinant Bicistronic *Flaviviruses* and Methods of Use Thereof, WO 02/089840) and, basically, involved the creation of restriction sites for the insertion of expression modules. These modules, for their part, were constituted of a sequence derived from the enterovirus (Mengo or poliovirus) or from a Pest virus (Bovina Diarrhea virus), to which is directed the connection of the ribosomal sub-units in a manner that the translation of the heterologous gene may happen almost at the 3' NTR extremity, without needing a start in the 5' NTR region, as is characteristic of eukaryotic RNA. In this manner, the viral RNA acts as a bi-cystronic messenger, allowing the initiation of protein synthesis as from 2 RNA points, independently of the viral protein synthesis. These sequences are known as internal ribosome entry sites (IRES) Such modules vary in size, depending on the origin of the IRES and the heterologous gene to be expressed.

Figure 4:
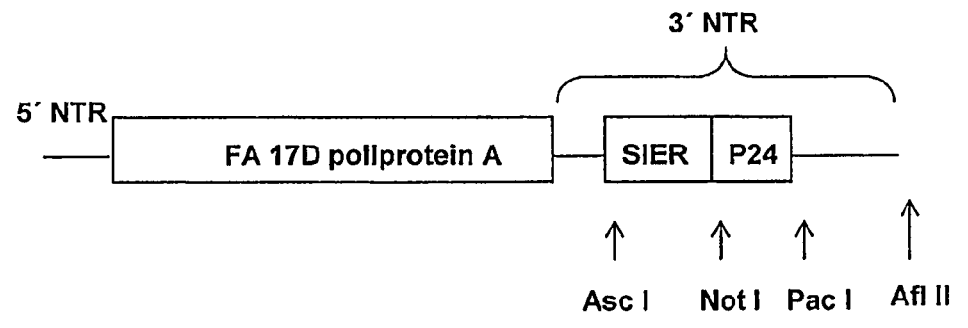

FIG. 4 represents the insertion of the heterologous sequences in the 3' NTR regions of the 17D virus. The insertions of the Mengo enterovirus IRES (569 nt) and polio (663 nt) were done through cloning in restriction sites (AscI and NotI), which are adjacent to the protein P24 (693 nt) gene sequence of the human 1 immunodeficiency virus (through the NotI and PacI enzymes). The total length of the insertions varied from 1090 to 1356 nt. The restriction sites were initially introduced, as a set (AscI, NotI and PacI), exactly 25 nucleotides after the termination codon (nucleotide 10379 as from the 5' extremity).

The transfection of the Vero in culture cells with RNA transcription in vitro, as from the cADN molds, allowed the viral regeneration referent to the constructions traced out in FIG. 3. Analysis of the resulting virus genomes, by means of nucleotide sequencing of the amplification products of this region, showed the elimination of the nucleotides. In the case of the construction with the Mengo virus IRES, the genetic instability became evident early in the first pass. The 17D-IRES-P24 virus present floating on the culture surface, presenting a cytopathic effect, had lost part of the 3' NTR region. The termination codon remained like that as well as the first 25 nucleotides that extended up to the AscI site and more than the 22 initial IRES nucleotides. 1437 nucleotides were eliminated from this point, leaving only the last 339 nucleotides (from 508) in this region of the 17D virus. In the case of the 17D-IRES-Polio-P24 virus, the genetic instability was demonstrated by the sequencing of the 3' NTR region of the virus present on the surface of the second pass in Vero cells. The termination codon remained intact in the genome of this virus and the first 19 nucleotides after it, following the elimination of a total of 1398 nucleotides, including the IRES and P24. The last 484 nucleotides of the original 17D virus 3'NTR region remained intact. This data showed that instability of the longer insertions in this genome region.

The genetic instability of insertions in the *Flavivirus* genome in the 3' NTR region is also corroborated by the data of Pierson and collaborators (Pierson, T. C., M. S. Diamond, A. A. Ahmed, L. E. Valentine, C. W. Davis, M. A. Samuel, S.

L. Hanna, B. A. Puffer, and R. W. Doms. 2005. An infectious West Nile virus that expresses a GFP reporter gene. Virology 334:28-40), to obtain the insertion of the expression modules similar to that described above, but using the GFP gene as an indicator of viral replication. Various virals isolated, analyzed after 2 passes in culture cells, led to the loss of the nucleotides that compose the IRES, as well as part do gene that codes the GFP.

The sixth possible approach in the use of the FA 17D virus for the expression of heterologous antigens refers to the development of replicons. These molecules correspond to parts of the viral genome from which the structural genes necessary for the production of viral particles were removed, although they maintained all the elements necessary for the replication of the RNA in itself. The amplification of the RNA in the transfected cells cytoplasm allows the transitory expression of heterologous genes, expression that suggests the possibility of the in vaccination (Harvey, T. J., W. J. Liu, X. J. Wang, R. Linedale, M. Jacobs, A. Davidson, T. T. Le, I. Anraku, A. Suhrbier, P. Y. Shi, and A. A. Khromykh. 2004. Tetracycline-inducible packaging cell line for production of *Flavivirus* replicon particles. J Virol 78:531-8; Khromykh, A. A. 2000. Replicon-based vectors of positive strand RNA viruses. Curr Opin Mol Ther 2:555-69; Tannis, L. L., A. Gauthier, C. Evelegh, R. Parsons, D. Nyholt, A. Khromykh; and J. L. Bramson. 2005. Semliki forest virus and Kunjin virus RNA replicons elicit comparable cellular immunity but distinct humoral immunity. Vaccine 23:4189-94; Westaway, E. G., J. M. Mackenzie, and A. A. Khromykh. 2003. Kunjin RNA replication and applications of Kunjin replicons. Adv Virus Res 59:99-140). Jones and collaborators (Jones, C. T., C. G. Patkar, and R. J. Kuhn. 2005. Construction and applications of yellow fever virus replicons. Virology 331:247-59) recently described a series of replicons based on the 17D virus genome. These replicons consist of the 17D virus genome deprived of the structural region that codifies the genes of the C-prM-E proteins (nucleotides 179 to 2382). Only the first 21 amino acids of C and the last 24 residues of E were kept. Three heterologous genes were inserted and expressed in the replicons in a manner dependent on the RNA replication, substituting the structural gene sequences. Meanwhile, no evidence of genetic stability of the heterologous genes, as well as studies on the immunogenicity of their products has been approached. The expression levels of the heterologous proteins also were not specified, in a way that use of this system for the development of new vaccines was not established. The principal applications of this expressions system, based on the 17D virus genome, are limited to studies on RNA viral replication mechanisms, RNA packaging and formation of viral particles.

It should be considered that the various methodologies described in this document for the insertion and expression of heterologous genes into recombinants *flavivirus*, as well as the object of this document, are also approaches with broad application in the expression of the whole or part of the viral genome in plasmids and DNA and RNA replicons, or even in other non-infective or infective viral systems. Khromykh, A. A., Westaway, E. G., 1997. Subgenomic replicons of the *flavivirus* Kunjin: construction and applications. J. Virol. 71 (2), 1497-1505; Kofler, R. M., Aberle, J. H., Aberle, S. W., Allison, S. L., Heinz, F. X., Mandl, C. W., 2004. Mimicking live *flavivirus* immunization with a noninfectious RNA vaccine. Proc. Natl. Acad. Sci. U.S.A. 101, 1951-1956; Aberle, J. H., Aberle, S. W., Kofler, R. M., Mandl, C. W., 2005. Humoral, and cellular immune response to RNA immunization with *flavivirus* replicons derived from tick-borne encephalitis virus. J. Virol. 79, 15107-15113; Aleshin, S. E., Timofeev, A. V., Khoretonenko, M. V., Zakharova, L. G., Pashvykina, G. V., Stephenson, J. R., Shneider, A. M., Altstein, A. D. 2005. Combined prime-boost vaccination against tick-borne encephalitis (TBE) using a recombinant vaccinia virus and a bacterial plasmid both expressing TBE virus non-structural NS1 protein. BMC Microbiology 5:45-49; Konishi, E., Kosugi, S., Imoto, J. 2006. Dengue tetravalent DNA vaccine inducing neutralizing antibody and an amnestic responses to four serotypes in mice Vaccine 24: 2200-2207; Mason, P. W., Shustov, A. V., Frolov, I. 2006). Production and characterization of vaccines based on *flaviviruses* defective in replication. Virology 351 432-443.

The seventh and last possible approach up to the moment, using the FA 17D virus as an expression vector, refers to the object of this current invention. In this case, given the impossibility of regenerating 17D viruses containing insertions longer than viral epitopes (>36 amino acids), whether in inter-genetic regions cleaved by viral protease or in the 3'NTR region, our group established a new approach for this purpose. This alternative is based on the insertion of the heterologous sequences—including, but not limited to those of the 10 to 2000 nucleotides—between the genes that code the E and NS1 proteins of the 17D virus. This approach is similar, theoretically, to the insertion between genes that code proteins cleaved by viral protease. Meanwhile, the cleavage between E and NS1 is done by a cellular enzyme (signalase) present in the endoplasmatic reticule, in such a manner that the cleavage sites and other structural elements necessary of viral viability are different, constituting a novelty in this methodology.

The endoplasmatic reticule serves as an entrance port for the proteins destined to all the compartments of the secreting via, that is, for the plasmatic membrane, the cell exterior and endocytic organelles. The majority of the membrane proteins and secreting via are co-traductionally integrated in the RE membrane, or pass by this to the RE lumen via specific membrane sites.

The addressing of the proteins to the RE is triggered by the presence of signal sequences in these proteins. The signal sequences are highly degenerated and essentially, uncharged, with a predominance of hydrophobic residues, and with an average size of 7 to 12 protein amino acids (von Heijne, G. 1990. The signal peptide. J Membr Biol 115:195-201).

In a first stage, the signal sequence is recognized, beginning to emerge from the tunnel exit of the ribosome during the proteic translation, by a signal recognition particle, of a ribonucleoproteic nature (SRP: "signal recognition particle); (Halic, M., and R. Beckmann. 2005. The signal recognition particle and its interactions during protein targeting. Curr Opin Struct Biol 15:116-25; Walter, P., and A. E. Johnson. 1994. Signal sequence recognition and protein targeting to the endoplasmic reticulum membrane. Annu Rev Cell Biol 10:87-119). Then a connection of the motif to a hydrophobic split occurs composed of a group of methionines in the SRP 54 kDa sub-unit (Keenan, R. J., D. M. Freymann, P. Walter, and R. M. Stroud. 1998. Crystal structure of the signal sequence binding subunit of the signal recognition particle. Cell 94:181-91; Lutcke, H., S. High, K. Romisch, A. J. Ashford, and B. Dobberstein. 1992. The methionine-rich domain of the 54 kDa subunit of signal recognition particle is sufficient for the interaction with signal sequences. Embo J 11:1543-51; Zopf, D., H. D. Bernstein, A. E. Johnson, and P. Walter. 1990. The methionine-rich domain of the 54 kd protein subunit of the signal recognition particle contains an RNA binding site and can be cross linked to a signal sequence. Embo J 9:4511-7). In eukaryotes, this association causes a delay in the elongation of polypeptide synthesis during the translation process. This complex connects itself to the RE membrane by a specific receptor (Keenan, R. J., D. M. Freymann, R. M. Stroud, and P. Walter. 2001. The signal recognition particle. Annu Rev Biochem 70:755-75). Both the SRP complex receptor—signal peptide and the SRP are GTPases (Egea, P. F., S. O, Shan, J. Napetschnig, D. F. Savage, P. Walter, and R. M. Stroud. 2004. Substrate twinning activates the signal recognition particle and its receptor. Nature 427:215-21; Focia, P. J., I. V. Shepotinovskaya, J. A. Seidler, and D. M. Freymann. 2004. Heterodimeric GTPase core of the SRP targeting complex. Science 303:373-7), that undergo reciprocal activation, causing the signal peptide to be released from the addressing complex and taken to the ribosome tunnel exit alignment, as to the aquatic entrance channel of the RE protein, or translocon (Beckmann, R., C. M. Spahn, N. Eswar, J. Helmers, P. A. Penczek, A. SalI, J. Frank, and G. Biobel. 2001. Architecture of the protein-conducting channel associated with the translating 80S ribosome. Cell 107:361-72; Menetret, J. F., A. Neuhof, D. G. Morgan, K. Plath, M. Radermacher, T. A. Rapoport, and C. W. Akey. 2000. The structure of ribosome-channel complexes engaged in protein translocation. Mol Cell 6:1219-32).

The translocons are comprised of various RE membrane proteins that associate themselves in such a manner as to form an aqueous pore, through which secreted proteins and domain protein lumen from the membrane pass from the cytosol to the RE (Johnson, A. E., and M. A. van Waes. 1999. The translocon: a dynamic gateway at the ER membrane. Annu Rev Cell Dev Biol 15:799-842). The translocon has an important role in the integration of the membrane proteins (Do, H., D. Falcone, 3. Lin, D. W. Andrews, and A. E. Johnson. 1996. The cotranslational integration of membrane proteins into the phospholipid bi-layer is a multi-step process. Cell 85:369-78; Heinrich, S. U., W. Mothes, J. Brunner, and T. A. Rapoport. 2000. The Sec61p complex mediates the integration of a membrane protein by allowing lipid partitioning of the transmembrane domain. Cell 102:233-44; Higy, M., T. Junne, and M. Spiess. 2004. Topogenesis of membrane proteins at the endoplasmic reticulum. Biochemistry 43:12716-22; Martoglio, B., and B. Dobberstein. 1995. Protein insertion into the membrane of the endoplasmic reticulum: the architecture of the translocation site. Cold Spring Harb Symp Quant Biol 60:41-5; Mothes, W., S. U. Heinrich, R. Graf, I. Nilsson, G. von Heijne, J. Brunner, and T. A. Rapoport. 1997. Molecular mechanism of membrane protein integration into the endoplasmic reticulum. Cell 89:523-33), therefore, in the topology of these proteins. The mechanism by which the topology of a protein is directed by the cellular translocation machinery is complex. Thus, a protein with a single membrane domain needs to translocate certain RE Lumen domains, leave others in the cytosol and guide the transmembrane segment and move the aqueous utranslocation channel to the lipidic bi-layer. Characteristics such as size and hydrophobic of the transmembrane segments, Charge distribution of the regulatory residues and size and state of the binding regulatory residues may affect the protein topology in the membrane (Beltzer, J. P., K. Fiedler, C. Fuhrer, I. Geffen, C. Handschin, H. P. Wessels, and M. Spiess. 1991. Charged residues are major determinants of the transmembrane orientation of a signal-anchor sequence. Biol Chem 266:973-8; Gafvelin, G., M. Sakaguchi, H. Andersson, and G. von Heijne. 1997. Topological rules for membrane protein assembly in eukaryotic cells. J Biol Chem 272:6119-27; Higy, M., T. Junne, and M. Spiess. 2004. Topogenesis of membrane proteins at the endoplasmic reticulum. Biochemistry 43:12716-22; Parks, G. D., and R. A. Lamb. 1991. Topology of eukaryotic type II membrane proteins: importance of N-terminal positively charged residues flanking the hydrophobic domain. Cell 64:777-87; Sakaguchi, M., R. Tomiyoshi, T. Kuroiwa, K. Mihara, and T. Omura. 1992. Functions of signal and signal-anchor sequences are determined by the balance between the hydrophobic segment and the N-terminal charge. Proc Natl Acad Sci USA 89:16-9; Spiess, M. 1995. Heads or tails—what determines the orientation of proteins in the membrane. FEBS Lett 369:76-9; von Heijne, G. 1989. Control of topology and mode of assembly of a polytopic membrane protein by positively charged residues. Nature 341:456-8; Wahlberg, J. M., and M. Spiess. 1997. Multiple determinants direct the orientation of signal-anchor proteins: the topogenic role of the hydrophobic signal domain. J Cell Biol 137:555-62).

At the translocon entrance, the signal peptide is guided in relation to the membrane to the start of the translocation of its N- or C-terminal sequence through the membrane. The hydrophilic fraction of the polypeptide is transferred then, by the aqueous channel to the RE lumen, and the signal released laterally in the lipidic membrane. On the other side, other protein segments may stop or restart their transference to the RE or integrate themselves to the RE lipidic bi-layer as transmembrane domains (TM), and may generate proteins with multiple insertions of alpha helices in the lipidic bi-layer (Higy, M., T. Junne, and M. Spiess. 2004. Topogenesis of membrane proteins at the endoplasmic reticulum. Biochemistry 43:12716-22). The TM domains that promote integration to the membrane generally consist of 20 to 25 non polar amino acids, a size sufficient to transpass the membrane lipidic bi-layer.

FIG. 5 is referent to the processing of the *Flavivirus* polyprotein by cellular and viral proteases. In (A), viral polyprotein protelic sites for generation of the structural proteins, and non structural viral envelope components involved in the viral replication process. The stars (★) represent the glycosilation connected to the asparagine of certain vital proteins, the grey arrows highlight the signal peptidase cleavage sites, and the gray triangles represent the sites for the proteolysis of the viral proteolytic complex (NS2B/NS3). The (?) symbol represents the cleavage point between the NS1/NS2A viral proteins, in which acts a still undetermined cellular protease. The prM protein is later processed by the furine protease in the release of the cell viral particle (Stadler, K., Allison, S. L., Schalich, J. and Heinz, F. X. 1997. Proteolytic activation of tick-borne encephalitis virus by furin. J. Virol. 71:8475-8481). In (B), topology of the prM and E structural protein membranes, which are translocated to the cellular RE and are found associated to their membrane by means of two domains of transmembranar helices, that are indicated by cylinders. The signalase cleavage sites and the NS2B/NS3 viral protease are signed according to the nomenclature below the figure.

In *Flavivirus*, the polyprotein viral precursor of the structural and non structural proteins pass through the RE, membrane at various points and are processed thus: on the lumen side of the RE membrane, by the cellular enzymes, signalases, and on the cytoplasmic side, by the NS2B/NS3 proteolytic viral complex, (FIG. 5A). The RE and the viral particle assembly site, which are formed by the transport of the virions to the cell exterior, by means of the exotic or secretory via (Mackenzie, J. M., and E. G. Westaway. 2001. Assembly and maturation of the *flavivirus* Kunjin virus appear to occur in the rough endoplasmic reticulum and along the secretory pathway, respectively. J Virol 75:10787-99).

Cleavage of the polyprotein in the C/prM, prM/E and E/NS1 intergenic sites, done by signalase, generate the prM and E structural proteins, that remain anchored in the luminal face of the RE membrane and form the *flavivirus* viral envelope. The prM and E proteins of the *flavivirus* envelope are type I membrane proteins (Higy, M., T. Junne, and M. Spiess. 2004. Topogenesis of membrane proteins at the endoplasmic reticulum. Biochemistry 43:12716-22; Paetzel, M., A. Karla, N. C. Strynadka, and R. E. Dalbey. 2002. Signal peptidases. Chem Rev 102:4549-80); That is, the translocation of these proteins to the RE lumen is started by the amino extremity of the polypeptide chain, which associates itself to the translocon, undergoing cleavage by signalase. This leads to the removal of the signal peptide and consequent release of the processed N-terminal from the protein to the RE lumen RE (FIG. 5B). The prM and E proteins are anchored by their carboxi-terminal in the cellular and viral membranes. These domains are composed of two hydrophobic stretches separated by a small fragment containing are least one hydrophobic residue. Thus, on the side of the RE lumen, prM and E form a stable heterodimer that will form the viral envelope (Allison, S. L., K. Stadler, C. W. Mandl, C. Kunz, and F. X. Heinz. 1995. Synthesis and secretion of recombinant tick-borne encephalitis virus protein E in soluble and particulate form. J Virol 69:5816-20; Konishi, E., and P. W. Mason. 1993. Proper maturation of the Japanese encephalitis virus envelope glycoprotein requires cosynthesis with the premembrane protein. J Virol 67:1672-5; Lorenz, I. C., S. L. Allison, F. X. Heinz, and A. Helenius. 2002. Folding and dimerization of tick-borne encephalitis virus envelope proteins prM and E in the endoplasmic reticulum. J Virol 76:5480-91). Thus, the prM and E viral envelope proteins have two transmembrane domains (TM1 and 2; FIG. 5, panel B), which promote their association to the lipidic bi-layer, the first, in the direction amino to the carboxi terminal of the polypeptide chain, consists of a sequence of transference stops of the protein to the RE lumen, and the second, from the signal sequence for importation and processing in the RE.

The two TM domains of the E and prM proteins form anti-parallel alpha-helices, without contact between themselves, which cross the RE Lumen membrane to the cytoplasm and Lumen again (FIG. 5, panel B). For their part, the fragment of 4 to 6 amino acids, rich in polar residues that serve as a connection between these two TM domains, appear to be associated to the internal layer of the phospholipid polar groups of the membrane (Allison, S. L., K. Stiasny, K. Stadler, C. W. Mandl, and F. X. Heinz. 1999. Mapping of functional elements in the stem-anchor region of tick-borne encephalitis virus envelope protein E. Virol 73:5605-12; Mukhopadhyay, S., R. J. Kuhn, and M. G. Rossmann. 2005. A structural perspective of the *flavivirus* life cycle. Nat Rev Microbiol 3:13-22; Stiasny, K., S. L. Allison, A. Marchler-Bauer, C. Kunz, and F. X. Heinz. 1996. Structural requirements for low-pH-induced rearrangements in the envelope glycoprotein of tick-borne encephalitis virus. J Virol 70:8142-7; Zhang, W., P. R. Chipman, J. Corver, P. R. Johnson, Y. Zhang, S. Mukhopadhyay, T. S. Baker, J. H. Strauss, M. G. Rossmann, and R. J. Kuhn. 2003. Visualization of membrane protein domains by cryo-electron microscopy of dengue virus. Nat Struct Biol 10:907-12).

The protein of capsid (C) is separated from the prM, precursor protein of the membrane protein or M, by a signal sequence that directs the translation of the prM. Meanwhile, so that cleavage of the peptide signal occurs and formation of the COOH terminal of the C protein C and the prM N-terminal, it is strictly necessary that the NS2B/NS3 proteolytic complex first catalyzes the COOH terminal COOH of the C protein on the cytoplasmatic side of the RE membrane RE (FIG. 5B). This is the only site of the polyprotein region containing the structural proteins that are processed by this enzyme (Amberg, S. M., A. Nestorowicz, D. W. McCourt, and C. M. Rice. 1994. NS2B-3 proteinase-mediated processing in the yellow fever virus structural region: in vitro and in vivo studies. J Virol 68:3794-802; Lobigs, M. 1993. *Flavivirus* premembrane protein cleavage and spike heterodimer secretion require the function of the viral proteinase NS3. Proc Natl Acad Sci USA 90:6218-22; Yamshchikov, V. F., and R. W. Compans. 1993. Regulation of the late events in *flavivirus* protein processing and maturation. Virology 192:38-51). It is only after this cleavage that the cleavage of the signal peptide by the signal peptidase happens, probably due to the conversion of the cleavage signal peptidase site from a cryptic conformation to an accessible one (Lobigs, M. 1993. *Flavivirus* premembrane protein cleavage and spike heterodimer secretion require the function of the viral proteinase NS3. Proc Natl Acad Sci USA 90:6218-22). The cleavage process of the prM protein signal peptide by the signal peptidase is modulated by the initial hydrolysis of the C protein C-terminal by viral protease. Thus, it is only after the cleavage and generation of the mature C protein that the hydrolysis of the signal peptide occurs, and the consequent release of the prM protein N-terminal in the RE lumen. This stage is preserved between the *Flavivirus*, indicating its regulatory nature during the processing of the polyprotein structural region (Amberg, S. M., and C. M. Rice. 1999. Mutagenesis of the NS2B-NS3-mediated cleavage site in the *Flavivirus* capsid protein demonstrates a requirement for coordinated processing. J Virol 73:8083-94; Stocks, C. E., and M. Lobigs. 1998. Signal peptidase cleavage at the *flavivirus* C-prM junction: dependence on the viral NS2B-3 protease for efficient processing requires determinants in C, the signal peptide, and prM. J Virol 72:2141-9). In this sense, it was shown that this coordinated processing is critical for the incorporation of the nucleocapsid during the formation of the viral particles in the RE (Lee, E., C. E. Stocks, S. M. Amberg, C. M. Rice, and M. Lobigs. 2000. Mutagenesis of the signal sequence of yellow fever virus prM protein: enhancement of signalase cleavage In vitro is lethal for virus production. J Virol 74:24-32; Lobigs, M., and E. Lee. 2004. Inefficient signalase cleavage promotes efficient nucleocapsid incorporation into budding *flavivirus* membranes. J Virol 78:178-86; Stocks, C. E., and M. Lobigs. 1998. Signal peptidase cleavage at the *flavivirus* C-prM junction: dependence on the viral NS2B-3 protease for efficient processing requires determinants in C, the signal peptide, and prM. J Virol 72:2141-9). Therefore, for coordination of the cytosolic cleavages, and the RE lumen RE in the C/prM junction, it is indispensable that an efficient incorporation of the nucleocapsid to the membranes containing the viral envelope proteins occurs, because the brewing of the subviral particles, containing only the viral envelope proteins, do not depend on the C protein or the assembly of the nucleocapsid (Allison, S. L., K. Stadler, C. W. Mandl, C. Kunz, and F. X. Heinz. 1995. Synthesis and secretion of recombinant tick-borne encephalitis virus protein E in soluble and particulate form. J Virol 69:5816-20; Lorenz, I. C., S. L. Allison, F. X. Heinz, and A. Helenius. 2002. Folding and dimerization of tick-borne encephalitis virus envelope proteins prM and E in the endoplasmic reticulum. J Virol 76:5480-91).

The C-terminal portion of the prM protein contains two adjacent hydrophobic stretches, interrupted by a charged residue; that act, the first transmembrane stretch, as a stop signal for the prM transference, and the second, as a signal sequence for the translocation of the E protein to the RE (Markoff, L. 1989. In vitro processing of dengue virus structural proteins: cleavage of the pre-membrane protein. J Virol 63:3345-52; Ruiz-Linares, A., A. Cahour, P. Despres, M. Girard, and M. Bouloy. 1989. Processing of yellow fever virus polyprotein: role of cellular proteases in maturation of the structural proteins. J Virol 63:4199-209). Two adjacent transmembrane sequences act in the same manner, through the stoppage of the E protein translocation and the entrance of the RE from the NS1 protein. In a general fashion, the processing by signal peptidases is important for the importation of the prM, E and NS1 proteins to the RE, and for the generation of their extreme N-terminal.

Cocquerel and collaborators (Cocquerel, L., C. Wychowski; F. Minner, F. Penin, and J. Dubuisson. 2000. Charged residues in the transmembrane domains of hepatitis C virus glycoproteins play a major role in the processing, sub-cellular localization, and assembly of these envelope proteins. J Virol 74:3623-33), when they analyzed the C-terminal sequences of the *Flavivirus* viral envelope proteins, could demonstrate that this organization is very similar to that found in the Hepatitis C virus and in other members of the Flaviviridae Family. It can also be determined, that the sequences which connect the two TM domains, within the different groups, have specific standards related to these different virus groups; but the presence of at least one positively charged group (R or K) in this region was general, indicating an important function. The comparison of this fragment between different virus groups of the Flaviviridae family point to a wide variability of the amino acid sequences of the connection segment of the TM domains TM between these different groups, indicating that these should be related to molecular interactions that would occur specifically within these groups (Cocquerel, L., C. Wychowski, F. Minner, F. Penin, and J. Dubuisson. 2000. Charged residues in the transmembrane domains of hepatitis C virus glycoproteins play a major role in the processing, sub-cellular localization, and assembly of these envelope proteins. J Virol 74:3623-33). Notably, the connection segments of the TM segments of the structural proteins in *Flavivirus* are longer than their counterparts in other groups, presenting various polar residues preserved (N, Q, S and/or T). Another characteristic consists of the fact that the second *Flavivirus* TM domain is noticeably larger, with around 19 residues, in relation to the other viral groups of the family, with around 12 to 13 residues. Mutations in the prM and E TM domains affect the formation of the subviral particles or effective viruses, but appear not to affect the heterodimerization capacity of the prM and E proteins, indicating that these domains are sensitive to a change in their amino acid sequence, and the interactions between the alpha helices of the domains have a role in the formation of the viral envelope (Op De Beeck, A., R. Molenkamp, M. Caron, A. Ben Younes, P. Bredenbeek, and J. Dubuisson. 2003. Role of the transmembrane domains of prM and E proteins in the formation of yellow fever virus envelope. J Virol 77:813-20). Recently, it could be established that the chimeric proteins, expressing these *Flavivirus* prM and E protein transmembrane domains, situated themselves mainly in the RE, indicating that these domains contain retention signals in the RE. It is probable that accumulation of these proteins in the RE occurs, leading to the heterodimerization of these and the brewing of the immature viral particles in the RE lumen, as from which will start the secretion via of the virions to the extra-cellular medium.

In relation to the *Flavivirus* E protein, these TM domains make part of other structural elements situated in the last one hundred amino acid residues of the C-terminal of this protein, a region denominated stem-anchor (Allison, S. L., K. Stiasny, K. Stadler, C. W. Mandl, and F. X. Heinz. 1999. Mapping of functional elements in the stem-anchor region of tick-borne encephalitis virus envelope protein E. J Virol 73:5605-12). This region is not part of the three-dimensional structure elucidated for the E protein ectodomain of different *Flaviviruses*, due to its hydrophobic character (Modis, Y., S. Ogata, D. Clements, and S. C. Harrison. 2003. A ligand-binding pocket in the dengue virus envelope glycoprotein. Proc Natl Acad Sci USA 100:6986-91; Rey, F. A., F. X. Heinz, C. Mandl, C. Kunz, and S. C. Harrison. 1995. The envelope glycoprotein from tick-borne encephalitis virus at 2 A resolution. Nature 375:291-8). In the TBE virus E protein, the stem-anchor region covers the residues from 401 to 496 (Allison, S. L., K. Stiasny, K. Stadler, C. W. Mandl, and F. X. Heinz. 1999. Mapping of functional elements in the stem-anchor region of tick-borne encephalitis virus envelope protein E. J Virol 73:5605-12; Stiasny, K., S. L. Allison, A. Marchler-Bauer, C. Kunz, and F. X. Heinz. 1996. Structural requirements for low-pH-induced rearrangements in the envelope glycoprotein of tick-borne encephalitis virus. J Virol 70:8142-7)

The stem region connects the E protein ectodomain with the transmembrane region. This domain is composed of two alpha-helices, denominated H1 and H2, separated by a connection sequence (CS) highly preserved in the *Flavivirus*, see FIG. 7A (Stiasny, K., Allison, S. L., Marchler-Bauer, A., Kunz, C. and F. X. Heinz. 1996. Structural requirements for low-pH-induced rearrangements in the envelope glycoprotein of tick-borne encephalitis virus. J. Virol. 70: 8142-8147; Allison, S. L., Stiasny, K., Stadler, K., Mandl, C. W. and F. X. Heinz. 1999. Mapping of functional elements in the stem-anchor region of tick-borne encephalitis virus envelope protein E. J. Virol. 73, 5605-5612). The first helix, H1, forms an angle with the external layer of membrane lipids and the second, H2 finds itself placed above the side of the external membrane, with the hydrophobic side turned to the hydrophobic side of the membrane (Mukhopadhyay, S., R. J. Kuhn, and M. G. Rossmann. 2005. A structural perspective of the *flavivirus* life cycle. Nat Rev Microbiol 3:13-22; Zhang, W., P. R. Chipman, J. Corver, P. R. Johnson, Y. Zhang, S. Mukhopadhyay, T. S. Baker, J. H. Strauss, M. G. Rossmann, and R. J. Kuhn. 2003. Visualization of membrane protein domains by cryo-electron microscopy of dengue virus. Nat Struct Biol 10:907-12). It is postulated that the stem region makes contact with the side of the E protein closest to the lipidic membrane, neutralizing the electrostatic repulsion between the phospholipid radicals of the external lipidic membrane and the interior surface of the E protein ectodomain (Zhang, Y., W. Zhang, S. Ogata, D. Clements, J. H. Strauss, T. S. Baker, R. J. Kuhn, and M. G. Rossmann. 2004. Conformational changes of the *flavivirus* E glycoprotein. Structure (Camb) 12:1607-18). The H1 region appears to be involved in the formation of E protein homotrimers during the fusion process (Allison, S. L., K. Stiasny, K. Stadler, C. W. Mandl, and F. X. Heinz. 1999. Mapping of functional elements in the stem-anchor region of tick-borne encephalitis virus envelope protein E. J Virol 73:5605-12). In this way, truncated proteins lacking the stem-anchor domains are secreted as dimers, undergo dissociation in acid pH, which causes the fusion process, but does not manage to form trimers. On the other side, proteins truncated immediately after H1 may form trimers in low pH, indicating that this region may be involved in the conversion of monomers to trimers during the fusion process to the endosomic membrane. The second stem element, CS, is highly preserved in *Flavivirus* (Stiasny, K., S. L. Allison, A. Marchler-Bauer, C. Kunz, and F. X. Heinz. 1996. Structural requirements for low-pH-induced rearrangements in the envelope glycoprotein of tick-borne encephalitis virus. J Virol 70:8142-7), indicating a still undefined important function.

The second amphipatic element of the stem—H2, jointly with the first transmembrane domain (TM1), are important for the stability of the prM/E dimer and may be interacting directly with prM.

As was previously discussed, the two TM1 and TM2 transmembrane elements of the E protein C-terminal constitute a membrane double anchor. The TM2 domain appears to be dispensable in the formation of subviral particles (Allison, S. L., K. Stiasny, K. Stadler, C. W. Mandl, and F. X. Heinz. 1999. Mapping of functional elements in the stem-anchor region of tick-borne encephalitis virus envelope protein E. J Virol 73:5605-12), meanwhile it is an important functional component in the formation of viral particles and viral infection, because it functions as a signal peptide for the translocation of the NS1 protein to the RE lumen.

SUMMARY OF THE INVENTION

The object of the current invention is the development of a vaccine virus, in especial a *Flavivirus* vaccine, obtained from a cloned viral cDNA, having phenotypical characteristics of attenuation and immunogenicity, and that is capable of expressing and inducing a response immune to proteins or fragments of heterologous proteins.

The first discovery of the current invention is related to a method for the production of the recombinant virus containing sequences of codifying nucleotides of all or part of the heterologous proteins, characterized by the following steps:
  a) modification of the heterologous sequences in such a manner that they when cloned and expressed in the vector virus, they have in their 5' portion, nucleotides present at the extreme 5' of the NS1 gene of this vector virus or the other viruses or functionally equivalent sequences, and in their 3' portion, the genomic region corresponding to all or part of the stem and anchor domains of the E of this vector virus or other viruses functionally equivalent sequences, and thus do not compromise the structure and the replication of said vector virus;
  b) insertion of the modified heterologous sequences in (a) in the intergenic region at the E protein structural level and of the non structural NS1 of the vector virus;
  c) obtaining the non pathogenic recombinant virus and holder of the immunological properties, containing the heterologous sequences stably integrated in the viral genome according to the insertion in the region described in (b) and, like this, expressing the heterologous antigen in such a way that it induces the appropriate immune response.

The second discovery of the current invention is referent to a DNA construction, which consists essentially of (i) a vector itself; (ii) a genetically stable virus genome, in which will be inserted modified heterologous sequences; and (iii) the said modified heterologous sequences and introduced into an insertion site in the intergenic region at the E protein structural and the NS1 non structural viral level during stage (a) of the method cited above.

The third discovery of this invention is associated to the recombinant virus produced according to the above cited method, which contains sequences of codifying nucleotides of all or part of the modified heterologous proteins according to stage (a) of the current invention's method and inserted in the intergenic region at the E protein structural and the NS1 non structural of the vector virus stably integrated into the viral genome; for not being pathogenic; for having immunological properties and for expressing the heterologous antigen in a manner that it induces an appropriate immune response, directed to the vector virus or virulent forms homologous to it and the exogenous protein expressed by it.

The fourth discovery of the current invention corresponds to the vaccine composition to immunize against the vector virus of virulent forms homologous to it and/or other pathogens, of which the gene of the heterologous protein, expressed by the recombinant virus originated, to which it is constituted, principally, by the said virus obtained according to the above cited method.

BRIEF DESCRIPTION OF DRAWINGS

FIG. 4: Insertion of heterologous sequences in the 3' NTR region of 17D virus.

FIG. 6: Cleavage point of the signal peptidase in the E and NS1 intergenic region of the *flaviviruses*.

FIG. 8: Regions of E and NS1 protein used in the assembly of the cassette of EGFP protein Expression, at FA 17D infectious clone.

FIG. 9: Sequence of amino acids foreseen for heterologous insertion, containing the gene of EGFP cloned in the E/NS1 intergenic region.

FIG. 12: Comparative diagram of the genome region, comprised between prM and NS1 proteins, in virus of 17D vaccinal phenotype and recombining 17D/Esa/5.1$_{glic}$, and the respective genome positions.

FIG. 13: Propagation properties of the recombining 17D/Esa/5.1$_{glic}$ FA virus in comparison to vaccinal 17D/14 and 17DD Vero cells monolayers.

FIG. 15: Degree of protection afforded by immunization of BABL/c mice with the 17D/Esa/5.1$_{glic}$ T3 virus, on the challenge through intracerebral inoculation with 6.000 PFU of the virus of yellow fever vaccinal strain 17DD.

FIG. 17: Genetic stability of 17D/Esa/5.1 glic virus after ten serial passages in Vero cell monolayers. Analysis of two independent series of serial passages, using RT-PCR and FACS methods.

FIG. 22: Genetic stability of 17D/Den4/FA/Esa/EGFP/6 virus after serial seeding in Vero cell monolayers (20 passages in total).

FIG. 23: Physical map of recombinant T3 $Esa_{trun}$ EGFP plasmid.

DETAILED DESCRIPTION OF THE INVENTION

Figure 1:
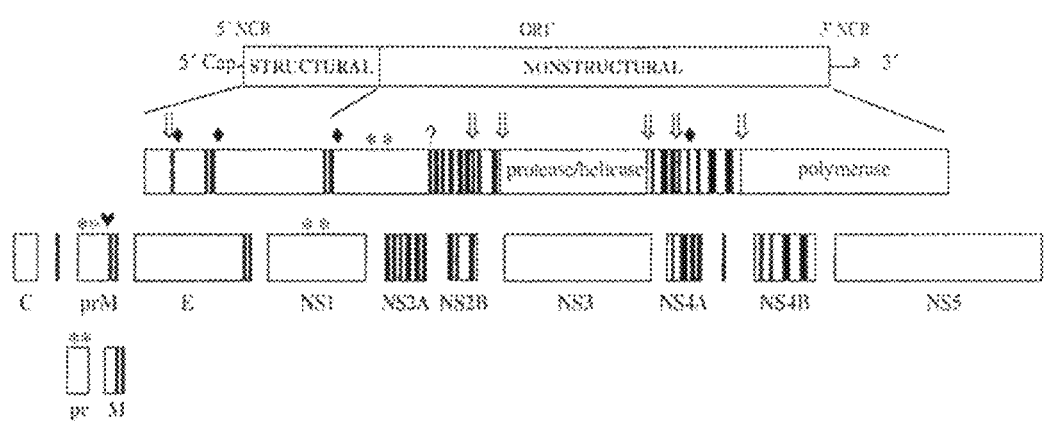
FIG. 1: Genome organization of *Flaviviruses*.
Figure 2:
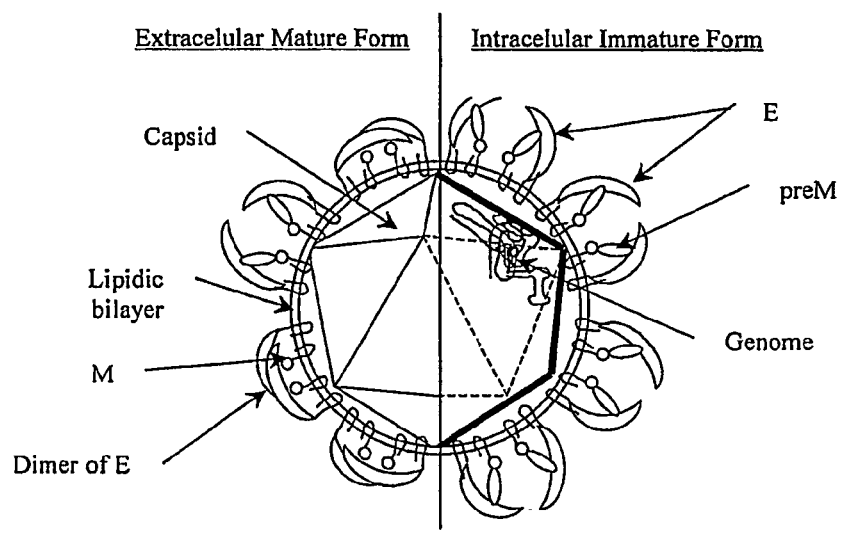
FIG. 2: Scheme of structural organization of *Flaviviruses*, representing the viral particle under its immature intracell and mature extracell forms.
Figure 3:
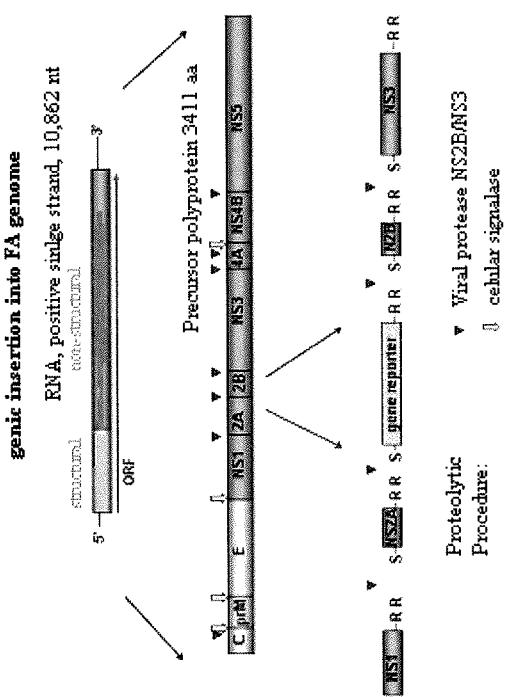
FIG. 3: Strategy for inserting a reporter gene into FA 17D virus genome in the intergenic regions processed by NS2B/NS3 viral protease.
Figure 5:
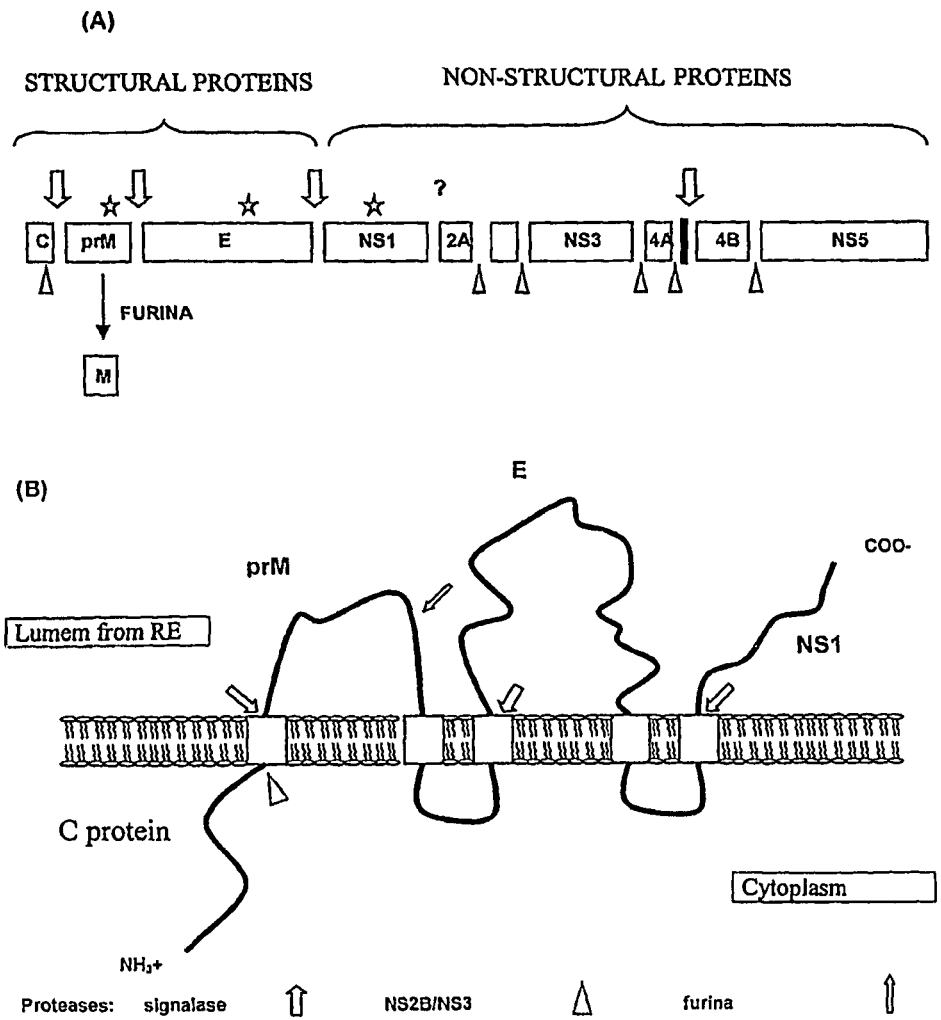
FIG. 5: Processing of polyprotein of *flaviviruses* by cell and virus proteases.

Initially, important definitions are presented for the perfect understanding of the scope of this invention, namely:

Vector virus: virus obtainable from a cDNA template, the genomic sequence of which was modified so as to allow cloning and expression of nucleotide sequences which codify proteins or parts of heterologous proteins originating from other pathogens, specifically in the intergenic region at structural E protein level and non structural NS1. This virus can be, but is not limited to, a *Flavivirus*, especially the 17D strain amarilic virus or its offshoot. Additionally, it may be a wild virus, attenuated or genetically modified.

Recombining virus: a virus that contains, inserted in its genome, specifically in the intergenic region at E structural and NS1 non structural protein level, sequences of codifying nucleotides of the whole or part of heterologous proteins from other pathogens. This virus can be, though not limited to, a *Flavivirus*, especially the 17D strain amarilic virus or its offshoot. Additionally, it can be a wild virus, attenuated or genetically modified. The recombining *flaviviruses* can also be chimerical viruses in which the prM/E genes of a *flavivirus* are replaced by homologous genes of another *flavivirus*. Such viruses are useful in the development of vaccines for human and animal use, granting immune response not only in relation to Yellow fever or other virus occasioned disease, as well as in relation to diseases provoked by said other pathogens. And, in the specific case of such vaccinal application, they should be produced in embryonated hen eggs or in certified cells culture for the production of vaccines for human use (such as Vero cells, MRC-5, primary cultures of chick embryo fibroblast or others in which the recombining viruses will replicate) And, subsequently, may be utilized, in conjunction with at least one pharmaceutically acceptable vehicle, in vaccinal compositions.

Attenuated virus: a virus which ability for causing an accentuated infection and, consequently, produce disease, is lesser when compared with non attenuated, or wild virus.

Wild virus: a virus that can be found, or isolated from living things in their natural environment, existing in the form of laboratorial stock, whose characteristics of pathogenicity are maintained despite being kept in laboratories without intermediary passages in a natural host. This wild virus may also exist in the form of a wild recombining virus after undergoing genetic Manipulation in laboratory.

Offshoot of 17D strain amarilic virus: constitutes of ramifications, or substrains, of the vaccinal strain of the 17D yellow fever virus, that are obtained from this through a differentiated historic of passages in different kinds of cellular substrates permissible to viral replication. Nowadays, the vaccines for human use are derived from two distinct substrains, the 17D-204 and the 17DD.

Virulent forms homologous to the vector virus: constitutes of—as virulent forms homologous to the vector virus—a more pathogenic virus, being homologous to the attenuated one and differing from same in only some positions in the viral genome. For example, in the case of the vaccinal virus of FA (17D), this one differs from the virulent wild virus, of which it derived by serial passages in culture (process through which the genetic mutations accumulated), in only 48 nucleotides in the viral genome of 10862 nucleotides (0.44% of nucleotide difference), representing only about 22 aminoacid alterations along the 3411 aminoacids of the viral polyprotein (about 0.65% of differences from the aminoacid sequence).

Functionally Equivalent Sequences: sequences can be denominated equivalent if they play the same role, without being identical from the aminoacid or nucleotidic sequence viewpoint, over a considered utilization or application. The equivalent sequences may be the result of variability, meaning, any modification, spontaneous or induced, in a sequence, be it substitution and/or deletion and/or insertion of nucleotides, and/or extension and/or shortening of the sequence at one of its ends. A non natural variability may result from genetic engineering techniques.

nucleotidic heterologous (or exogenous) modified sequences: sequences (including, but not limited to those of 10 to 2000 nucleotides) from viruses or other pathogens, which are modified before the insertion in the vector virus. Such modification is carried out so that the same, when cloned and expressed in the vector virus, possess, in its 5' portion, nucleotides present at the 5' end of the NS1 gene of this vector virus or of other functionally equivalent virus or sequences, and in its 3' portion, a genome region corresponding to the whole or a part of the domains of stalk and anchor of the E protein of this vector virus or of other functionally equivalent virus or sequences.

Heterologous expression cartridge: expression genic construction in viral genome or functional equivalents, structured to enable viral sequences fusion to heterologous gene to be expressed in a manner in which its expression effectiveness is improved. In this matter, EGFP gene suffers a fusion of its 5' encoding terminal edge to 27 nucleotides corresponding to NS1 protein N-terminal and of its 3' encoding element to the complete genic sequence, or part of it, of the stem and anchor domains.

This way, this invention relates to the genetic manipulation of viruses, including, though not limited to, *Flavivirus*, preferably the 17D strain vaccinal amarilic virus (the sequence of which is represented by SEQ ID No 15) or its derivatives;

envisaging its utilization as heterologous antigen expression vector and the development of new attenuated live vaccines.

The following method is one of the objects of this invention, namely:

Method for the production of recombining virus containing sequences of codifying nucleotides of whole or part of heterologous proteins, characterized by the following phases:

a) Modification of heterologous nucleotide sequences so as the same, when cloned and expressed in the vector virus, will possess, in their 5' portion, nucleotides present at the 5' end of the NS1 gene of this vector virus or of other functionally equivalent viruses or sequences, and in their 3' portion, a genome region corresponding to the whole or part of the stem and anchor domains of the E protein of this vector virus or of other functionally equivalent viruses or sequences, and so not jeopardizing the structure and the said vector virus replication;

b) Insertion of the heterologous sequences modified in a) in the intergenic region at structural E protein level and of non structural NS1 of the vector virus;

c) Obtention of recombining non pathogenic virus and holder of immunologic properties, containing the heterologous sequences stabilized integrated in the viral genome according to insertion in the region described in (b) and, therefore expressing the heterologous antigen so that the same induces an adequate immune response.

In an embodiment of this invention, the above-mentioned method is characterized by the fact that heterologous nucleotide sequences are modified in (a) so that the same, when cloned and expressed in the virus, will possess, in their 5' portion, the nucleotides described in SEQ ID No. 1 (codifiers of SEQ ID No 5) or their functionally equivalent sequences and, in their 3' portion, the genome region corresponding the domains of stalk and anchor of the viral E protein as described in SEQ ID No. 3 (codifiers of SEQ ID No 7) or their functionally equivalent sequences.

However, for the development of the present method and the consequent obtention of these recombining viruses, especially of *flavivirus*, expressing heterologous antigens, it has been necessary:

(a) the drawing of strategies to allow the introduction of heterologous antigens, without jeopardizing the structure and replication of the vector virus;

(b) to ensure that the construction of cDNA (and its RNA transcripts) generates a non-pathogenic recombining virus and the foreign sequence, beyond that, be stably integrated in the viral genome; and (c) to guarantee that the recombining virus resulting from the abovementioned method, besides being attenuated, will retain its immunologic properties, expressing the heterologous antigen, inserted so as the same will induce an adequate immune response (measured by the formation of antibodies against the viral and recombining proteins), directed both to the vector virus (or virulent forms homologous thereto) and to the heterologous antigen. It is also important the maintenance of the replication capability in cultures of certified cells for the production of vaccines.

In this sense, the presence of specific sequences (nucleotides present at the 5' end of the NS1 gene and a genome region corresponding to the whole or part of the domains of stalk and anchor of the E protein) of this vector virus or of other virus, especially *flavivirus*, associated with protein Exogenous, envisages to minimize or eliminate potential negative effects in the viral replication in function of heterologous insertion in the E/NS1 intergenic region, since:

(1) the 5' end of the NS1 protein is part of the recognition region of the cellular signalase for the generation of the E and NS1 proteins, so as the Exogenous protein undergoes the same kind of processing, not disturbing the obtention of protein, and allowing the heterologous protein to be correctly processed by cellular signalase in the membrane of the endoplasmic reticulum;

(2) The whole or part of the stalk and anchor domains of the E protein, that are added to protein Exogenous, allow normal processing of the NS1 viral protein to occur, given that it possesses the sequence signal for processing by E/NS1 junction signalase.

Therefore, it is prudent to stress that the capability of introducing genetic modifications in the animal viruses has promoted knowledge on the mechanisms involved in the viral propagation, besides allowing these to begin to be used as heterologous proteins expression vectors. DNA viruses—such as SV40, vaccinia, and herpes—are examples of viral vectors for the expression of exogenous insertions.

The advance in the molecular cloning tecniques has led, more recently, to the development of RNA viruses, positive or negative ribbon, such as viral vectors (Palese, P. 1998. RNA vector virus: where are we and where do we need to go? Proc Natl Acad Sci USA. 95:12. 750-12. 752). These are, potentially, more advantageous than the DNA viruses, since they do not have a DNA phase and are not capable of integration in the genome of the host.

One of the most promising positive ribbon Viral RNA vectors is the virus of the *Flavivirus* genus. Among these, is the yellow fever virus, for which there is the sole licensed attenuated virus vaccine against this group of human pathogens.

The yellow fever vaccine is composed by 17D strain vaccinal virus. This vaccine is extremely efficient, promoting about 95% of seroconversion and lasting immunity in the inoculated individuals; detection of neutralizing antibodies being possible, even after periods of over 30 years post inoculation, as can be evidenced in a study made by Poland et al. (Poland, J. D., C. H. Calisher, T. P. Monath, W. G. Downs, and K. Murphy. 1981. Persistence of neutralizing antibody 30-35 years after immunization with 17D yellow fever vaccine. Bull World Health Organ 59:895-900). Additionally, the yellow fever vaccine has other attractive properties that subsidize its development as a recombining vaccinal vector, which would be:

(i) a very well defined production methodology;

(ii) consisting of a cheap single shot vaccine; and (iii) its estimated use is of about 400 million shots administered, with occurrence of few cases of adverse side effects (Monath, T. P. 2001. Yellow fever: an update. Lancet Infect Dis 1:11-20).

Due to these good properties, the FA 17D vaccine platform is being utilized in the development of human recombining vaccines against other pathogens, for which, hitherto, no established vaccines exist, as per the example given by some diseases caused by *flavivirus*, like the Japanese encephalitis (Chambers, T. J., A. Nestorowicz, P. W. Mason, and C. M. Rice. 1999. Yellow fever/Japanese encephalitis chimeric viruses: construction and biological properties. J Virol 73:3095-101; Monath, T. P., F. Guirakhoo, R. Nichols, S. Yoksan, R. Schrader, C. Murphy, P. Blum, S. Woodward, K. McCarthy, D. Mathis, C. Johnson, and P. Bedford. 2003. Chimeric live, attenuated vaccine against Japanese encephalitis (ChimeriVax-JE): phase 2 clinical trials for safety and immunogenicity, effect of vaccine dose and schedule, and memory response to challenge with inactivated Japanese encephalitis antigen. J Infect D is 188:1213-30) and dengue (Guirakhoo, F., K. Pugachev, Z. Zhang, G. Myers, I. Levenbook, K. Draper, J. Lang, S. Ocran, F. Mitchell, M. Parsons, N. Brown, S. Brandler, C. Fournier, B. Barrere, F. Rizvi, A. Travassos, R. Nichols, D. Trent, and T. Monath. 2004. Safety and efficacy of chimeric yellow Fever-dengue virus tetravalent vaccine formulations in nonhuman primates. J Virol 78:4761-75), malaria (Bonaldo, M. C., R. C. Garratt, P. S. Caufour, M. S. Freire, M. M. Rodrigues, R. S, Nussenzweig, and R. Galler. 2002. Surface expression of an immunodominant malaria protein B cell epitope by yellow fever virus. J Mol Biol 315:873-85; Bonaldo, M. C., R. C. Garratt, R. S. Marchevsky, E. S. Coutinho, A. V. Jabor, L. F. Almeida, A. M. Yamamura, A. S. Duarte, P. J. Oliveira, J. O. Lizeu, L. A. Camacho, M. S. Freire, and R. Galler. 2005. Attenuation of recombinant yellow fever 17D viruses expressing foreign protein Epitopes at the surface. J Virol 79:8602-13; Tao, D., G. Barba-Spaeth, U. Ria, V. Nussenzweig, C. M. Rice, and R. S. Nussenzweig. 2005. Yellow fever 17D as a vaccine vector for microbial CTL epitopes: protection in a rodent malaria model. J Exp Med 201:201-9) and, even as could be seen in a study carried out on mice, directed towards melanoma cells (McAllister, A., A. E. Arbetman, S. Mandl, C. Pena-Rossi, and R. Andino. 2000. Recombinant yellow fever viruses are effective therapeutic vaccines for treatment of murine experimental solid tumors and pulmonary metastases. J Virol 74:9197-205).

RNA viruses are considered to have more resistance to the introduction of heterologous genes, when compared to the DNA viruses, which can be observed with the bicistronic vectors of the West Nile fever and the yellow fever virus, which contained interneal ribossomal entry sites (Patent Document WO02089840; Pierson, T. C., M. S. Diamond, A. A. Ahmed, L. E. Valentine, C. W. Davis, M. A. Samuel, S. L. Hanna, B. A. Puffer, and R. W. Doms. 2005. An infectious West Nile virus that expresses a GFP reporter gene. Virology 334:28-40). However, one should consider that these modifications were made in the 3' region not translated in the *flaviviruses* genome; region that, despite showing a certain variability in FA virus size (de Filippis, A. M., R. M. Nogueira, H. G. Schatzmayr, D. S. Tavares, A. V. Jabor, S. C. Diniz, J. C. Oliveira, E. Moreira, M. P. Miagostovich, E. V. Costa, and R. Galler. 2002. Outbreak of jaundice and hemorrhagic fever in the Southeast of Brazil in 2001: detection and molecular characterization of yellow fever virus. J Med Virol 68:620-7; Mutebi, J. P., R. C. Rijnbrand, H. Wang, K. D. Ryman, E. Wang, L. D. Fulop, R. Titball, and A. D. Barrett. 2004. Genetic relationships and evolution of genotypes of yellow fever virus and other members of the yellow fever virus group within the *Flavivirus* genus based on the 3' non-coding region. J Virol 78:9652-65), presents itself highly structured with regions forming much conserved secondary structures (Holden, K. L., and E. Harris. 2004. Enhancement of dengue virus translation: role of the 3' untranslated region and the terminal 3' stem-loop domain. Virology 329:119-33; Thurner, C., C. Witwer, I. L. Hofacker, and P. F. Stadler. 2004. Conserved RNA secondary structures in Flaviviridae genomes. J Gen Virol 85:1113-24). These are involved in the control of translation process (Chiu, W. W., R. M. Kinney, and T. W. Dreher. 2005. Control of translation by the 5'- and 3'-terminal regions of the dengue virus genome. J Virol 79:8303-15) and viral replication (Tilgner, M., T. S. Deas, and P. Y. Shi. 2005. The *flavivirus*-conserved penta-nucleotide in the 3' stem-loop of the West Nile virus genome requires a specific sequence and structure for RNA synthesis, but not for viral translation. Virology 331:375-86; You, S., B. Falgout, L. Markoff, and R. Padmanabhan. 2001. In vitro RNA synthesis from exogenous dengue viral RNA templates requires long range interactions between 5'- and 3'-terminal regions that influence RNA structure. J Biol Chem 276:15581-91; Yu, L., and L. Markoff. 2005. The topology of bulges in the long stem of the *flavivirus* 3' stem-loop is a major determinant of RNA replication competence. J Virol 79:2309-24). The insertion of sequences of the SIER kind, which form secondary structures at the non translated 3' end of the viral genome, could, then, interfere with these key processes to viral variability.

In this invention, a strategy for insertion—of proteins or exogenous proteic domains—between the codifier gene of the E protein and that of NS1 protein was developed.

This insertion site represents, firstly, a vital point in the viral multiplication process. The same consists of the transition of a genic block encoding the viral proteins constituting the viral particle (C, prM and E), and the other codifying the non structural proteins, that are involved in the process of viral replication. The insertion of a heterologous sequence between these blocks could be less harmful to the cascade of molecular events that occurs in this region during replication, since it would be in a intergenic region. And, in these, in principle, there would be no need for special proximity between the two adjacent viral proteins in the recently translated polyprotein; such as for example, would be expected between the structural C, prM and E proteins. The prM and E proteins are sequentially translocated to the ER and interact, forming heterodimers, which, in turn, will take part in the viral particle. Another example would be between NS2B and NS3 proteins, where the insertion of long sequences may result in considerable removal from NS2B, cofactor of NS3, as well as the loss of proteolytic activity and inhibition of the viral polyprotein processing after its synthesis (Bonaldo, M C and Galler, R, unpublished information).

However, in order to be able to insert strange genes in this region, it is necessary to comply with certain restrictions for the viral polyprotein to be correctly processed and the virus be feasible. In the first place, the ectodomain of the E protein is bound to the cell membrane, or to that of the viral envelope, by means of a region called stalk and anchor. This region is conserved between the different members of *flaviviruses*, indicating an important function (Cocquerel, L., C. Wychowski, F. Minner, F. Penin, and J. Dubuisson. 2000. Charged residues in the transmembrane domains of hepatitis C virus glycoproteins play a major role in the processing, subcellular localization, and assembly of these envelope proteins. J Virol 74:3623-33; Stiasny, K., S. L. Allison, A. Marchler-Bauer, C. Kunz, and F. X. Heinz. 1996. Structural requirements for low-pH-induced rearrangements in the envelope glycoprotein of tick-borne encephalitis virus. J Virol 70:8142-7). Such sequence is constituted by 96 aminoacid residues of the C-terminal end of the protein (Allison, S. L., K. Stiasny, K. Stadler, C. W. Mandl, and F. X. Heinz. 1999. Mapping of functional elements in the stem-anchor region of tick-borne encephalitis virus envelope E protein. J Virol 73:5605-12). The stalk domain is composed of two potential alfa-helixes (H1 and H2) connected by a sequence highly conserved in *flavivirus* (CS), the function of which has not been established yet. The H1 segment appears to be involved in the process of conversion of monomers into trimers during the merger of the viral envelope to the endosome membrane. The second amphipathic element of the stalk (H2), along with the first transmembrane domain (TM1), are important for the prM/E dimer stability. The second TM2 stretch works as a signal sequence for the importation of NS1 for the ER. This way, the E protein is anchored inside the ER lumen, through two transmembrane domains, TM1 and TM2, which promote its association to the lipid bilayer. During the process of translocation of the E protein to the ER, TM1 has the function of stopping the transference of E protein to the ER lumen, besides the association to the ER membrane. TM2 consists of a signal sequence, which promotes, in its turn, the translocation of the NS1 to the ER lumen. The role of each of these different stalk and anchor components of the E protein has not been elucidated yet; but, for the correct topology of the E protein in the ER membrane, two sequences equal or functionally similar to the anchor TM1 and TM2 sequences are needed. TM2 works as a signal peptide, which, when processed by the signalase, results in the formation of the protein carboxi-terminal and, besides promoting the translocation of the NS1 protein to the ER.

For these reasons, initially, the attempt for coning and expression of the EGFP autofluorescent protein gene—a variant of the "Green Fluorescent Protein" or GFP of *Aquorea Victoria* (Cormack, B. P., R. H. Valdivia, and S. Falkow. 1996. FACS-optimized mutants of the green fluorescent protein (GFP). Gene 173:33-8)—was traced in function of outflanking this exogenous gene through these sequences. In this way, no considerable disturb is provoked in the cellular addressing and proteolytic processing of E and NS1 proteins. Another important aspect in this wise relates to the existence of the correct sequence to be cleaved, by the peptidase signal, in the junction between the TM2 anchor sequence and the NS1 N-terminal. One may notice, in FIG. 6, that the site—around the peptide bond hydrolysis point, for the generation of the C-terminal ends of the E protein, and of N-terminal end of the NS1 protein—is much preserved between different *flavivirus*. This fact indicates that the same should be important for the recognition and promotion of the proteolysis site specified by the signal peptidase at the E/NS1 junction.

FIG. 6 is associated to the cleavage point of the signal peptidase in the E and NS1 intergenic region of *flaviviruses*. In (A), alignment of the last seven residues of the E protein C-terminal and the nine initial residues of the NS1 protein N-terminal around the cleavage point through the cellular signalase. In (B), consensus motive around hydrolysis point of the peptide bond (↓). The sequences utilized in the alignment are: TBE virus (Genbank NC 001672), yellow fever virus (Genbank U17066), japanese encephalitis virus (JE; NC001437), west nile fever (WN; NC001563), dengue 2 (Den 2; NC001474) and dengue 4 (Den4; M14931). Residues conserved between the species are indicated by grey shading. X means lack of conservation at position. The sequence alignment was carried out through the CLUSTAL W(1.82) program, which consists of a method for progressive alignment of multiple sequences. This analysis was done at http://www.ebi.ac.uk/clustalw/index.html.

So, for the correct processing, both of E protein C-terminal and of NS1 protein N-terminal, it is necessary that the Exogenous protein presents, in its N-terminal, an aminoacid sequence of the NS1 N-terminal and, in its C-terminal, a corresponding E protein C-terminal aminoacid sequence.

Therefore, this invention is associated to the methodology of inserting heterologous sequences between the structural and non structural viral genes (including, though not limited to, *Flavivirus*, preferably the 17D vaccinal strain amarilic virus or its offshoot), through the strategy of translocation and anchoring in several cellular compartments of the heterologous proteins through the genetic merger with the regions called stalk and anchor of any virus or of functionally equivalent sequences.

In a preferential embodiment of this invention the amarilic virus is employed as vector virus. Therefore, once the amarilic virus genome is made of ARN, in this invention, any manipulation thereof is made at complementary ADN (cADN) level cloned in bacterial plasmids. This manipulation is carried out through the infectious clone technology, which consists in the ability of regenerating viruses from cloned complementary ADN.

This invention is thoroughly described through the examples shown below. It is necessary to stress that the invention is not limited to these examples, but also includes variations and modifications within the limits in which it works.

EXAMPLE 1

Drawing of the EGFP Protein Expression Cassette in the Intergenic Region

The EGFP gene and aminoacids sequence is presented, respectively, in SEQ ID No. 2. and in SEQ ID No. 6.

Figure 7:
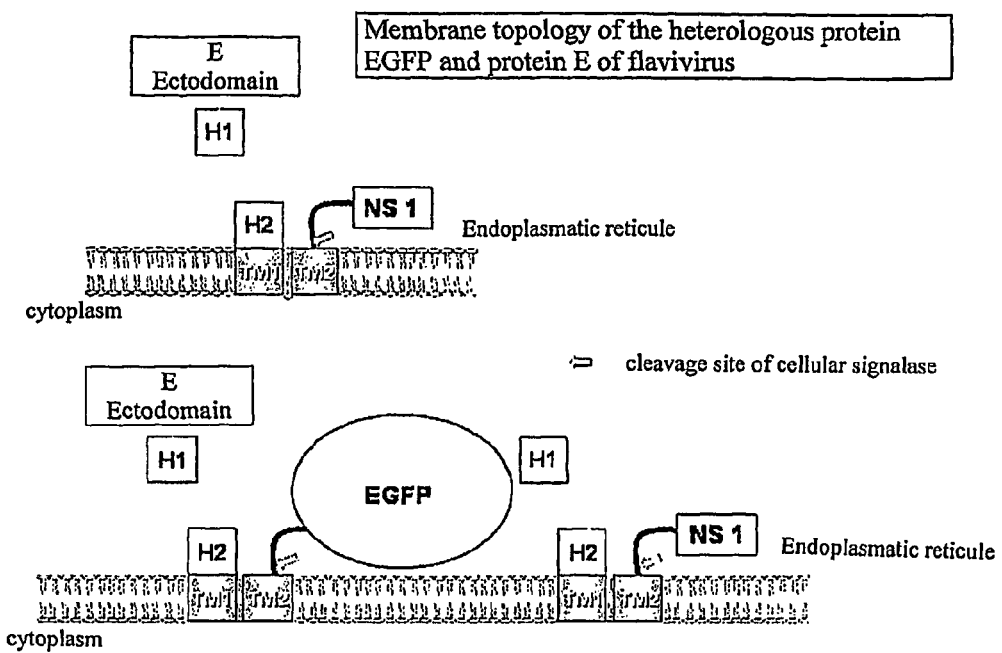
FIG. 7: Comparison of E and EGFP protein topology cloned and expressed in the intergenic region between E and NS1 proteins, in the membrane of ER in a recombining *flavivirus*.

One of the possible theoretic drawings of the cloning and expression of an Exogenous protein in the intergenic region—between the coding genes for the E and NS1 proteins—consists of the genomic insertion of this heterologous sequence, outflanked by genomic *flavivirus* sequences duplicated in this construction; in such a way that this will not disturb the translocation and cellular location of the E and NS1 proteins. In this sense, the strategy used was that of building the insertion so that, at its coding 5' end, the 27 nucleotides corresponding to the NS1 protein N-terminal were merged and, at its 3' end, the gene region corresponding to E protein C-terminal stalk and anchor domains (FIG. 7). Thus, with these duplicated *flavivirus* genome regions outflanking the insert, there are conditions for adequate processing of the E protein anchored in the ER membrane—in that case, with the presence of the TM2 domain (which is a signal sequence) and part of the NS1 amino end, which allows the addressing to the ER and the specific site cleavage through the ER membrane signal peptidase. This results in the formation of E protein C-terminal and the recombining protein aminoterminal release in the ER lumen. Additionally, the merger of stalk domain and anchor to the exogenous protein C-terminal, promotes its anchoring to the ER membrane; besides rendering possible that NS1 protein be translocated to the ER lumen, due to the presence of the inner signal peptide in the TM2 domain.

FIG. 7 is associated to a comparison of E and EGFP protein topology—cloned and expressed, in a recombining *flavivirus*, in the intergenic region between the E and NS1 proteins in ER membrane. In (A), the membrane topology expected for the E protein in a cell infected by a non recombining *flavivirus* is presented. The black arrow indicates o ponto de proteolytic processing, through the signalase, for the formation of the carboxi terminal of this protein and the NS1 protein amino terminal. In (B), the expression in the recombining viruses of the EGFP protein inserted between the E and NS1 proteins. The EGFP protein is fusioned, in its amino-terminal with 9 residues of the NS1 protein amino-terminal—SEQ ID No. 5 (black line), and the cellular signalase cleaves at the indicated point (black arrow). In this manner, there is formation of the E protein C-terminal anchored to the membrane, releasing the amino-terminal of the NS1/EGFP merger in the ER lumen. This very processing would be carried out in the C-terminal region of the stalk domain anchor fusioned to EGFP, which would promote the association of the EGFP to the ER membrane and the liberation of NS1 protein to the ER lumen. The foreseen sequence of this expression cassette contained in the viral polyprotein is presented in the SEQ ID No. 14, as well as, the expected aminoacid sequence of the recombining protein after the phases of proteolytic processing (SEQ ID No. 8).

In the E protein homologous of the yellow fever virus, the establishment of the regions corresponding to stalk and anchor conserved domains, previously elucidated for the E protein of the TBE virus (Allison, S. L., K. Stiasny, K. Stadler, C. W. Mandl, and F. X. Heinz. 1999. Mapping of functional elements in the stem-anchor region of tick-borne encephalitis virus envelope E protein. J Virol 73:5605-12, Stiasny, K., S. L. Allison, A. Marchler-Bauer, C. Kunz, and F. X. Heinz. 1996. Structural requirements for low-pH-induced rearrangements in the envelope glycoprotein of tick-borne encephalitis virus. J Virol 70:8142-7), was effected through the alignment of C-terminal residues of both proteins (FIG. 8A). After this alignment, the regions corresponding to different stalk domain segments (H1, CS and H2) and anchor (TM1 and TM2) were located in the sequence of Yellow fever virus E protein residues. This alignment allowed definition of the aminoacids sequence segments to be added to EGFP protein in accordance with the established strategy. A copy of this entire region for the yellow fever virus, consisting of 288 nucleotides (SEQ ID No. 3) corresponding to 96 E protein final carboxi aminoacids residues (SEQ ID No. 7), was fusioned to the codifying sequence of the EGFP autofluorescent reporter protein in its corresponding C-terminal end, so as to reproduce all motives contained in this sequence, and which are necessary for the correct addressing and processing of the NS1 protein, located later.

A second additional type of aminoacid sequence, derived from the yellow fever virus genome, was associated to the EGFP protein N-terminal. This sequence represents the 9 residues of NS1 protein N-terminal (FIG. 9B), which are also presented by SEQ ID No. 5. Three out of four aminoacids of this peptide amino-terminal are highly conserved among the flavivirus. In all likelihood, they are important for recognition, and bond to the active center and proteolitic cleavage through signal peptidase associated to ER membrane. The use of this sequence, merged to the heterologous protein N-terminal portion, helps promoting the correct cleavage between this and the E protein, so as to form the mature E protein C-terminal and the EGFP protein N-terminal. The utilization of part of NS1 protein N-terminal was already reported, in plasmids of expression of prM and E genes, for the production of subviral particles of TBE in cultures of eucaryote cells, as described by Allison et al. (Allison, S. L., C. W. Mandl, C. Kunz, and F. X. Heinz. 1994. Expression of cloned envelope protein genes from the flavivirus tick-borne encephalitis virus in mammalian cells and random mutagenesis by PCR. Virus Genes 8:187-98). In the work of these researchers, the first 30 codes (120 nt) of the NS1 protein gene were utilized—a sequence considerably greater than that utilized in this construction, with the equivalent to 9 codons of the first yellow fever virus NS1 protein N-terminal aminoacid residues (SEQ ID No. 5).

This way, the clonage of this kind of EGFP expression cassette, or other exogenous protein, in the E/NS1 intergenic region should promote the release of this protein amino terminal in the ER lumen and the anchoring of its carboxi end to the ER membrane, through the stalk and anchor domains or functionally equivalent sequences.

In FIG. 8, regions of E and NS1 protein used in the assembly of the EGFP protein expression cassette in the infectious clone FA 17D are presented. Particularly, FIG. 8(A) is relative to the stalk and anchor domain of the Yellow fever virus E protein; as well as the alignment of the aminoacid sequence of TBE virus E protein stalk and anchor domains (residues of 401 to 496; Genbank NC 001672) and of yellow fever virus (residues of 398 to 493; Genbank U17066). The residues conserved between species are indicated by *, with conservative substitution for or less conservative for. (B) Alignment of the nine residues of NS1 protein amino-terminal end of different flaviviruses. The residues conserved are highlighted in grey in the different viral sequences. The sequences used in the alignment are, in part, the ones described in section (A). The remaining ones are those described for the virus of Japanese encephalitis (JE; NC001437), west of Nile fever (WN; NC001563), dengue 2 (Den 2; NC001474) and dengue 4 (Den4; M14931). The alignment of multiple sequences was made through the method of CLUSTAL W, available at http://www.ebi.ac.uk/cgi-bin/clustalw/.

EXAMPLE 2

Synthesis and Cloning of the EGFP Expression Cassette

For obtention of an EGFP protein expression cassette, two DNA fragments were initially synthesized by PCR:

(1) a DNA fragment of 783 pb containing the EGFP gene, utilizing the pEGFP-C2 plasmid (BD Biosciences Clontech) and the synthetic RG 328 (SEQ ID No. 9) and RG 329 (SEQ ID No. 10) oligonucleotides. The RG 328 (SEQ ID No. 9), of positive polarity, contained seqüencially the gene regions of 15 nucleotides corresponding to the protein carboxi-terminal and, 27 nucleotides corresponding to the first nine aminoacids of the NS1 protein; beyond the 20 nucleotides of the EGFP gene 5' terminal. The RG 329 (SEQ ID No. 10), of negative polarity, contains sequentially the gene regions of 24 nucleotides of the EGFP gene 3' terminal, 15 nucleotides corresponding to the E protein stalk and anchor domains N-terminal;

(2) A second fragment de 339 pb was obtained, utilizing the T3 plasmid and the RG 330 (SEQ ID No. 11) and RG 331 (SEQ ID No. 12) synthetic oligonucleotides, so as to obtain a DNA fragment containing: from sense 5' to 3' of the coding ribbon, the 24 nucleotides corresponding to the EGFP protein carboxi-terminal, followed by gene region of 288 nucleotides (SEQ ID No. 3), corresponding to E protein stalk and anchor domains (genome position FA of 2165 to 2452); followed, finally, by the gene region of 27 nucleotides, corresponding to 9 residues of the amino-terminal of NS1 protein (genome position FA of 2453 to 2479) as described in SEQ ID No. 5.

The merger of these two DNA fragments, for the generation of the EGFP protein expression cassette to be cloned yellow fever virus genome, was carried out by reaction of PCR with equimolar quantities of the de 783 pb and 339 pb fragments, in the presence of 20 μM RG 328 (SEQ ID No. 9) and of RG 331 (SEQ ID No. 12). All those PCR reactions were made with the Platinum Pfx Polymerase enzyme (Invitrogen), in accordance with the manufacturer's recommendations. The reaction products were analyzed in agarose gel electrophoresis at 1% and purified, subsequently, by PCR (Qiagen) products purification system. FIG. 9B shows the expected product sequence, that is decurrent from this sequence of viral origin association strategy at the amino-ends and EGFP protein carboxi-terminal.

The fragment resulting from 1071 pb was cloned in the pGEM-T(Promega) plasmid, in accordance with the manufacturer's specifications. Component bacteriae E. coli MC1061 were transformed with 10 ng of the bond and plagued in selective means (LB a 1.5% agar containing 50 μg/mL ampicillin). Preparations of recombining bacterial clones plasmidial DNA were obtained and submitted to digestion with a Nar I enzyme, for confirmation of cloning of the DNA cassette of 1029 pb (SEQ ID No. 4). One of the bacterial clones was chosen, and the plasmidial DNA was purified as described in one of the following sections.

Therefore, FIG. 9B shows an aminoacid sequence, that is predicted for the heterologous insertion, and that contains o EGFP gene cloned in E/NS1 intergenic region. (A) Aminoacid sequence in the intergenic region between the TM2 domain of the E protein and o NS1 protein N-terminal. (B) This same intergenic region containing the insertion of the heterologous expression cassette. The gray arrows indicate the cleavage site through the signal peptidase associated to the ER membrane.

About 10 μg of the pGEM-T plasmid, containing the EGFP protein expression cassette, was digested with 3 U of Nar I (Promega). The sample was concentrated by precipitation with ethanol and resuspended in electrophoresis sample buffer, besides being submitted to electrophoresis in agarose gel at 1%. The DNA strand of 1029 pb (SEQ ID No. 4) was purified from the gel through the DNA purification system from agarose gels (Qiagen). The material was quantified by spectrophotometry at 260 nm and analyzed in agarose gel electrophoresis at 1%.

The DNA fragment of about 1 kb, containing the cohesive Nar I ends, was bound to the vector T3 plasmid. This plasmid is a derivate from the original pYFM5.2, containing the 17D genome central region, and which contains a restriction site of Nar I just at the junction between the coding genes for the E and NS1 protein. The bond was made with the T3 plasmid, previously digested with Nar I, in the presence of a molar excess 20 times of the insertion containing the EGFP gene, and of the T4 DNA ligase enzyme (Invitrogene). The corresponding to 10 ng of the bond was transformed into *E. coli* Sure (Stratagene), which was plagued in selective means LB 1.5% agar containing 50 μg/mL of ampicillin. Mini preparations of plasmidial DNA were made, from the ampicillin resistant bacterial colonies; and the plasmidial DNA preparations, that presented size superior to that of pT3 native control, were submitted to digestion with Nar I for confirmation of the cassette cloning. The verification of the correct sense of insertion was carried out by nucleotidic sequencing. This way, the recombining pT3 Esa EGFP plasmid was obtained, as in FIG. 10.

Figure 10:
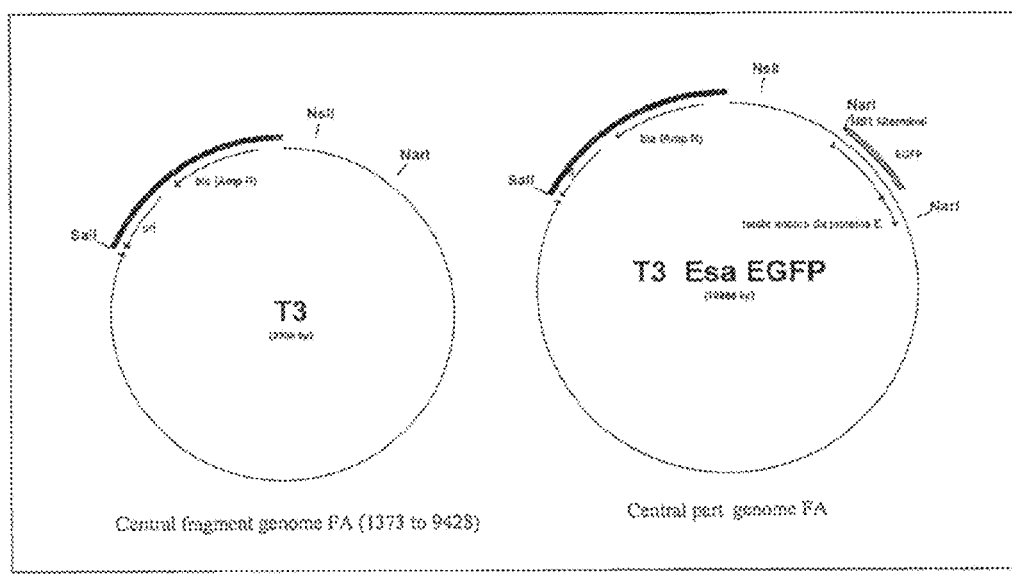
FIG. 10: Map of the T3 Esa EGFP recombining plasmid.

In FIG. 10, the physical map of the T3 Esa EGFP recombining plasmid is presented. The original pT3 plasmid, that contains part of the cloned viral cDNA (from the genome position of 1373 to 9428), was used for cloning EGFP protein expression cassette in the Nar I site of insertion. This recombining plasmid was, afterwards, used for assembling the viral cDNA template.

EXAMPLE 3

Preparation of the cDNA Viral Template

The cDNA template, utilized in the obtention of the FA 17D recombining virus, was obtained by the two-plasmid system (Rice, C. M., A. Grakoui, R. Galler, and T. J. Chambers. 1989. Transcription of infectious yellow fever RNA from full-length cDNA templates produced by in vitro ligation. New Biol 1:285-96; U.S. Pat. No. 6,171,854). In this, the original plasmids, pYF5'3'IV—that contain part of the cloned genome in the form of cDNA (the 5' ends, position of 1 to 2.276, and 3', position of 8.275 to 10.862)—and pYFM5.2—containing the central genomic portion (nt of 1.373 to 9428)—are used for the assembly of complete viral cDNA, by means of a series of cutting enzyme reactions and DNA fragments bond. In the creation of EGFP expression cassette, a derivate of pYF5'3'IV was used, which presents mutations in the 1568 nucleotide, that result in the criation of an EcoRV site in the position of the E protein 200 aminiacid. Such fact leads to change of two aminoacids (E199 D and T200I), as described by Bonaldo et al. (Bonaldo, M. C., R. C. Garratt, P. S. Caufour, M. S. Freire, M. M. Rodrigues, R. S. Nussenzweig, and R. Galler. 2002. Surface expression of an immunodominant malaria protein B cell epitope by yellow fever virus. J Mol Biol 315:873-85), and the presence of the N-glicosilation motive in the protein and, in 1436 and 1437 genome positions. The second plasmid, in which exogenous protein expression cassette was cloned, was a plasmid derived from pYFM5.2, called pT3/Esa/EGFP plasmid. The template of viral cDNA was prepared by cleavage of the plasmids with the Nsi I and Sal I (Promega) restriction enzymes, in compliance with the conditions recommended by the manufacturer. About en μg of each plasmid were digested with both enzymes. The cleavage was monitored by the analysis of percentages equivalent to 200 ng of DNA in agarose gel electrophoresis at 0.8% in buffer TAE. Upon complete cleavage, the enzymes were inactivated by heat. The NSiI/SalI cleavage products of the plasmids were bound with T4 DNA ligase (Epicentre Technologies) in compliance with the conditions set forth by the manufacturer. The linearization of the different cDNA templates was done by use of Xho I restriction endonuclease under the conditions established by the manufacturer (Promega). The resulting products were precipitated with ethanol and resuspended in Tris-EDTA buffer, pH 7.5, free of nucleases. A sample of each preparation was analyzed in agarose gel electrophoresis for detection of the template and its quantification. The preparation's were stored at −20° C. until the phase of transcription in vitro.

Obtention of PA Virus from Viral cDNA: Transcription and Transfection Phases.

From the cDNA templates representing the complete genome, including the sequences of the pE200$_{glic}$ and pT3/Esa/EGFP plasmids, preparations of viral RNA were obtained through the transcription system in vitro of SP6 RNA (AmpliScribe SP6; Epicentre Technologies). The synthesized preparations of RNA in vitro were analyzed in electrophoresis in gel of agarose 0.8% in TAE. Percentages of the RNA preparations were transfected with Lipofectamine (Invitrogen Life Sciences) in Vero cells monolayers, as described by Bonaldo et al. (Bonaldo, M. C., R. C. Garratt, P. S. Caufour, M. S. Freire, M. M. Rodrigues, R. S. Nussenzweig, and R. Galler. 2002. Surface expression of an immunodominant malaria protein B cell epitope by yellow fever virus. J Mol Biol 315:873-85).

Transfection of Viral RNA Synthesized In Vitro

The phase of transfection was carried out in a way similar to that described in patent Document U.S. Pat. No. 6,171,854. The transfection of the Viral RNA synthesized in vitro originated a recombining virus, capable of growth in Vero cells. This new recombining yellow fever virus was called 17D/Esa/5.1$_{glic}$. Its detection was carried out by the appearance of cytopathic effect in the cellular monolayer through phase contrast microscopy. The kinetic follow up of the EGFP protein expression was carried out in the time intervals of 24, 48, 72, 96 and 120 hours in Vero cells monolayers infected with the 17D/Esa/5.1$_{glic}$ with virus a m.o.i of 0.02, and through fluorescence microscopy at 488 nm for detection of the EGFP autofluorescent protein expression.

In order to determine the EGFP expression kinetics, Vero cells were infected with recombining Viruses expressing EGFP at a 0.02 MOI. In the different times, the cellular monolayers were washed twice with PBS, fixed with 4% paraformaldehyde in 0.1M dibasic phosphate buffer for 10 minutes, and washed once with 0.2M dibasic phosphate buffer. Upon fixation, the cells were dyed for 5 minutes with Evans Blue 1%, mounted on blades—with use of Slow Fade containing DAPI (Slow Fade Gold reagent with DAPI—Molecular Probes)—and observed through a Zeiss fluorescence confocal microscope.

Figure 11:
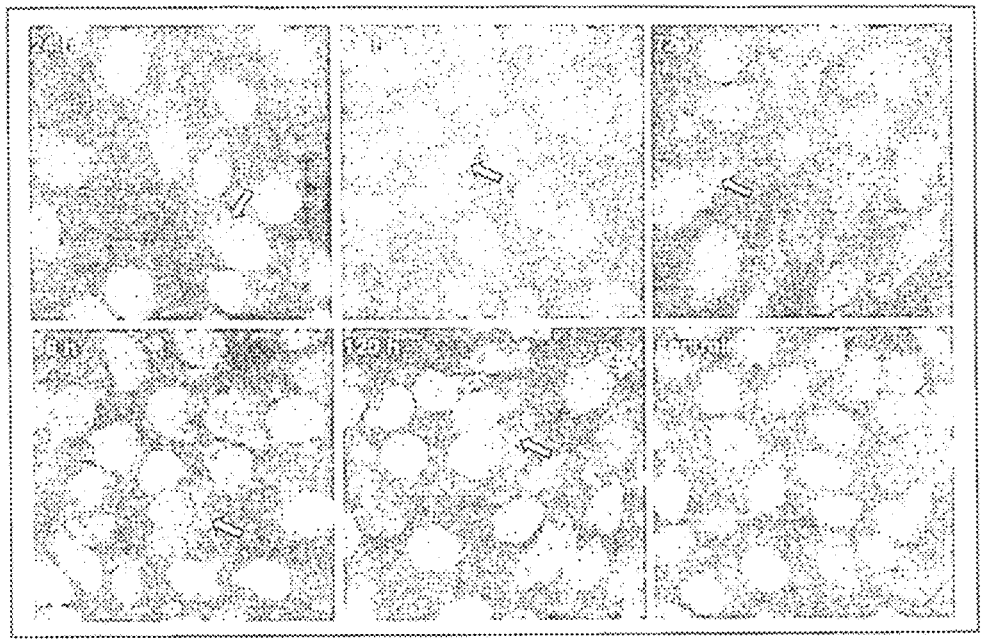
FIG. 11: Analysis of the Vero cells monolayer infection kinetics by the 17D/Esa/5.1$_{glic}$ virus by confocal microscopy.

FIG. 11 shows the kinetics de Vero cells monolayer infection by 17D/Esa/5.1$_{glic}$ virus Preparations of 24 h, 48 h, 72 h, 96 h and 120 h post-infection were analyzed. The green fluorescent marking indicates the presence of EGFP Exogenous protein, this associated in the main to the cellular ER. For comparison, one of the preparations of the control condition was placed, cells not infected, that consist in the time of 96 hours post-infection (FIG. 11).

A viral stock was prepared, by infecting Vero cells monolayers with the pos-transfection supernatant in a m.o.i of 0.1. This stock showed a title of 6.0 log 10 PFU; mL and was used in all phases of viral characterization.

FIG. 12 presents the comparative diagram of the genome regions comprised between the prM and NS1 protein of the 17D vaccinal virus (A), and of the recombining 17D/Esa/$5.1_{glic}$ (B). The genomic sequence of the 17D virus/Esa/$5.1_{glic}$ is shown in SEQ ID No. 13.

EXAMPLE 4

Characteristic of Viral Propagation: Determination of the Viral Growth Kinetics and Phenotype of Lyze Plaque in Vero Cells Monolayers The growth capability of the recombining FA virus obtained was analyzed, in comparison with the FA vaccinal 17DD and 17D/14 viruses, through infection in Vero cells monolayers. Three independent experiments were carried out on viral propagation kinetics in Vero cell monolayers (62.500 cells/$cm^2$), in a number (m.o.i) of infection of 0.02. Percentages of the cellular supernatant of the post-infection times (p.i.) of 24 h, 48 h, 72 h, 96 h, 120 h and 144 h were collected and titled.

In these experiments, two FA 17D viruses of vaccinal phenotype were used as virus controls. The FA17D/14 experimental vaccinal virus was obtained from a cDNA template with a sequence of the 17D/204 sublineage, in which some genetic modifications were introduced based on the 17DD sublineage sequence (U.S. Pat. No. 6,171,854). The FA17D/14 virus has great lyze plaque and growth properties resembling the 17DD vaccinal virus. The second virus is a 17DD strain vaccinal stock, that is the strain utilized in the production of the yellow fever vaccine in Brazil, that also has great plaque phenotype.

It can be verified that both experimental vaccinal viruses—17D/14 and 17DD—present viral growth peaks at 72 hours post-infection, with values of 7.08 and 6.97 log 10 PFU/mL, respectively. On comparing the kinetic profiles of these two viruses with the recombining 17D/Esa/5.1glic virus, it can be noted that this shows a less pronounced growth than the two vaccinal ones, that possess very similar growth profiles in Vero cells monolayers. However, the recombining 17D/Esa/$5.1_{glic}$ virus presents a viral growth peak of 6.63 log 10PFU/mL in 120 hours.

Despite the recombining 17D/Esa/$5.1_{glic}$ virus showing lesser propagation potential in Vero cells monolayers, the titles obtained are still adequate for the vaccinal production scale.

FIG. 13. shows the replication capability of the recombining 17D/Esa/5.1glic FA virus, in comparison with 17D/14 and 17DD vaccinal, in Vero cells monolayers. These cells are being used in the production of vaccines for human use (Montagnon, B. J., J. C. Vincent-Falquet. 1998. Experience with the Vero cell line. Dev Biol Stand. 93:119-223; Handa R., S. Teo, R. Booy. 2004. Influenza: current evidence and informed predictions. Expert Rev Vaccines. 2004 3(4):443-451; Monath, T. P., J. R. Caldwell, W. Mundt, J. Fusco, C. S. Johnson, M. Buller, J. Liu, B. Gardner, G. Downing, P. S. Blum, T. Kemp, R. Nichols, R. Weltzin. 2004. ACAM2000 clonal Vero cell culture vaccinia virus (New York City Board of Health strain)—a second-generation smallpox vaccine for biological defense. Int J Infect Dis. 8 Suppl 2:S31-44).

EXAMPLE 5

Determination of the Lyze Plaque Phenotype

The morphologic determination of the viruses lyze plaque was made by plaqueing in Vero cells monolayers, grown at 62.500 cells/$cm^2$ in 6 well plaques with a coverage of 3 mL of 0.5% agarose of low melting point (Promega) in 199 mean supplemented with 5% bovine fetal serum. In this experiment, two FA 17D viruses of vaccinal phenotype were used as virus controls. The FA17D/E200 virus was created and recovered from an infectious clone containing mutations in the 1568 nucleotide, creating a EcoRV site in the 200 aminiacid protein position and, that leads to the change of two aminoacids (E199 D and T200I), which presents an intermediate plaque phenotype, as described by Bonaldo et al. (Bonaldo, M. C., R. C. Garratt, P. S. Caufour, M. S. Freire, M. M. Rodrigues, R. S. Nussenzweig, and R. Galler. 2002. Surface expression of an immunodominant malaria protein B cell epitope by yellow fever virus. J Mol Biol 315:873-885). It was also utilized as large lyze plaque control, the 17D/14 virus, which was described above. For visualizing the lyze plaques a solution of 10% formaldehyde was added for fixation and a subsequent dying in 0.01% violet crystal. The values assessed were obtained through the two independent experiments, in which about 20 plaques/viruses/experiment were measured. The values determined are shown in Table 1.

TABLE 1

Phenotypic Analysis of the lyze plaque size of the virus in relation to two different experimental vaccinal viruses, 17D/14 and 17D/E200.

| | lysis plaque diameter (mm) | |
|---|---|---|
| virus | average | deviation |
| 17D/14 | 2.80 | 0.67 |
| 17D/E200 | 1.65 | 0.33 |
| 17D/Esa/$5.1_{glic}$ | 0.99 | 0.24 |

EXAMPLE 5

Analysis of the EGFP Exogenous Protein Expression by Flow Cytometry of Vero Cells Infected by the 17D/Esa/$5.1_{glic}$ Virus Along the viral infection, the EGFP autofluorescent protein expression in monolayers of Vero cells was measured by flow cytometry in FACScalibur equipment (Becton Dickison; 15 mW argon laser, 488 nm) with a FL-1 filter, through analysis of 10.000 events by sample. The cells were infected in a moi of 0.02 and were prepared in the post-infection times of 24 h, 48 h, 72 h, 96 h and 120 h post-infection. Vero cells were removed from cellular monolayer by trypsinization, after washing of monolayer with PBS. The cells were resuspended and washed twice in PBS supplemented with 4 mg/ml, BSA, counted and adjusted for the density of $2.0 \times 10^5$ cells/mL in 1% paraformaldehyde for subsequent analysis by cytometry.

Figure 14:
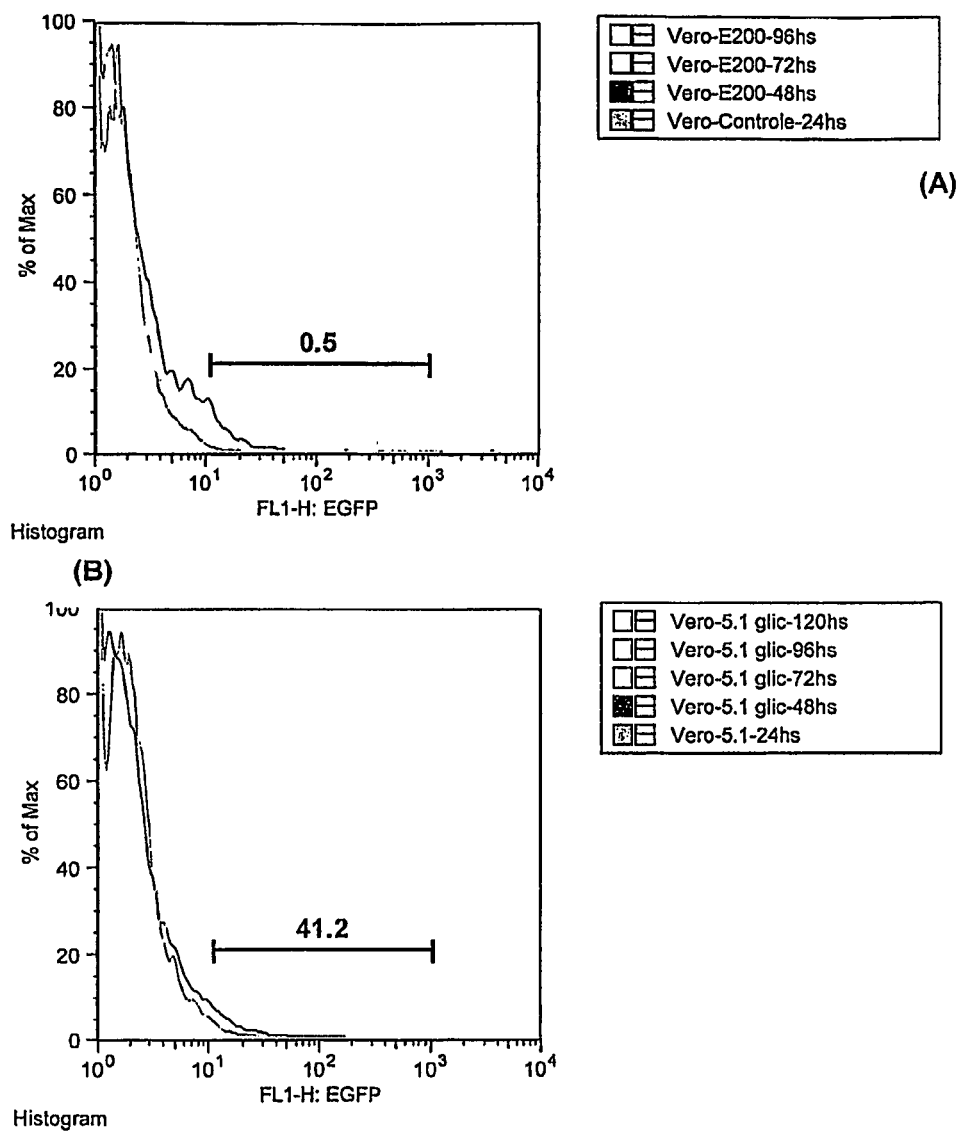
FIG. 14: Analysis of the EGFP fluorescent protein expression kinetics by the 17D/Esa/5.1$_{glic}$ recombining virus in Vero cells and by flow cytometry.

In FIG. 14, it can be observed that the expression of EGFP is specific of the Vero cells infected with 17D/Esa/5.1$_{glic}$ virus, and that its detection is greater in the times of 72 to 120 hours of infection. The bar of 41.2% shows, in FIG. 14B, the percentage of cells expressing EGFP with 120 hours of infection. These results prove that virus is capable of promoting a significant expression of the heterologous protein, even in cellular monolayers infected with a reduced moi, and that the maximal points of the expression are detected from 72 hours of incubation. The use of a reduced moi, together with the high percentage of fluorescent cells, warrant the virus capability for replicating and disseminating to the adjacent cells.

FIG. 14 shows the analysis of the EGFP fluorescent protein expression kinetics through recombining 17D/Esa/5.1glic virus, in Vero cells and by flow cytometry. (A) Vero cells infected by yellow fever virus, 17D/E200T3 control, that do not express the EGFP protein. (B) yellow fever recombining 17D/Esa/5.1$_{glic}$ T3 virus, that expresses the EGFP autofluorescent Exogenous protein cloned in the E/NS1 intergenic region.

EXAMPLE 6

Determination of the Recombining 17D/Esa/5.1$_{glic}$ Virus Attenuation in Mice

As a first step towards proving that the recombining 17D/Esa/5.1$_{glic}$ virus does not overstep the 17D vaccinal virus, in relation to the phenotypic characteristic of neurovirulence, tests were carried out in mice.

In these, groups of 10 Swiss Webster mice (three weeks* old) were inoculated, through intracerebral via, with $3.0 \log_{10}$ PFU of the 17DD vaccinal control and the other viruses. The viral inoculative, estimated in 1.000 PFU for 30 µL, is assessed by titling in Vero cells monolayers for determination of the viral dose, and the animals are followed up for 21 days. The results, contained in Table 2, represent the average of 3 to 5 independent experiments, depending on the viral sample.

TABLE 2

Study of the viral attenuation by neurovirulence test in four week old Swiss Webster mice.

|  | 17DD | 17D/E200$_{glic}$ | 17D/Esa/5.1$_{glic}$ | medium |
|---|---|---|---|---|
| Death rate (%) | 98.0 | 85.0 | 0.0 | 0.0 |
| Average survival time (days) | 11.2 ± 0.55 | 11.8 ± 0.64 | >21 | >21 |
| Average Dose administered (PFU) | 1090 ± 392 | 797 ± 592 | 802 ± 265 | — |

As can be evidenced in Table 2, the 17D yellow fever recombining virus, expressing an EGFP heterologous protein in the E/NS1(17D/Esa/5.1glic) intergenic region, presents itself more attenuated when compared to the 17DD controls and parental 17D/E200$_{glic}$ virus. The 17DD vaccinal virus promoted 98% of mortality in the inoculated animals—with average time of 11.2 days survival—and the parental 17D/E200$_{glic}$ virus, 85.0% over an average survival time of 11.8 days, the intracerebral inoculation with the recombining 17D/Esa/5.1glic virus does not result in death in the 21 days of observation.

These results indicate that the alterations prompted by cloning and expression of EGFP modified protein, of about 400 aminoacid residues, provoke an increase I the degree of viral attenuation.

EXAMPLE 7

Study of the Recombining 17D/Esa/5.1$_{glic}$ Virus Immunogenicity

The immunogenicity of the 17D/Esa/5.1$_{glic}$ virus was assessed in mice. A group of four week old BABL/c mice were immunized with about 2 doses of 50.000 PFU, administered by sub-cutaneous via, in the plantar pad at 15 day intervals. Thirty days after the last dose, blood samples from the mice were obtained by intra-orbital bleeding. The humoral immune response of neutralizing antibodies, directed to the 17D yellow fever virus, was assessed by the test essay of viral neutralization by plaqueing reduction in Vero cells monolayers (PRNT in English, "Plaque Reduction Neutralization Test"). The titles of neutralizing antibodies are given in function of greater seric dilution capable of inhibiting 50% of the lyze plaques number.

As can be verified at Table 3, the FA 17D recombining viruses were able to induce response for specific neutralizing antibodies at indexes comparable to the 17DD vaccinal virus. The seroconversion for the FA virus took place in 100% of the animals that were inoculated with the recombining 17D/Esa/5.1$_{glic}$ T3 virus. And, this immunization regime resulted in title of neutralizing antibodies, directed to the yellow fever virus, from 1:65 to >1:520, which are in a range comparable to that determined for the 17DD vaccinal control virus, of 1:85->1:1.260.

TABLE 3

Immunogenicity of 17D/E200$_{glic}$T3 virus in BALB/c mice.

| condition | Number of animals | % sero-conversion | Answer range (PRNT)* | PRNT* average | average dose (PFU) |
|---|---|---|---|---|---|
| control | 5 | 0 | <1:20 | <1:20 | — |
| 17DD | 10 | 90 | 1:85->1:1.260 | >1:250 | 65.375 |
| 17D/E200 glic T3 | 10 | 100 | 1:100-1:325 | 1:200 | 70917 |
| 17D/Esa/ 5.1 Glic | 15 | 100 | 1:65->1:520 | 1:200 | 18.250 |

*Reciprocal value of the major dilution of the immunized animal serum with each virus that should have resulted in 50% of lyze plaque inhibition.

30 days after the last shot, these animals and another independent experimental set, vaccinated with the same dose regime, were challenged by intracerebral inoculation with an average dose of 6.000 PFU of the 17DD yellow fever vaccinal virus. FIG. 15 shows the mean protection values issued from two immunization and challenge essays. The animals were followed up for 21 days, for notification of deaths and days of occurrence. It can be verified, in the FIG. 15, that the 17D/E200glicT3 parental virus and the recombining 17D/Esa/5 glic promote the protection of 60 and 50%, respectively, of the animals challenged by intracerebral via though 17DD vaccinal virus (with inoculative average of 6.000 PFU), while the vaccinal virus presents a protection rate of about 90%.

FIG. 15 shows the degree of protection afforded by the immunization of BABL/c mice with the 17D/Esa/5.1$_{glic}$T3 virus, in the faced of the challenge for intracerebral inoculation with 6.000 PFU of the 17DD vaccinal strain yellow fever virus. In the upper part of the Figure, the histogram with the death rates in the challenge of animals immunized with vaccinal phenotype virus (17DD and E200$_{glic}$T3), through the virus test (17D/Esa/5.1$_{glic}$T3) and through the negative control (immunization with culture mean) is shown. In the lower part of the Figure, the values obtained by the group relative to the death percentage, the average time of sobrevida, number of animals per group pf analysis and the average dose used in the vaccination regime are shown.

EXAMPLE 9

Genetic Stability of Virus 17D/Esa/5.1glic

The genetic stability of 17D/Esa/5.1glic virus insertion was assessed by two series of ten independent passages through Vero cell monolayers. Thus, when in vitro synthesized viral RNA was obtained, as described in example 3, it was transfected into Vero cell monolayers producing recombinant virus particles. This preparation was named as first cell passage sample or 1P, and it was then used to infect Vero cell monolayers in 175 cm$^2$-T bottles to create a virus sample batch which was employed in most of the performed analysis with 17D/Esa/5.1 glic virus. After cytopathic effect appeared, the viral supernatant, named as second cell monolayer passage or 2P, was measured and store at −70° C. It was assessed a 2P-sample titration, as well as, in order to verify if the insertion was completed in a heterologous manner, it was conducted a viral RNA extraction of this preparation by the LS Trizol-based method (Invitrogen, Life Technologies), and then the RT-PCR procedure, using M-MLV enzyme (Promega Corporation) to allow cDNA synthesis to take place in simple strips and PCR reaction of Tag polymerase enzyme (Promega Corporation), as specified by the manufacturer. In the PCR reaction performed in plasmid DNA samples, Tag polymerase enzyme (Promega Corporation) was also used, according to the manufacturer specifications. RG 174 oligonucleotides (SEQ ID 16) was used, in a positive and corresponding direction to 1639 to 1659 FA genomic region, and RG 19 oligonucleotides (SEQ ID 17), in a negative and corresponding direction to 2619 to 2639 genomic region in order to obtain a DNA fragment with 2030 base pair (bp) intended length, which includes all heterologous region. Thus, PCR products were obtained from T3 and T3 Esa EGFP plasmid DNA, and RT-PCR products from RNA virus preparations were analyzed in 1% agarose gel medium with EDTA-acetate buffer.

Figure 16:
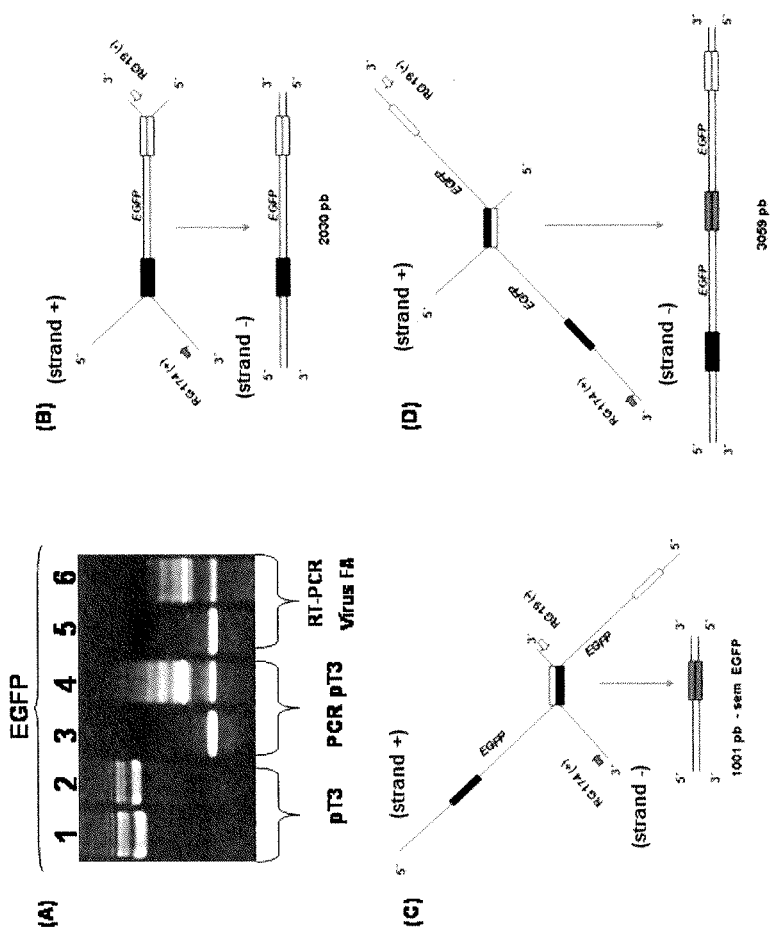
FIG. 16: 0.8% agarose gel electrophoreses analysis of obtained fragments by PCR reactions of T3 and T3 Esa EGFP plasmids and viral RNA preparations of control 17D/E200 and recombinant 17D/Esa/5.1$_{glic}$ viruses. Schematic illustrations of potential experimental synthesis resulting from direct replications of 288 nucleotides that occur in the genome of recombinant 17D/Esa/5.1$_{glic}$ virus.

The yielding of different size products, in PCR experiments conducted in samples of T3 Esa EGFP plasmid and 17D/Esa 5.1 glic virus samples can be explained by the presence of direct replications of 288 nucleotides corresponding to gene regions of stem and anchor domains. This bidirectional synthesis of the PCR reaction is promoted by positive-strip RG 174 oligonucleotides (SEQ ID 16) alignment, which supplements the region with approximately 800 nucleotides before the 5' initial position of heterologous EGFP cartridge expression (NS1 N-terminal, EGFP gene and E-protein stem and anchor domains) and by negative-strip RG 19 (SEQ ID 17) which aligns, in the back encoding region of NS1 protein, 187 nucleotides after the end of such cartridge. It may occurs, after this alignment step during PCR reaction, that the stem and anchor gene region of this heterologous cartridge combines with the homology region, located at the supplementary negative strip, corresponding to the stem and anchor gene region of E protein (FIG. 16C). The yield product would be shorter, with 1001-bp length, as it would not include the insertion cartridge, and therefore, equivalent to the vector virus gene region. On the other hand, an opposite situation could also occur, in which a 288-nucleotide alignment takes place in the encoding region of the stem and anchor domains of E-protein with the negative-strip supplementary homology area of the heterologous cartridge expression. Accordingly, it would be produced a longer PCR fragment, with 3059 bp, including the replicate EGFP gene (FIG. 16D), which, by its turn, is also detected (FIG. 16 A), although to a lesser extent because of its less effective synthesis due to its longer length. Because of the manner in which this alignment occurs and these fragment syntheses, they produce other minor products, as can be evidenced in FIG. 16, bands 4 e 6.

Such initial evidences forced such samples analyses by other supporting method to assess the viral genetic stability, since the sole use of RT-PCR method would be insufficient to its confirmation. Thus, the respective samples to different serial passages were analyzed by flow cytometry approach, which would enable the concurrent viral antigen and EGFP detection. A direct signal relation between them, using as a common denominator the quantity of infected cells, would indicate the presence and functionality of heterologous cartridge expression cartridge. Monolayers with approximately 10 Vero Cells were infected with control and recombinant virus. After 72 hours of viral infection (in a 0.02 medium), these monolayers were twice washed with 1 mL of PBS/1 mM EDTA, and removed by cellular trypsination and submitted to 2.000 g centrifugation for 7 minutes at 4° C. The cells were then resuspended in a 2% paraphormaldehyde solution, and incubated for 20 minutes at 4° C. It was added 0.5 mL of a PBS/1 mg/mL BSA solution, containing 15% saponine, and the cells were centrifuged at 2.000 g for 7 minutes at 4° C. It was then added 1 mL of PBS/BSA/15% saponine solution, and the cells incubated for 10 minutes at 4° C. and centrifuged at 2.000 g for 7 minutes. This cell suspension was treated with 20 µL of anti-yellow fever antibody (yellow fever 17D hyperimmune ascitic fluid—mouse—NIAID, code number V525701-562) diluted in a 1:80 ratio in a PBS/BSA/15% saponine solution for 1 hour at 4° C. It was then added 1 mL of PBS/BSA/15% saponine, and after a 2.000 g centrifugation was performed for 7 minutes and the cells incubated with 20 µL of anti-mouse antibody conjugated with phycoeritrine (DAM; in a 1:40 dilution in a PBS/BSA/15% saponine solution) for 30 minutes at 4° C. After adding 1 mL of a PBS/BSA/15% saponine solution, the cells were centrifuged at 2.000 g for 7 minutes, and the supernatant discarded, and after the cells were submitted to a suspension in 0.3 mL of a 2% paraphormaldehyde solution. In order to obtain data, these cells were centrifuged at 2000 g for 7 minutes and suspended in 0.3 mL of a PBS solution and an analysis was made with the FACScalibur flux cytometer (Becton and Dickinson, USA). The data produced by the cytometer were assessed using the FlowJo Software (TreeStar Inc, USA).

Continuous seeding of this virus in Vero cell monolayers was performed to assess 17D/Esa/5.1 glic virus genetic stability. In Panel A of FIG. 17, it is shown a schematic figure of viral regeneration and subsequent passages (10) of the virus which was obtained after the transfection and in Panel B, the Vero cells percentage which presented fluorescence to vaccine antigen and EGFP after the infection by recombinant 17D/Esa/5.1 glic virus or only by the vector virus. These results consist of two independent series of serial passages; 5P1 and 10P1 samples corresponding to one of the series and 5P2 and 10P2, corresponding to the other independent experiment.

Based on flow cytometry analysis (FIG. 17B), it was calculated a percentage ratio to each sample, that is the relationship among infected cells which show double marking, EGFP's and viral antigens', but only those which had shown viral antigens without any fluorescence signs within EGFP detection range. This figure represents therefore the percentage of infected cells by 17D/Esa/5.1 glic FA virus expressing EGFP protein. It was also performed an electrophoresis analysis in 0.8% agarose gel of the obtained fragments by RT-PCR reaction to identify these samples, using the initial elements (RG174—SEQ ID 16 e RG19—SEQ ID 17) from viral RNA (FIG. 17C). Virus related to passages shown in Panel A, and present in the supernatant of used cultures to obtain cytometry data (Panel B) were used to extract RNA. Band 1, and regenerated E200 vector virus from pT3 plasmid. Band 2-7, RT-PCR products maximized from 17D/Esa/5.1 glic virus RNA in different passage levels. Bands 2 and 3, RT-PCR from RNAs of viral stock solutions obtained from one (1P) or two passages (2P) of the resulting transfection virus, respectively. Bands 4-5 e 6-7 represent RT-PCR products, which were obtained from virus RNA in the fifth and tenth passages of two independent strains (5P1 and 5P2; 10P1 and 10P2, respectively).

Figure 17:
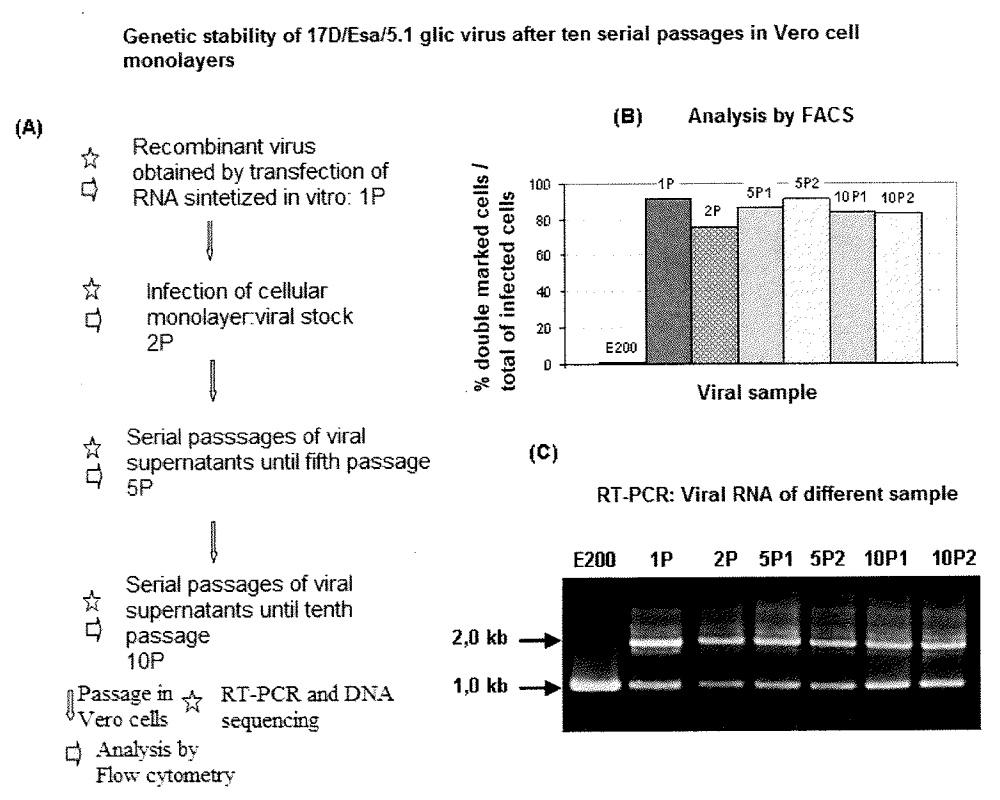

The concurrent analysis of viral samples, by RT-PCR and flow cytometry methods, was performed to serial passages 1P, 2P, of samples of two independent series of serial passages—(5P1 and 10P1; 5P2 and 10P2), as can be seen in FIG. 17.

Figure 18:
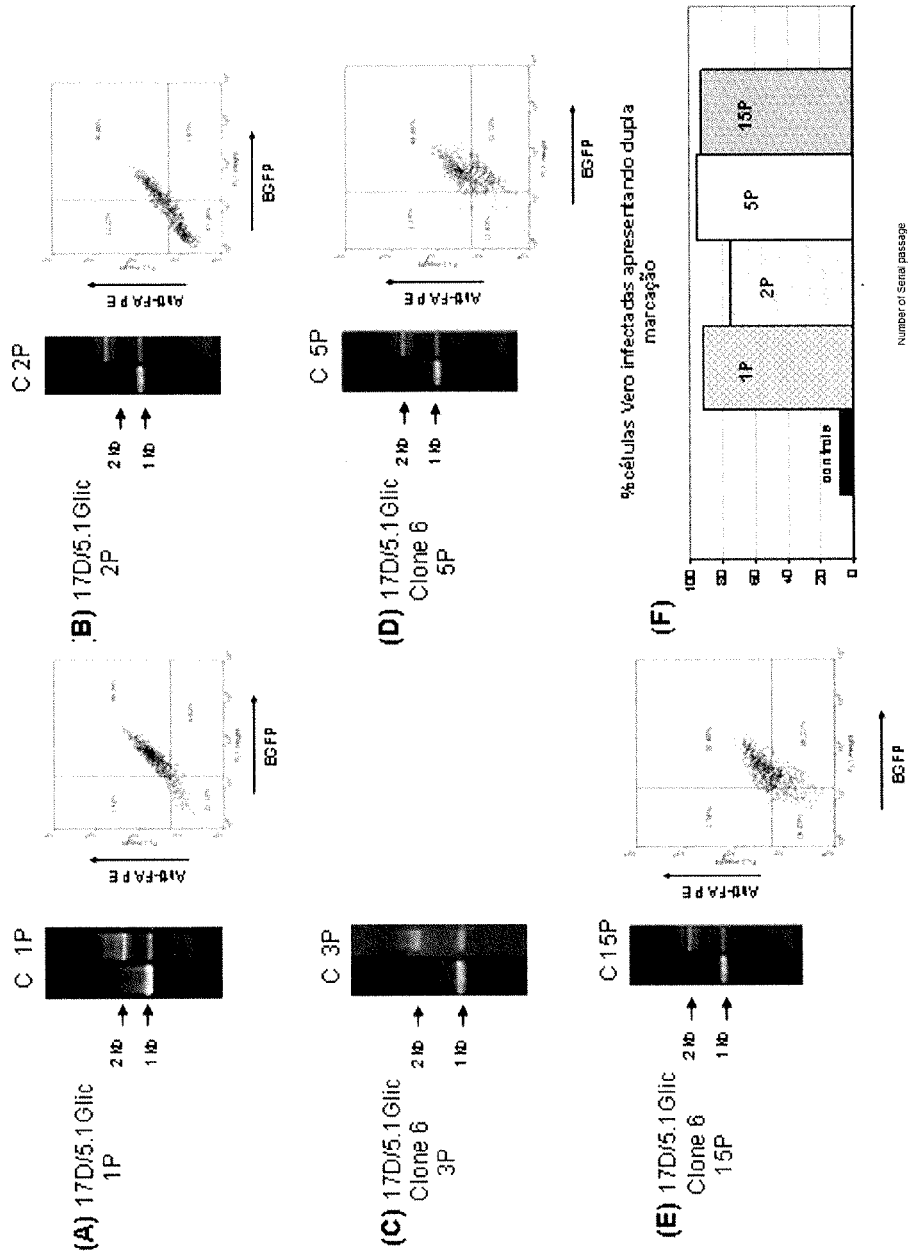
FIG. 18: Genetic stability of viral 6 clone, purified by lyse plaque isolation of 17D/Esa/5.1 glic virus, and submitted to 15 serial passages in Vero cell monolayers. Sample Analysis using RT-PCR e FACS methods.

Flow cytometry analysis revealed that the percentage for positive cells to viral antigens and EGFP, after 17D/Esa/5.1glic virus infection, ranged from 76% to 92% (FIG. 17B, sample 2P and 1P, respectively). This includes the passages, with 85% of doubled marked cells compared to the average value. In baseline, 17D/E200T3 FA control virus shown 0.8% of double marker cells (FIG. 17B). These results suggest that in cells, positive in relation to viral antigen, EGFP is also present. This conclusion is supported by RT-PCR product analysis, using RG 174 (SEQ ID 16) and RG19 (SEQ ID 17) oligonucleotides, due to the presence of 2.0 kb band, indicating that heterologous cartridge expression existed in Vero cell monolayers infected by FA 17D/Esa/5.1 glic virus as far as the tenth consecutive passage (FIG. 17C). 1 kb band, evidenced in all RT-PCR reactions using RNA from 17D/Esa/5.1glic virus detected over the passages, may be related to the device described in FIG. 16. To confirm this interpretation, FIG. 18 shows the same kind of study using a cloned viral population. The transfection supernatant of 17D/Esa/5.1glic 12 virus was placed in Vero cells monolayers plates, with 0.5% agarose coating in 199 Earle's medium enriched by 5% fetal bovine solution (second cellular passage or 2P). After 4-day incubation at 37° C., it was applied to this coating E 199 Earle's medium containing 0.1% neutral red, in order to allow viewing lyse plates and its isolation by puncturing their coating with a Pasteur pipette, to free the material in sterile PBS and the placement in the plates of approximately 100 μL of this suspension in 24-microwell plates containing approximately 100,000 cells per microwell. This coating would mean a third cell passage, but each lyse plate corresponds to a clone of the original population of 17D/Esa/5.1glic virus.

One of these clones was randomly selected to be submitted to genetic stability analysis and it was named clone 6 (FIG. 18). Viral samples of this clone 6 was obtained as far as the fifth tenth continuous passage through Vero cell monolayers and analyzed using RT-PCR and FACS methods (FIG. 18), except the first clone sample 3P, which was only analyzed by RT-PCR, due to the little amount of sample that was obtained (FIG. 18 C). In FIG. 17, Panels A to E, it is shown electrophoresis profiles of RNA amplification by RT-PCR and fluorescence distribution of 17D/Esa/5.1 glic virus, achieved by the transfection in passage 1 (Panel A) and passage 2 (Panel B), and passages 5 and that of clone 6 (Panels D and E, respectively). In Panel C, it is shown the electrophoresis profile of RNA amplification by RT-PCR in clone 6 original stock solution of 17D/Esa/5.1 glic virus, which was used for serial passages shown in Panels D and E, and in Panel F, Vero cell percentage showing fluorescence to vaccine antigens and EGFP after infection by 17D/Esa/5.1 glic virus from passage 1 (1P) or two (2P) of the resulting transfection virus, and clone 6 in passages 5 (5P) and 15 (15P).

In all analyzed samples, it was possible to detect the same band pattern previously established, that is, the occurrence of 2.0 kb and 1.0 kb bands, even in recently cloned viral preparation 3P (FIG. 18C), confirming this RT-PRC technique limitations to assess genetic stability of heterologous insertion in the genome of 17D/Esa/5.1glic virus. On the other hand, flow cytometry analysis of Vero cells, infected by these different viral samples, indicates once again the insertion stability of EGFP gene, since 95% of the infected Vero cells by the viral preparations corresponding to passages 5 and 15 of clone 6, expressed viral antigens and EGFP (FIG. 18E).

EXAMPLE 10

Cartridge Expression of Heterologous Expression for Chimeric *Flavivirus*

Creation and Characterization of Chimeric Virus prM-E 17D/D4.

We constructed the chimeric virus 17D/DEN4/FA using prM/E genes of dengue 4 virus, named Venezuela 88. DEN4 Ven88 virus was isolated from blood sample of a patient who had classical dengue disease, by direct spreading in C6/36 cells. The virus sample, as well as the prM/E gene sequence of this virus, were gracefully provided by Dr. F. Liprandi (IVIC, Venezuela). The viral, chimeric was constructed using 2-plasmid system of FA infectious clone (Rice, C. M., A. Grakoui, R. Galler, and T. J. Chambers. 1989. Transcription of infectious yellow fever RNA from full-length cDNA templates produced by in vitro ligation. New Biol 1:285-96).

The prM/E genes of dengue 4 virus were amplified from extracted RNA of infected cells with partially supplementary synthetic oligonucleotides to edge 5' of prM gene of Den 4 virus (RG 295: 5'-GCTTGATTCCC ACCGGTATGGCGTTTTCCCTCAGCACAAGAGATGGC 3'; SEQ ID No. 18) and to region 5' of gene E (RG 296: 5' GGGCAGAATGCATGGCTCC 3'; SEQ ID No. 19), which code AgeI and NsiI sites, respectively. This fragment was cloned in pG1/2 plasmid (Galler, R. and Freire, M. S. 2003. Vaccines against infections caused by YF virus; infectious cDNA, method for producing a recombinant YF virus from the YF infectious cDNA and plasmids to assemble the infectious cDNA. U.S. Pat. No. 6,589,522) to create pG1/2 DEN4 plasmid. The assembly between gene C from FA and dengue prM was conducted at the cleavage level by signalase (Caufour, P. S., M. C. Motta, A. M. Yamamura, S. Vazquez, Ferreira, II, A. V. Jabor, M. C. Bonaldo, M. S. Freire, and R. Galler. 2001. Construction, characterization and immunogenicity of recombinant yellow fever 17D-dengue type 2 viruses. Virus Res 79:1-14). The remaining part of dengue 4 gene E was cloned after amplifying it with RG 297 oligonucleotides (5' GGAGCCATGCATTCTGCCC 3', including NsiI site; SEQ ID No. 20) and RG 298 (5' GACGCCACA-CAACCCATGTC GGCGCCAACTGTGAAGCCCAGAAACAGAG 3', including Nan site; SEQ ID No. 21) in pYFMT3 plasmid (Galler, R. and Freire, M. S. 2003. Vaccines against infections caused by YF virus; infectious cDNA, method for producing a recombinant YF virus from the YF infectious cDNA and plasmids to assemble the infectious cDNA. U.S. Pat. No. 6,589,522), which contains a Nan site within E and NS1 proteins, producing pT3D4Ven88 plasmid. The cDNA that contains all 17D/DEN4 genome was constructed from the liaison of three pieces: NotI-NsiI derived from pG1/2DEN4 (with SP6 promoter, FA region 5' NTR-C and DEN4 prM-2/3 E), NsiI-MluI, derived from pT3D4Ven88 (encoding region 3' of DEN4 gene E and FA gene NS1), MluI-NotI derived from FA 17D/DEN1 clone (which has the remaining part of the FA genome, cloned in low copy number vector pACNR1180; Mateu, G. P. R. S. Marchevsky, F. Liprandi, M. C. Bonaldo, E. S. F. Coutinho, M. Dieudonne, E. Caride, A. V. Jabor, M. S. Freire, R. Galler. 2006. Construction and biological properties of Yellow Fever 17D/Dengue type 1 recombinant virus. Trans R Soc Trop Med Hyg, no prelo; Bonaldo, M. C., R. C. Garratt, P. S. Caufour, M. S. Freire, M. M. Rodrigues, R. S. Nussenzweig, and R. Galler. 2002. Surface expression of an immunodominant malaria protein B cell epitope by yellow fever virus. J Mol Biol 315:873-85). All plasmids were cultivated in *E. coli* XL-1 Blue.

It was obtained several transformers and 10 completed clones were identified after transforming each strain, suggesting the genetic stability of the construction. Four of them were selected as they had the proper physical map, linearized with XhoI, and used to in vitro transcription. RNA was used to viral regeneration by electroporation of Vero Cells. At first, viral viability evidences were viewed by cytopathic effect. The 4 identified clones generated 17D/DEN4 virus (clones 1, 2, 4 and 5), 5-7 days after electroporation. RNA was extracted from the monolayers, and used to RT-PCR reactions. Limitation analysis and amplicons nucleotide sequencing confirmed the chimeric structure of the virus. It was performed a new passage, from which working stock viral solution were produced (titration around 6.0 $\log_{10}$ PFU/ml). For further working steps, involving molecular cloning of EGFP protein expression cartridge of the chimeric virus Den4/FA genome, it was selected clone number 5, which was named pNSK Den4/FA plasmid.

Molecular Cloning of EGFP Protein Expression Cartridge in Chimeric Virus prM-E 17D/D4 Genome Approximately 10 μg of pGEM-T plasmid, obtained as described in example 2 of this document, containing the expression cartridge of EGFP protein, which was digested with 3 U of Nar I (Promega). This sample concentration was increased by ethanol-precipitation and resuspended in electrophoresis sample buffer, in addition to being submitted to 1% agarose gel electrophoresis. DNA band containing 1029 bp (SEQ ID No. 4) was purified from the gel by DNA purification system of agarose gels (Qiagen). The material was quantitatively assessed by spectrophotometry at 260 nm, and analyzed by 1% agarose gel electrophoresis.

Figure 19:
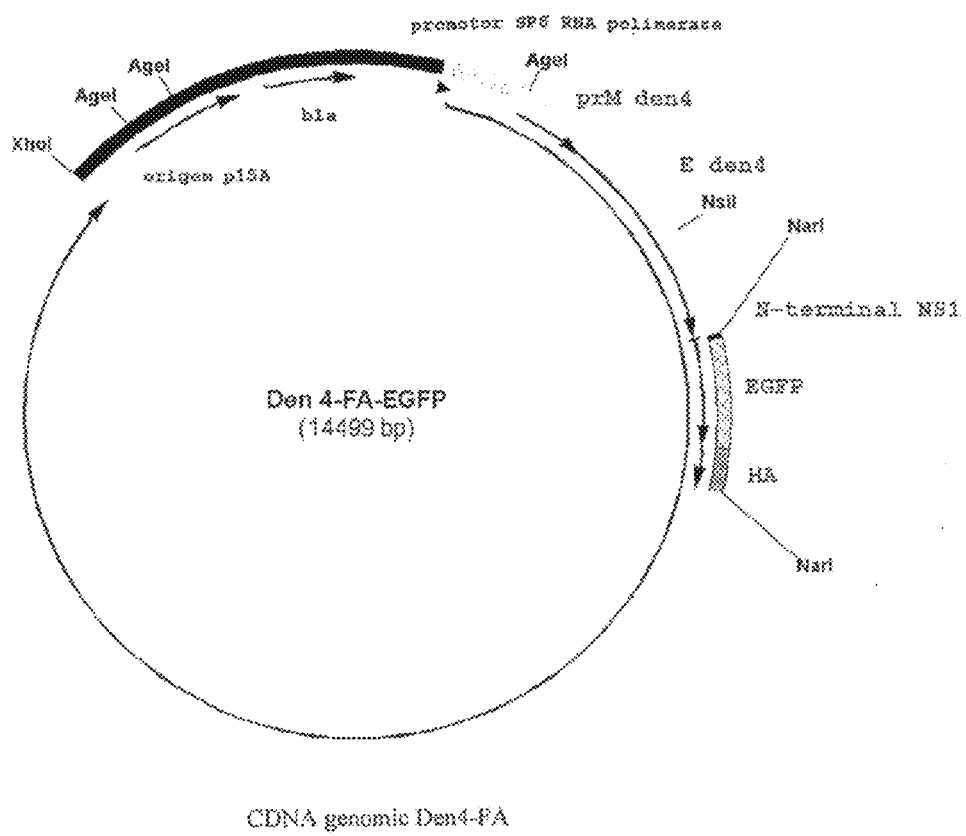
FIG. 19: Physical map of recombinant pNSK Den4/FA/Esa/EGFP plasmid with 14,498 base pairs.
Figure 20:
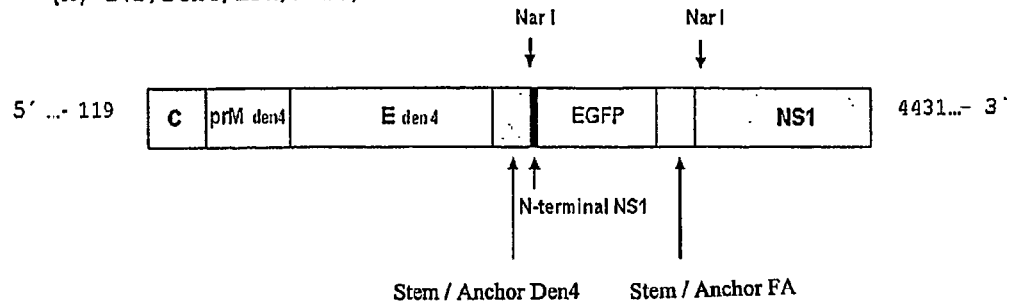
FIG. 20: (A) Position scheme of heterologous expression cartridge between E gene of Den4 virus and NS1 protein gene of FA virus. (B) Position of structural genes, of NS1 gene and of different domains of heterologous expression cartridge in the genome of 17D/Den4/FA/Esa/EGFP/6 virus.

A DNA fragment of approximately 1 kb, including Nar I cohesive edges, was linked to pNSK Den4/FA plasmid, previously linearized with restriction enzyme Nar I. As previously described, this site is situated in this plasmid exactly in the linking point within encoding genes to E protein of dengue 4 viruses and NS1 of yellow fever virus. The liking was made with pNSK Den4/FA plasmid, digested with Nar I, in 20-fold molar excess of insertion containing EGFP gene and the gene of the enzyme T4 DNA liase (Invitrogen). The equivalent amount of 10 ng of liason was transformed into *E. coli* DH5α (Stratagene), which was transferred to plaques with LB 1.5 agar selective medium, containing 25 μg/mL of ampicillin. It was made mini DNA plasmid preparations, from bacteria colonies resistant to ampicillin; and these DNA plasmid preparation were submitted to Nar I digestion to confirm the cartridge cloning. The correct direction of the insertion was verified by the nucleotide sequencing, using synthetic RG 19 oligonucleotide (SEQ ID No. 17). Thus, it was obtained a recombinant pNSK Den4/FA/Esa/EGFP plasmid, with 14.498 base paired-length, as illustrated in the map shown in FIG. 19, and detailed in SEQ ID 22 sequence, in which viral genomic cDNA is included within the 639 and 12,543 nucleotide positions, corresponding to a 11,905 nucleotide viral genome, according to SEQ ID 23. The positions inside the genome of 17D/FA/Den4/Esa/EGFP/6 virus of the sequences of C, prM and E genes and the sequence constituents of the EGFP protein expression cartridge—The 27 encoding nucleotides of NS1 protein N-terminal, the EGFP gene and the 288 nucleotides in the stem anchor part— are shown in FIG. 20B. It should be noted that the heterologous insertion is allowed by Nar I sites used in molecular cloning of *flavivirus* genome, as well as by two stem-anchor regions: the first one located in the 5' part of EGFP gene, is referred to the stem anchor part constituent of the encoding gene for E protein of dengue 4 dengue, and the second one, to the stem anchor part constituent of the encoding gene for E protein of yellow fever virus, part of the heterologous cartridge expression (FIG. 20A).

Obtaining Chimeric Virus 17D/Den4/FA/Esa/EGFP

The pNSK Den4/FA/Esa/EGFP plasmid was digested by the enzyme Xho I, according to the manufacturer specifications (Promega) and the resulting cDNA mould preparation was precipitated with ethanol, and resuspended in Tris-EDTA buffer, pH 7.5, without nucleases. The preparation sample was submitted to agarose gel electrophoresis to detect its mould and quantification. The equivalent amount to 100 ng of linearized mould was used to an in vitro transcription step of the viral RNA, using the enzyme SP6 RNA polymerase (Ampliscribe, Epicentre Technologies), according to protocols previously established (Galler, R. e Freire, M. S. 2003. Vaccines against infections caused by YF virus; infectious cDNA, method for producing a recombinant YF virus from the YF infectious cDNA and plasmids to assemble the infectious cDNA. U.S. Pat. No. 6,589,522). The integrity of the RNA transcripts was verified, using 0.8%/TAE agarose gel electrophoresis. Viral RNA was transfected into Vero cell monolayers, in the presence of Lipofectamine (Invitrogen), which has a concentration of 20 μg/mL in PBS. The culture supernatant was collected after establishing cytopathic effect, and used to obtain viral stock solutions.

Kinetics Assessment of Virus Growth of 17D/Den4/FA/Esa/EGFP Virus Using Vero Cell Monolayers.

Figure 21:
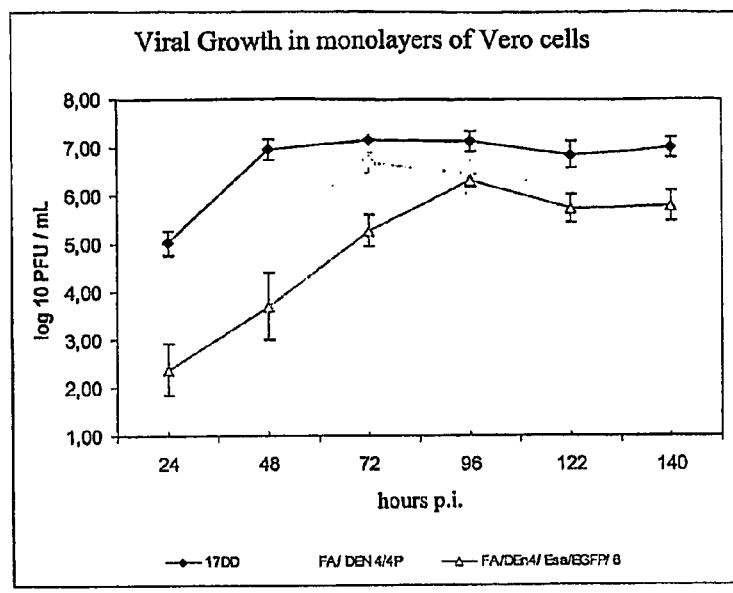
FIG. 21: Kinetics spreading proprieties of chemiric 17D/Den4/FA/Esa/EGFP/6 virus in Vero cell monolayers.

The growth capacity of the obtained recombinant 17D/Den4/FA/Esa/EGFP virus was analyzed, in relation to vaccine FA17DD virus and parent chimeric 17D/Den4/FA virus, by means of infection in Vero cell monolayers. Three independent experiment were performed in respect of the viral spreading kinetics in Vero cell monolayers (62,500 cells/$cm^2$), in an infection multiplicity (m.o.i) of 0.02. Aliquots of cellular supernatant at 24, 48, 72, 96, 120 and 144 hour post-infection (p.i.) were sampled and tittered (FIG. 21).

The viral growth peaks of FA 17DD and 17D/Den4/FA occur 72 hours after infection, at 7.17 and 6.69 log 10 PFU/mL, respectively. When these two viruses kinetics profiles are compared to that of recombinant 17D/Den4/FA/Esa/EGFP virus, it can be concluded that the later has a less marked growth, with viral production of 6.31 log 10 PFU/mL 96 hours after infection (FIG. 21).

Genetic Stability of 17D/Den4/EA/Esa/EGFP Virus by Serial Passages in Vero Cell Monolayers.

The genetic stability of the chimeric 17D/Den4/FA/Esa/EGFP virus insertion was assessed by two series of independent passages in Vero cell monolayers. After in vitro transfection of synthesized viral RNA and the occurrence of cytopathic effect, viral supernatant was collected and the obtained viral particle preparation named first cellular passage or 1P, and it was then used to a further infection of Vero cell monolayers in a 62,500 cells/cm$^2$ density. The second cycle infection of this viral supernatant was named second cellular monolayer passage or 2P, and it was then collect, measured and stored at −70° C., after the occurrence of the cytopathic effect, approximately 96 hours after the infection. Then, it was performed the titration of this suspension in order to proceed to the next serial infection in a 0.02 moi. Afterwards, it was established two series of consecutive viral infection in Vero cell monolayers, named P1 and P2. This procedure was continuously repeated until the twentieth serial passage was reached.

Passage samples 1P, 2P, 5P1, 5P2, 10P1, 10P2, 15P1, 15P2, 20P1 and 20P2 were submitted to viral RNA extraction by Trizol LS method (Invitrogen), and then the RT-PRC procedure, using enzyme M-MLV (Promega Corporation), was performed to achieve the syntheses of simple strip cDNA and Tag polymerase enzyme to allow the PCR reaction (Promega Corporation), according the manufacturer specifications, aiming to verify the heterologous insertion integrity.

It was used RG 367 (SEQ ID 24) oligonucleotides, positive and corresponding direction to 1594-1612 genomic region of dengue 4 virus and RG 19 (SEQ ID 17) oligonucleotides, negative and corresponding direction to 2619 a 2639 genomic region of yellow fever virus. In the genome of 17D/Den4/FA/Esa/EGFP virus, these oligonucleotides correspond to 2276-2294 and 4301-4321 genomic regions, respectively. The intended length of DNA fragment, containing EGFP heterologous cartridge expression cartridge would be 2046 base pairs (bp), while this same region in parent 17D/Den4/FA virus, that is, without EGFP insertion, would have a 1017 bp-length. As can be noticed in FIG. 22, the band which contains the heterologous insertion is kept as far as the twentieth passage of two series of independent spreading, indicating the construction stability expressed by the recombinant *flavivirus*. Minimum quantities of 1,017 by band can be noticed, reflecting the spurious amplification detailed in example 9.

EXAMPLE 11

Heterologous Protein Expression Fusioned to Genomic Region Corresponding to Partial Stem and Anchor Domains of E Protein Heterologous nucleotide sequences can also be cloned and expressed in yellow fever vector virus, in a manner that its 5' portion keeps nucleotides in the 5' portion of its NS1 gene or of others virus and sequences of equivalent function, and in its 3' portion, the genomic region correspondent to stem and anchor domain parts of E protein of this vector virus. Thus, a yellow fever 17D virus was obtained, in which it was cloned the gene that encodes the reporting EGFP protein (SEQ ID 2) among encoding genes to E and NS1 proteins, in such a manner that in its 5' encoding edge, 27 corresponding nucleotides to NS1 protein N-terminal (SEQ ID No. 1) were fusioned, and to its 3' edge, the genic region of 1988 nucleotides (SEQ ID No. 25), corresponding to partial stem domain, only H2 region, followed by anchor region, containing the two transmembrane region, totalizing 66 amino acids (SEQ ID No. 26), having as a result a 939 bp-heterologous gene (SEQ ID No. 29), which corresponds to a protein with 313 amino acids (SEQ ID No. 30). The precursor polyprotein resulting from this recombinant FA virus would be properly cleaved in the regions which side the heterologous protein, because of sign sequences presence expressed in E protein and heterologous protein C-terminal, in an analogous manner as described in example 2.

Synthesis and Cloning of EGFP Expression Cartridge

In order to obtain an expression cartridge for EGFP protein, it was firstly synthesized, using PCR, two DNA fragments:

(1) a 784 bp-DNA fragment, containing EGFP gene, using the pEGFP-C2 plasmid (BD Biosciences Clontech) and the synthetic RG 328 (SEQ ID No. 9) and RG 332 (SEQ ID No. 27) oligonucleotides. The RG 328 (SEQ ID No. 9), of positive polarity, contained, in sequence to 15 nucleotide-genic regions corresponding to E protein carboxyterminal, 27 nucleotides corresponding to the first nine amino acids of NS1 protein; besides 20 nucleotides of EGFP 5' edge. The RG 332 (SEQ ID No. 27), of negative polarity, contains, in sequence to 22 nucleotide-genic regions of EGFP gene 3' edge, 28 nucleotides corresponding to H2 region N-terminal of the stem and anchor domains of E protein.

(2) A second fragment with 247 by was obtained, using T3 plasmid and a synthetic RG 33 oligonucleotides, positive polarity (SEQ ID No. 28) with 50 nucleotides corresponding to a region with 22 encoding nucleotides of EGFP protein C-terminal and 28 nucleotides, corresponding to H2N-terminal region of the stem domain and RG 331 (SEQ ID No. 12), inverted direction, corresponding to 19 nucleotides which encode the carboxy terminal of TM2 followed by 27 nucleotides encoding the NS1 protein N-terminal. The resulting DNA fragment consists of, direction 5' to 3' of the encoding strip, 22 nucleotides, corresponding to the carboxy terminal of EGFP protein, followed by 198 nucleotide genic region (SEQ ID No. 25), which encodes 66 residual amino acids (SEQ ID No. 26), corresponding to truncated stem domains (only H2 region) and E protein anchor domain (2255 to 2452 FA genomic position); finally, followed by the genic region with 27 nucleotides, corresponding to 9 residual amine-terminal of NS1 protein (2453 to 2479 FA genomic position).

The fusion of these two DNA fragments, to generate EGFP protein expression cartridge to be cloned in the genome of the yellow fever virus, was carried out by PCR reaction with equivalent molar amounts of fragments with 784 by and 247 bp, in the presence of 20 µM RG 328 (SEQ ID No. 9) and of RG 331 (SEQ ID No. 12). All PCR reaction was performed with the enzyme Platinum Pfx Polymerase (Invitrogen), pursuant to the manufacturer recommendations. The reaction products were analyzed in 1% agarose gel electrophoresis and later purified by PCR product purifying system (Qiagen).

The resulting fragment with 939 pb was cloned in pGEM-T plasmid (Promega), as specified by the manufacturer. *E. coli* MC1061 competent bacteria were transformed with 10 ng of liaison and placed on selective medium plates (1.5% Agar LB with 50 µg/mL of ampicillin). Plasmid DNA preparations of these bacterial clones were obtained and submitted to digestion by the enzyme Nar I, in order to confirm the cartridge cloning of 939 bp-DNA (SEQ ID No. 29) that encodes a protein with 313 residual amino acids (SEQ ID No. 30). One of these bacterial clones was selected, and its plasmid DNA was sequenced to confirm the direction and integrity of its insertion.

Approximately 10 µg of pGEM-T plasmid, with expression cartridge of EGFP protein, was digested by 3 U of Nar I (Promega). The sample was concentrated with ethanol-precipitation, and resuspended in electrophoresis sample buffer, in addition to being submitted to 1% agarose gel electrophoresis. DNA strip with 939 by (SEQ ID No. 29) was separated from the gel using the DNA purifying system with agarose gels (Qiagen). The material was quantified by spectrophometry at 260 nm, and analyzed by 1% agarose gel electrophoresis.

Figure 23:
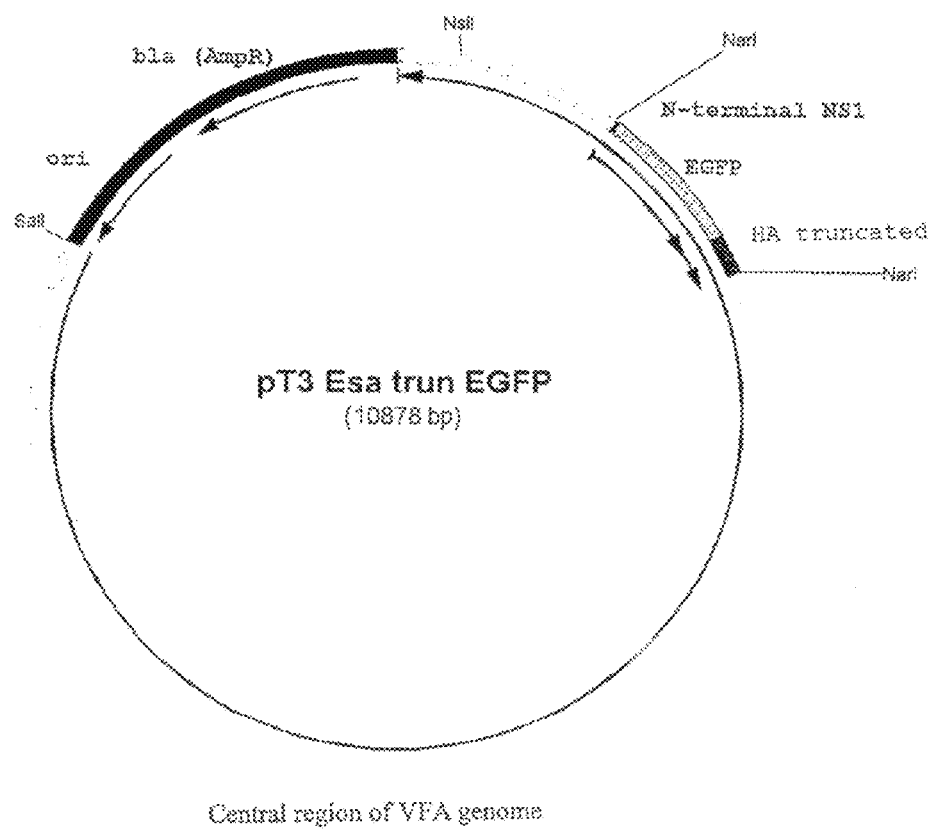

The DNA fragment with approximately 1 kb, containing Nar I cohesive edges I, was linked to T3 vector plasmid, which includes partial cloned viral cDNA (1373 to 9428 genomic position), previously digested by Nar I, in a medium with 20-fold molar in excess of the insertion containing EGFP and enzyme T4 DNA liaise genes (Invitrogen). The corresponding amount to 10 ng of liaison was transformed into $E.\ coli$ Sure (Stratagene), which was placed in plaques in a 1.5% Agar LB selective medium, with 50 µg/mL of ampicillin. It was then prepared mini plasmid DNA preparations from bacteria colonies resistant to ampicillin; and plasmid DNA preparations which had a higher length than the original pT3 control were submitted to Nar I digestion to confirm the cartridge cloning. In order to verify the proper direction of the insertion nucleotide sequencing was performed. Accordingly, recombinant pT3 $Esa_{trun}$ EGFP plasmid was obtained. In FIG. 23, it is shown the physical map of recombinant T3 $Esa_{trun}$ EGFP plasmid.

Mould Preparation of Viral cDNA Viral cDNA mould, used to obtain recombinant FA 17D virus, was achieved using the same methodology as described in example 3 of this document. Accordingly, pT3/$Esa_{trun}$/EGFP and pE200$_{glic}$ plasmids were cleaved with restriction enzymes Nsi I and Sal I (Promega), according to conditions as recommended by the manufacturer. Approximately 10 µg of each plasmid were digested with both enzymes. The cleavage was monitored by analysis of aliquots equivalent to 200 ng of DNA in 0.8% agarose gel electrophoresis in a 0.8% TAE buffer. After complete cleavage, the enzymes were inactivated by heat treatment. The cleavage products NsiI/SalI of these plasmids were linked by T4 DNA liaise (Epicentre Technologies), according to conditions established by the manufacturer. The linearization of cDNA different moulds was made using restriction endonuclease Xho I, under condition as established by the manufacturer (Promega). The resulting products were subjected to ethanol precipitation and resuspended in a Tris-EDTA buffer solution with pH 7.5 without nucleases. A sample of each preparation was analyzed by agarose gel electrophoresis to detect its mould and quantification. The preparations were stored at −20° C. until an in vitro transcription step.

Obtaining FA Virus from Viral cDNA: Transcription and Transfection Steps

Using cDNA moulds, which represent the complete genome, including plasmid sequences pE200$_{glic}$ and pT3/$Esa_{trun}$/EGFP, viral RNA preparations were obtained by in vitro transcription system of RNA SP6 (AmpliScribe SP6; Epicentre Technologies). The in vitro synthetized RNA preparations were analyzed by 0.8% agarose gel electrophoresis in a TAE solution. Aliquots of these RNA preparations wherewith transfected Lipofectamine (Invitrogen Life Sciences) in Vero cell monolayers, as described by Bonaldo and contributors (Bonaldo, M. C., R. C. Garratt, P. S. Caufour, M. S. Freire, M. M. Rodrigues, R. S. Nussenzweig, and R. Galler. 2002. Surface expression of an immunodominant malaria protein B cell epitope by yellow fever virus. J Mol Biol 315:873-85).

RNA Transfection Synthesized In Vitro

The transfection step was performed in a similar manner as described in the U.S. Pat. No. 6,171,854 document. The viral RNA transfection synthesized in vitro originates a recombinant virus, with the capacity to grow in Vero cells. This new recombinant yellow fever virus was named 17D/$Esa_{trun}$/4 trun/4$_{glic}$. Its, detection was achieved when cytopathic effect appeared in the cellular monolayer in phase contrast microscopy. The detection of EGFP protein expression by this virus was performed within a time range of 24, 48, 72, and 120 hours in Vero cells monolayers infected by 17D/$Esa_{trun}$/4$_{glic}$ virus with a 0.1 m.o.i using fluorescence microscopy at 488 nm.

Figure 24:
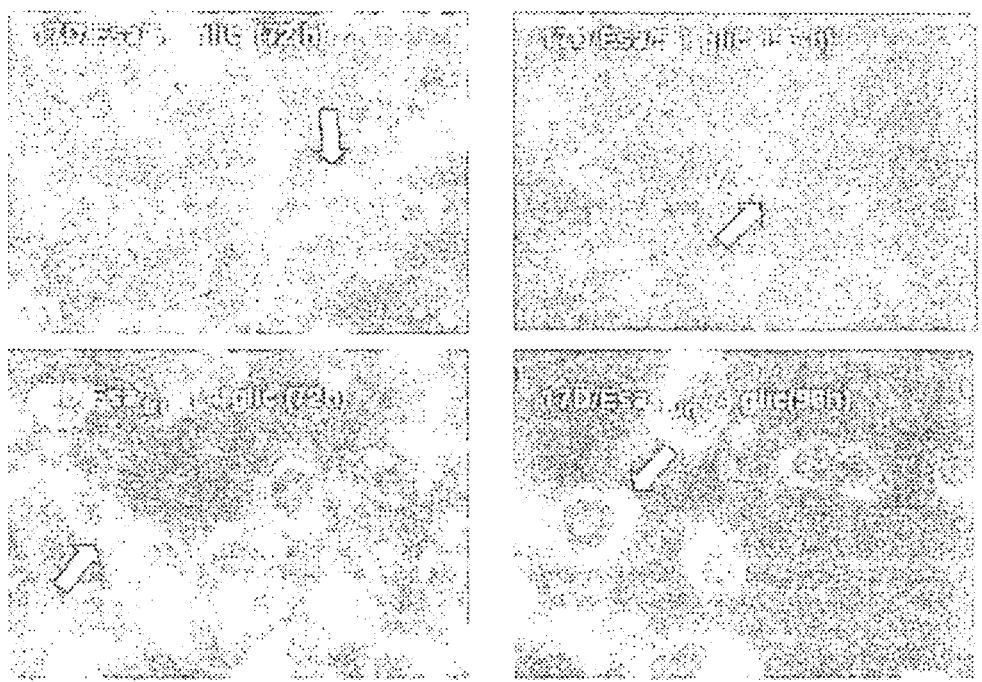
FIG. 24: Analysis by fluorescence optical microscopy of Vero cell monolayers infected by $17D/Esa_{trun}/4_{glic}$ and $17D/Esa/5.1_{glic}$ viruses 72 and 96 hours after infection.

The cellular monolayers were washed twice with PBS, and fixed with 4% paraphormaldehyde solution with 0.1 M dibase phosphate buffer for 10 minutes, and washed once again with 0.2 M dibase phosphate buffer. After fixing them, they were assembled in plates and seen using a Nikon microscope (E600 eclipse model). The highest fluorescence detection of EGFP protein expressed by 17D/$Esa_{trun}$/4$_{glic}$ virus was at 72 and 96 hours after infection, similarly to 17D/Esa/5.1$_{glic}$ virus, which has its stem anchor region completely fusioned to this heterologous protein carboxyterminal (FIG. 24).

Figure 25:
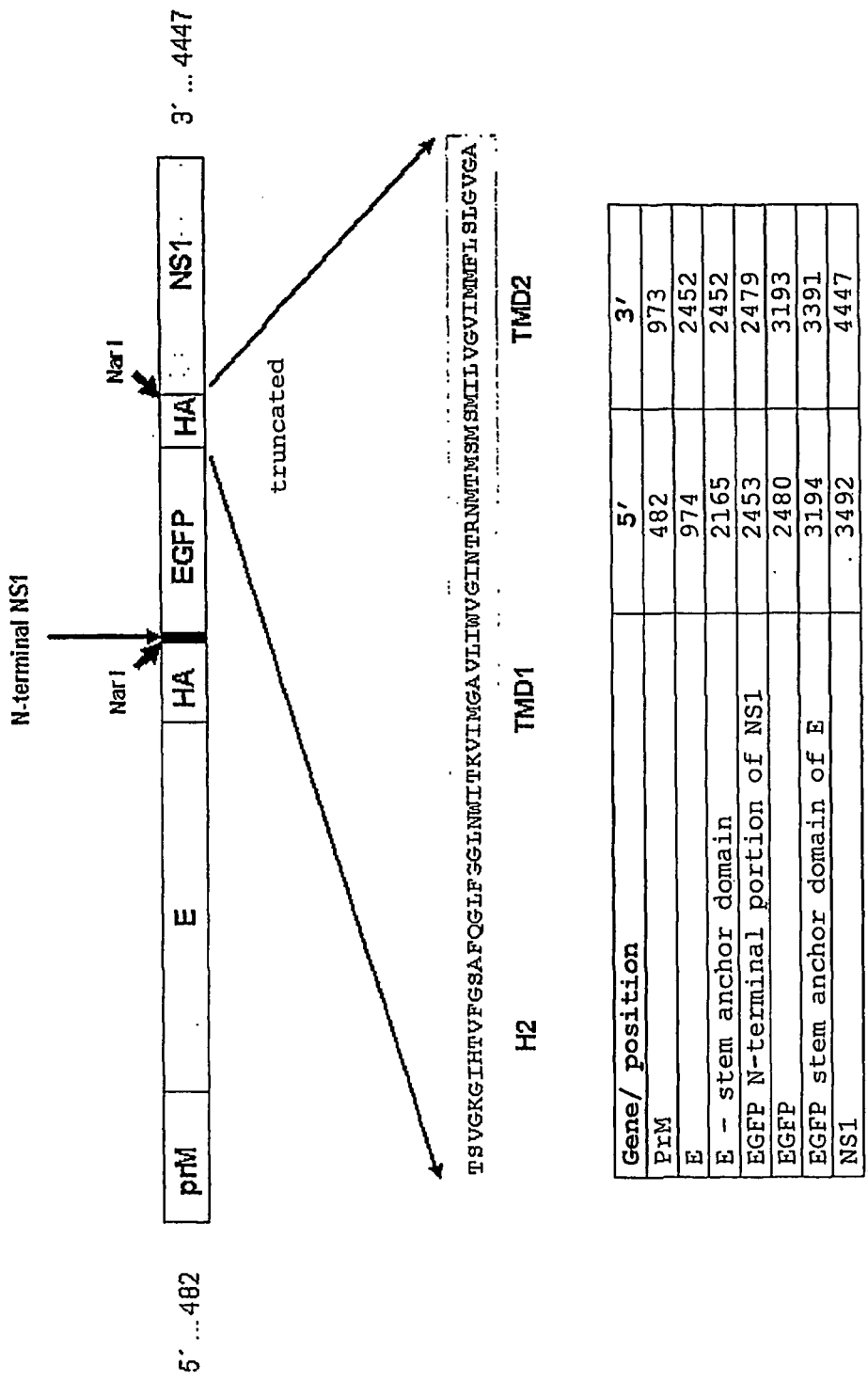
FIG. 25: Regional scheme of viral genome included within prM protein and NS1 encoding genes in recombinant $17D/Esa_{trun}/4_{glic}$ virus, detailing amino acid sequence of truncated stem anchor region associated to heterologous expression cartridge.

FIG. 25 shows, in a schematic manner, the viral genome region, included within prM protein and NS1 protein encoding genes in the recombinant 17D/$Esa_{trun}$/4$_{glic}$ virus, detailing amino acid sequences of the truncated stem anchor region associated to the heterologous expression cartridge, as well as restriction enzyme Nar I sites which side this region, and were used in the molecular cloning of this cartridge in the infectious clone of FA 17D virus. The location of prM, E genes, of heterologous cartridge in the genome of recombinant 17D/$Esa_{trun}$/4$_{glic}$ virus—with their respective domains (27 nucleotides of NS1 gene, EGFP gene and truncated stem and anchor)—and NS1 gene is also shown in FIG. 25.

Characteristics of Viral Spreading: Kinetics Assessment of Viral Growth in Vero Cell Monolayers The capacity to grow of recombinant FA 17D/$Esa_{trun}$/4$_{glic}$ virus was compared to that of recombinant 17D/Esa/5.1$_{glic}$ virus and that of control 17DD viruses—vaccine virus used in human immunization—and experimental vaccine virus 17D/E200T3 infecting Vero cell monolayers (62,500 cells/cm$^2$) in a 0.02 moi. At least three independent experiments were performed for the kinetics of viral spreading under these conditions. Aliquots of cellular supernatant of 24, 48, 72, 96 h, 120 and 144 hour post-infection were collected and tittered.

Figure 26:
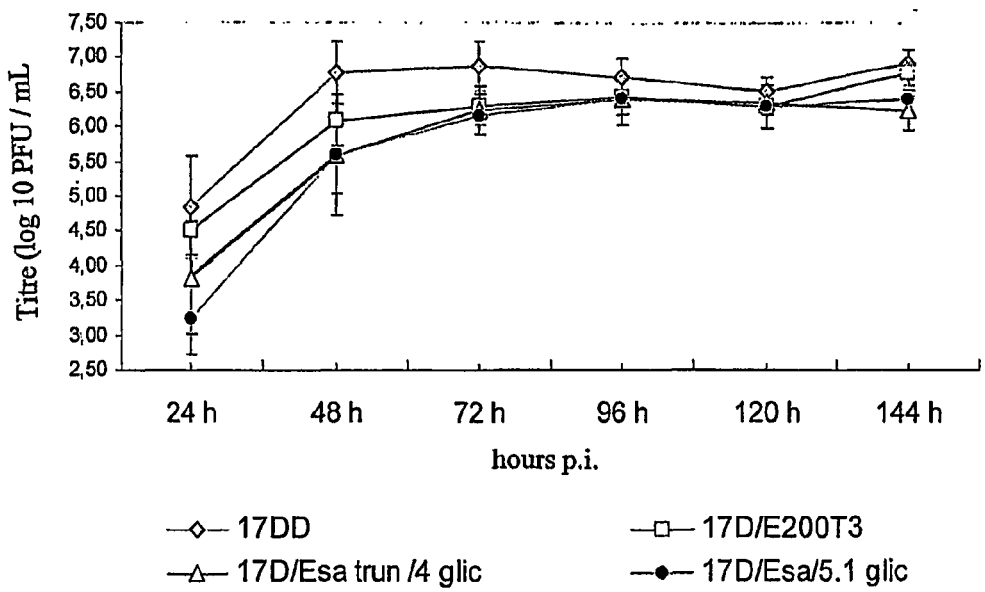
FIG. 26: Kinetics graphics of Vero cell monolayer infections by $17D/Esa_{trun}/4_{glic}$ virus in a 0.02 moi.

FIG. 26 shows graphically the infection kinetics of Vero cell monolayers.

It can be noticed that, while the vaccine FA 17DD virus had a viral growth peak 72 hours post-infection, with 6.88 log 10 PFU/mL, not only the experimental vaccine 17D/E200T3 virus, but the recombinant viruses that express EGFP—17D/$Esa_{trun}$/4glic and 17D/Esa/5.1glic—had very similar kinetics profiles with viral production peaks in 96 hours, with values near to 6.40 log 10 PFU/mL.

A good spreading in Vero cell monolayers of recombinant 17D/$Esa_{trun}$/4$_{glic}$ and 17D/Esa/5.1$_{glic}$ viruses suggests that the production of recombinant vaccine 17D viruses, to make insertions within E and NS1 proteins in a production level, is feasible.

Although illustrated and described here with reference to certain specific embodiments, the present invention is not meant to be limited only to the details shown. Several modifications can be made on the details within the ambit and reach of equivalents without departing from the spirit of the invention.

The invention claimed is:

1. A method for the production of recombinant vector virus, wherein the vector virus comprises nucleotide sequences encoding at least one heterologous protein, or fragments thereof, said method comprising the following steps:
   (a) providing at least one heterologous nucleotide sequence,
   (b) providing a vector virus sequence, wherein said vector virus sequence comprises nucleotide sequences encoding the NS1 protein and the E protein sequence of a *Flavivirus*;
   (c) cloning the heterologous sequence of step (a) into the vector virus sequence, wherein the insertion of the heterologous sequence occurs in the E/NS1 intergenic region, further wherein the nucleotides present at the 5' end of the NS1 gene and the whole or part of the domains of stem and anchor of the E protein are present at either end of the heterologous sequence; wherein when the heterologous protein is expressed it will be processed normally by a host cell and can induce an immune response.

2. The method of claim 1 wherein said vector virus is wild, attenuated, or recombinant.

3. The method of claim 1 or 2 wherein said vector virus is a *Flavivirus*.

4. The method of claim 3 wherein the *Flavivirus* is the Yellow Fever virus corresponding to 17D strain or its derivatives.

5. The method of claim 3 wherein the *Flavivirus* is a chimeric Yellow Fever virus, which has the prM and E genes of dengue 1, 2, 3, and 4 virus or of any other chimeric *Flavivirus* obtained by the substitution of prM and E genes.

6. The method of claim 1 wherein the heterologous nucleotide sequences of step (a) comprises in the 5' region the nucleotide of SEQ ID NO: 1, and comprises in the 3' region the stem and anchor domains of protein E, as set forth in SEQ ID NO: 3.

7. A DNA construct comprising the genome of a recombinant vector virus, wherein the vector virus comprises nucleotide sequences encoding at least one heterologous protein, or fragments thereof,
   wherein said vector virus sequence comprises nucleotide sequences encoding the NS1 protein and the E protein sequence of a *Flavivirus*;
   further wherein the heterologous sequence is inserted in the E/NS1 intergenic region, further wherein the nucleotides present at the 5' end of the NS1 gene and the whole or part of the domains of stem and anchor of the E protein are present at either end of the heterologous sequence; and
   wherein when the heterologous protein is expressed it will be processed normally by a host cell and can induce an immune response.

8. The DNA construct of claim 7, wherein the vector virus is a genetically stable virus, and is the genome of the Yellow Fever 17D virus, as set forth in SEQ ID NO: 15.

* * * * *